US011723923B2

(12) United States Patent
Perez et al.

(10) Patent No.: US 11,723,923 B2
(45) Date of Patent: Aug. 15, 2023

(54) METHODS OF PREPARING T CELLS FOR T CELL THERAPY

(71) Applicants: Kite Pharma, Inc., Santa Monica, CA (US); The United States of America, as represented by the Secretary, Department of Health and Human Services, Bethesda, MD (US)

(72) Inventors: Arianne Perez, Santa Monica, CA (US); Marianna Sabatino, Santa Monica, CA (US); Steven A. Rosenberg, Bethesda, MD (US); Nicholas P. Restifo, Bethesda, MD (US)

(73) Assignees: Kite Pharma, Inc., Santa Monica, CA (US); The United States of America, as represented by the Secretary, Department of Health and Human Services, Bethesda, MD (US)

( * ) Notice: Subject to any disclaimer, the term of this patent is extended or adjusted under 35 U.S.C. 154(b) by 764 days.

(21) Appl. No.: 16/533,109

(22) Filed: Aug. 6, 2019

(65) Prior Publication Data

US 2020/0206265 A1    Jul. 2, 2020

Related U.S. Application Data

(63) Continuation of application No. 15/299,394, filed on Oct. 20, 2016, now abandoned.
(Continued)

(51) Int. Cl.
*A61K 35/17* (2015.01)
*A61K 39/00* (2006.01)
(Continued)

(52) U.S. Cl.
CPC .......... *A61K 35/17* (2013.01); *A61K 39/0011* (2013.01); *A61K 39/00117* (2018.08); *A61K 39/00118* (2018.08); *A61K 39/001104* (2018.08); *A61K 39/001106* (2018.08); *A61K 39/001109* (2018.08); *A61K 39/001112* (2018.08); *A61K 39/001113* (2018.08); *A61K 39/001119* (2018.08); *A61K 39/001124* (2018.08); *A61K 39/001153* (2018.08); *A61K 39/001156* (2018.08); *A61K 39/001157* (2018.08); *A61K 39/001161* (2018.08); *A61K 39/001162* (2018.08); *A61K 39/001166* (2018.08); *A61K 39/001168* (2018.08); *A61K 39/001171* (2018.08); *A61K 39/001176* (2018.08); *A61K 39/001181* (2018.08); *A61K 39/001182* (2018.08); *A61K 39/001184* (2018.08); *A61K 39/001186* (2018.08); *A61K 39/001188* (2018.08); *A61K 39/001189* (2018.08); *A61K 39/001191* (2018.08); *A61K 39/001192* (2018.08);
(Continued)

(58) Field of Classification Search
CPC .... A61K 39/001189; A61K 39/001119; A61K 39/001124; A61K 39/00117; A61K 39/001161; A61K 39/001184; A61K 39/0011; A61K 39/001157; A61K 39/001191; A61K 39/001106; A61K 39/001171; A61K 39/001194; A61K 39/001153; A61K 39/001195; A61K 2039/572; A61K 39/001109; A61K 39/001181; A61K 39/001162; A61K 35/17; A61K 39/001193; A61K 39/001156; A61K 2039/5158; A61K 39/001104; A61K 39/001166; A61K 39/001168; A61K 39/001192; A61K 39/001112; A61K 39/00118; A61K 2039/5156; A61K 39/001182; A61K 39/001197; A61K 39/001176; A61K 39/001186; A61K 39/001188; A61K 39/001113; C12N 2501/2315; C12N 2501/727; C12N 5/0638; C12N 2501/2307; C12N 5/0636; C12N 2506/11; C12N 2501/2302; A61P 35/00; A61P 35/02; C07K 14/7051
See application file for complete search history.

(56) References Cited

U.S. PATENT DOCUMENTS 5,728,388 A    3/1998 Terman
7,273,869 B2   9/2007 Lindsley et al.
(Continued)

FOREIGN PATENT DOCUMENTS

WO    2008/081035 A1    7/2008
WO    2012/177925 A1    12/2012
WO    WO-2015188119     12/2015

OTHER PUBLICATIONS

English Translation and Original Office Action dated Apr. 9, 2020 in counterpart Chinese Patent Application No. 201680069582.6.
(Continued)

*Primary Examiner* — Satyendra K Singh
(74) *Attorney, Agent, or Firm* — Sheppard Mullin Richter & Hampton LLP

(57) ABSTRACT

Provided herein are methods for delaying or inhibiting T cell maturation or differentiation in vitro for a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit delayed maturation or differentiation. In some embodiments, the method further comprises administering the one or more T cells to a subject in need of a T cell therapy.

12 Claims, 28 Drawing Sheets

Related U.S. Application Data

(60) Provisional application No. 62/244,036, filed on Oct. 20, 2015.

(51) Int. Cl.
   *C07K 14/725* (2006.01)
   *C12N 5/0783* (2010.01)

(52) U.S. Cl.
   CPC .......... *A61K 39/001193* (2018.08); *A61K 39/001194* (2018.08); *A61K 39/001195* (2018.08); *A61K 39/001197* (2018.08); *C07K 14/7051* (2013.01); *C12N 5/0636* (2013.01); *C12N 5/0638* (2013.01); *A61K 2039/5156* (2013.01); *A61K 2039/5158* (2013.01); *A61K 2039/572* (2013.01); *C12N 2501/2302* (2013.01); *C12N 2501/2307* (2013.01); *C12N 2501/2315* (2013.01); *C12N 2501/727* (2013.01); *C12N 2506/11* (2013.01)

(56) References Cited

U.S. PATENT DOCUMENTS

| | | | |
|---|---|---|---|
| 7,446,190 | B2 | 11/2008 | Sadelain et al. |
| 2002/0006409 | A1 | 1/2002 | Wood |
| 2010/0168210 | A1 | 7/2010 | Edwards, III et al. |
| 2013/0045491 | A1 | 2/2013 | Unutmaz |
| 2013/0287748 | A1 | 10/2013 | June et al. |
| 2014/0050708 | A1 | 2/2014 | Powell et al. |
| 2014/0099309 | A1 | 4/2014 | Powell, Jr. et al. |
| 2014/0154228 | A1 | 6/2014 | Volk et al. |
| 2014/0227237 | A1 | 8/2014 | June et al. |
| 2017/0136063 | A1 | 5/2017 | Perez et al. |

OTHER PUBLICATIONS

Office Action dated Dec. 1, 2020 for Japanese Patent Application No. 2018-520185, English and Japanese versions.
English Translation and original Office Action in counterpart Israeli Application No. 258726, dated Apr. 13, 2021.
Akt inhibitor VIII—a product disclosure by ChemSpider, Royal Society of Chemistry, 2015, accessed on the web on 02101/2019 at http://www.chemspider.com/Chemicai-Structure.8371999.html, total pp. 1-4, (2015).
Zhang Y. et al., "Interieukin-7 Inhibits Tumor-Induced CD27-CD28-Suppressor T Cells: Implications for Cancer Immunotherapy", Clin. Cancer Res., 2011, vol. 17, No. 15, pp. 4975-4986, (2011).
Okuzumi T. et al., "Inhibitor Hijacking of Akt Activation", Nat. Chem. Biol., 2009; vol. 5, No. 7, pp. 484-193, (2009).
Kochenderfer et al., "Construction and Pre-clinical Evaluation of an Anti-CDI9 Chimeric Antigen Receptor", J. Immunother., 32(7):689-702 (2009).
Van der Waart et al., "Akt Signalling Inhibition Promotes the Ex Vivo Generation of Minor Histocompatibility Antigen-Specific CDS+ Memory Stem T Cells", Blood, 122:3269 (2013).
Third Party Observation for European Application No. EP20160858247, dated Nov. 28, 2018 (5 pages).
International Search Report for PCT/US2016/057983, dated Jan. 24, 2017 (3 pages).
Van der Waart et al., "Inhibition of Akt signaling promotes the generation of superior tumor-reactive T cells for adoptive Immunotherapy," Blood, 124(23):3490-3500 (2014).
Gattinoni et al., Adoptive immunotherapy for cancer: building on success, Nat. Rev. Immunol., 6 (5):383-393 (2006).
Written Opinion of the International Searching Authority for PCT/US2016/057983, dated Jan. 24, 2017 (6 pages).
Extended European Serach Report and Supplementary Search Report for European Patent Application No. 16858247.6, dated Jun. 12, 2019 (6 pages).
Non-Final office action received for U.S. Appl. No. 15/299,394, dated Feb. 6, 2019, 13 pages.
Third-Party Submission Under 37 CFR 1.290 received for U.S. Appl. No. 15/299,394, dated Apr. 18, 2018, 3 pages.
International Preliminary Report received for PCT Application Serial No. PCT/US2016/057983, dated Apr. 24, 2018, 7 pages.
Extended European Search Report dated Jul. 29, 2020 in counterpart European Patent Application No. 19218292.1.
Cieri et al., IL-7 and IL-15 instruct the generation of human memory stem T cells from naive precursors. Blood 2013; vol. 121, No. 4, pp. 573-584.
Notice of Preliminary Rejection for Korean Patent Application No. 10-2018-7013840 dated Feb. 9, 2022. 6 pages.
Office Action (and English Translation) issued in Taiwanese Patent Application No. 109141098, dated Dec. 2, 2021; Office Action 9 pages, English Translation 10 pages, total pp. 19.
Office Action (and English Translation) issued in Indian Application No. 201817018192, dated Sep. 29, 2021; total pp. 6.
Office Action issued in Australian Patent Application No. 2016341966, dated Jul. 31, 2021; Office Action 3 pages.
International Search Report (and English Translation) issued in Brazilian Application No. BR112018007864-6, dated Sep. 9, 2021; International Search Report 4 pages, English Translation 4 pages, total pp. 8.
Original and English Translation of Office Action dated May 22, 2020 in counterpart Taiwan Patent Application No. 105133906.
Intention To Grant dated May 25, 2020 European Patent Application No. 15802488.5, not a counterpart of the instant application.
Decision of Rejection for Taiwan Patent Application No. 109141098 dated Jun. 29, 2022. 11 pages.
Examination Report for Australian Patent Application No. 2016341966 dated Jul. 27, 2022. 3 pages.
Notice of Final Rejection for Korean Patent Application No. 10-2018-7013840 dated Jun. 15, 2022. 7 pages.
Examination Report for European Application No. 19218292.1 dated Oct. 18, 2022. 4 pages.
Geginat et al., Cytokine-driven Proliferation and Differentiation of Human Naive, Central Memory, and Effector Memory CD4+ T Cells, J. Exp. Med. 2001, vol. 194, No. 12, pp. 1711-1719.
Notice of Second Final Rejection and Dismissal of Amendment for Korean Application No. 10-2018-7013840 dated Oct. 19, 2022. 16 pages.
Office Action for Canadian Application No. 3,001,613 dated Nov. 14, 2022. 5 pages.
Office Action for Japanese Application No. 2021-155667 dated Feb. 28, 2023. 8 pages.
Office Action for Mexican Application No. MX/a/2018/004614 dated Sep. 23, 2022. 8 pages.

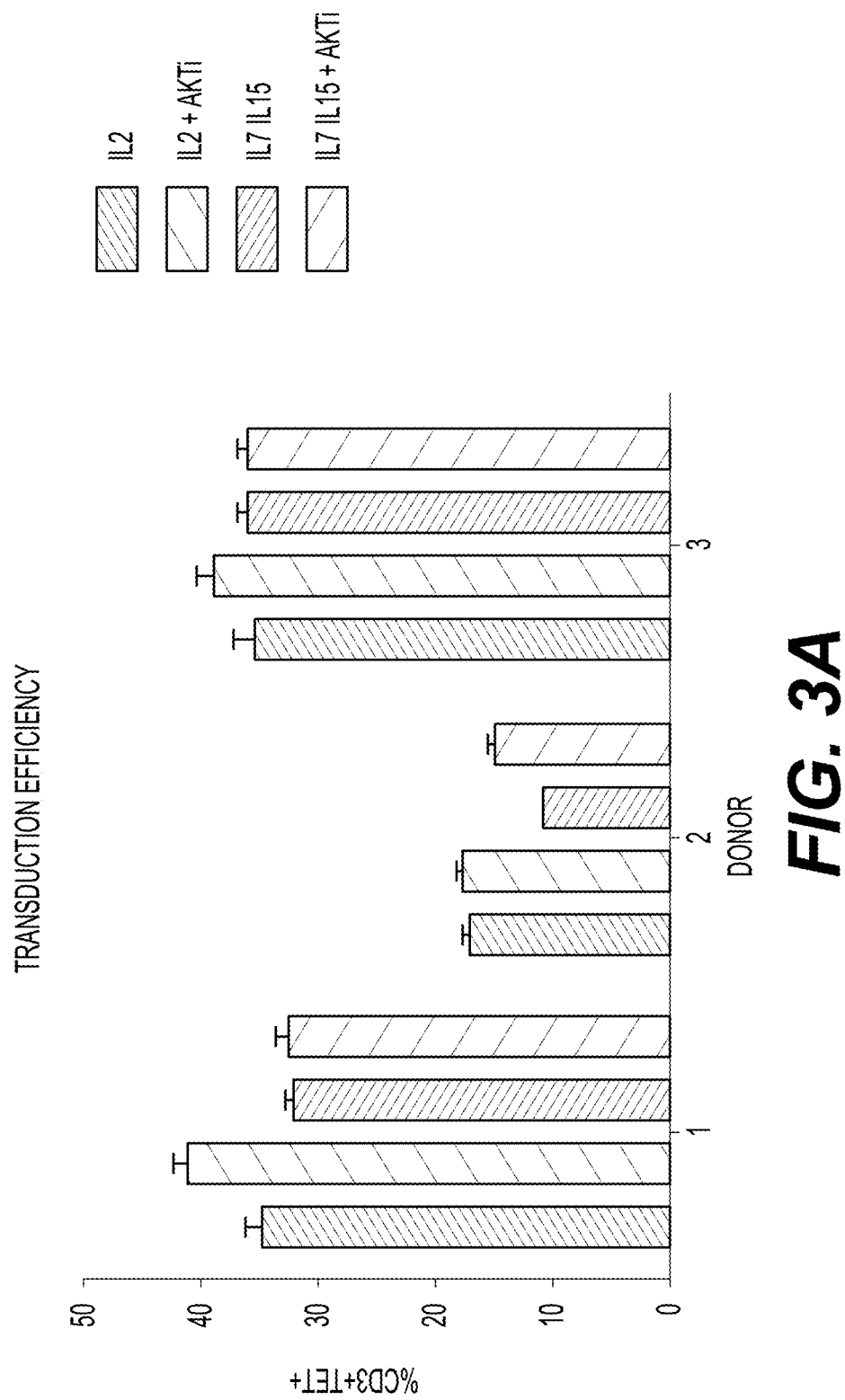

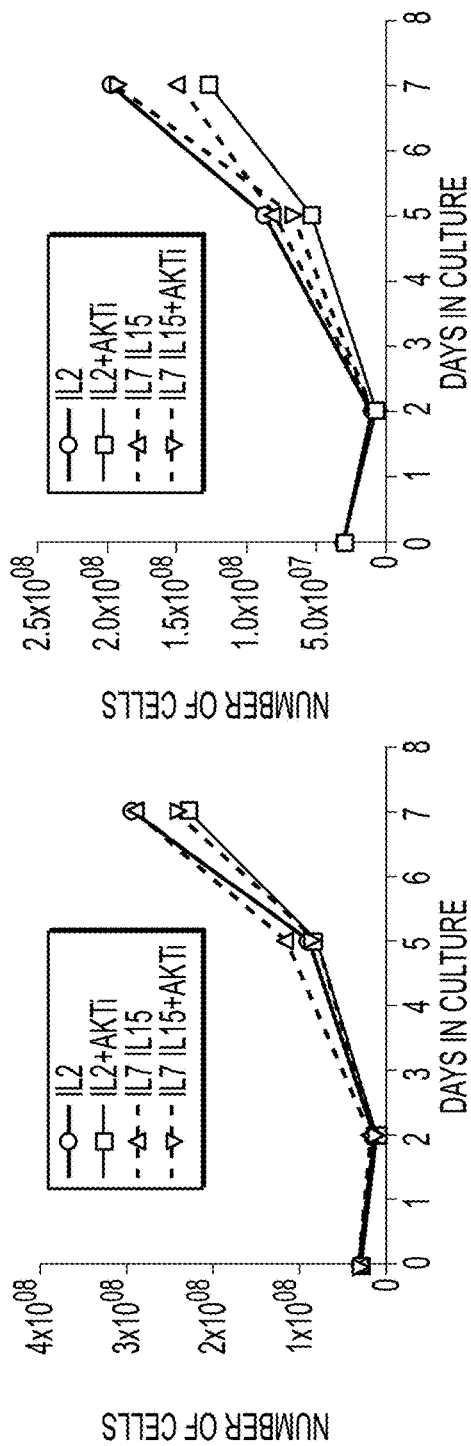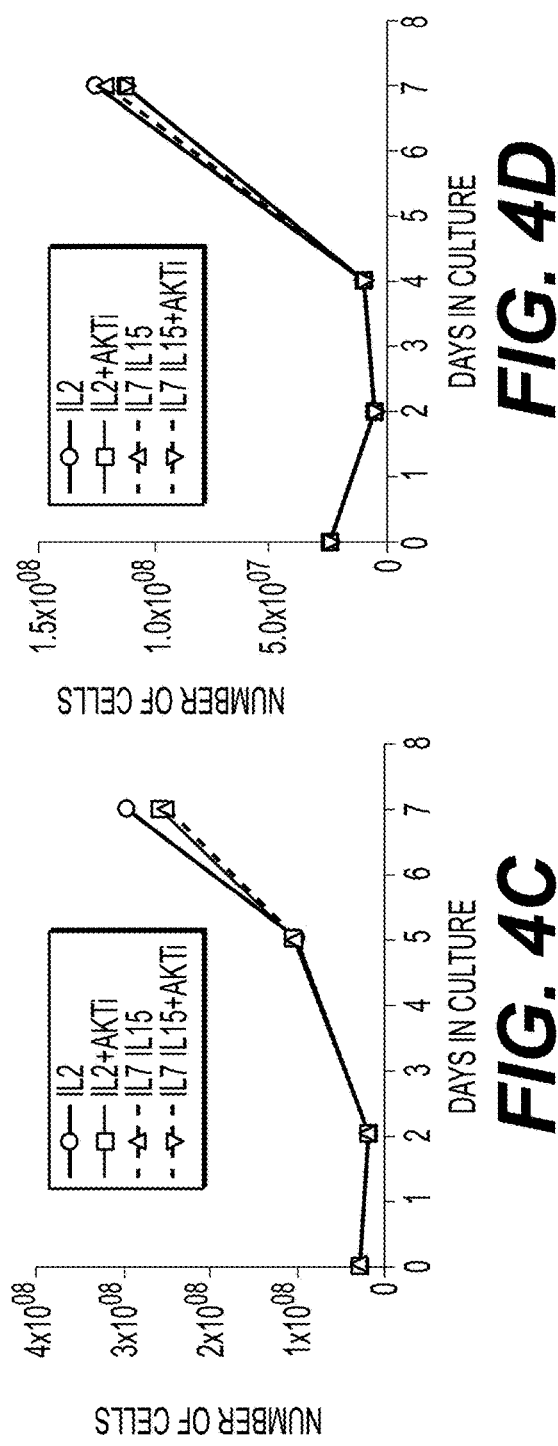
FIG. 4A  FIG. 4B  FIG. 4C  FIG. 4D

METHODS OF PREPARING T CELLS FOR T CELL THERAPY

CROSS-REFERENCE TO RELATED APPLICATIONS

This application is a continuation of U.S. patent application Ser. No. 15/299,394, filed Oct. 20, 2016, which claims the benefit of priority to U.S. Provisional Patent Application 62/244,036, filed Oct. 20, 2015, both of which are incorporated by reference in their entirety.

STATEMENT OF GOVERNMENT INTEREST

This invention was created in the performance of a Cooperative Research and Development Agreement with the National Cancer Institute (NCI), an Agency of the Department of Health and Human Services. The Government of the United States has certain rights in this invention.

FIELD OF THE INVENTION

This invention relates to methods of preparing one or more T cells for a T cell therapy. In particular, the invention relates to a method of improving the efficacy of a T cell therapy by contacting one or more T cells with an AKT inhibitor ("AKTi") and at least one of exogenous Interleukin-7 (IL-7) and exogenous Interleukin-15 (IL-15).

BACKGROUND

Human cancers are by their nature comprised of normal cells that have undergone a genetic or epigenetic conversion to become abnormal cancer cells. In doing so, cancer cells begin to express proteins and other antigens that are distinct from those expressed by normal cells. These aberrant tumor antigens can be used by the body's innate immune system to specifically target and kill cancer cells. However, cancer cells employ various mechanisms to prevent immune cells, such as T and B lymphocytes, from successfully targeting cancer cells.

Human T cell therapies rely on ex-vivo-enriched or modified human T cells to target and kill cancer cells in a subject, e.g., a patient. Various technologies have been developed to enrich the concentration of naturally occurring T cells capable of targeting a tumor antigen or genetically modifying T cells to specifically target a known cancer antigen. These therapies have proven to have promising effects on tumor size and patient survival. However, it has proven difficult to predict whether a given T cell therapy will be effective in each patient.

Transplantation of a mixed population of T cells is among the factors hindering T cell therapies from reaching their full potential. In conventional T cell therapies, donor T cells are collected, optionally modified to target a specific antigen (e.g., a tumor cell) or selected for anti-tumor characteristics (e.g., tumor infiltrating lymphocytes), expanded in vitro, and administered to a subject in need thereof. Typically, the resulting T cells comprise a mixed population of largely mature cells, many of which are terminally differentiated. As a result, the expected in vivo persistence of these cells can be limited, and positive effects initially observed can be undone over time as tumors rebound in the absence of transplanted T cells. Thus, there remains a need to increase the in vivo persistence of T cells for use in a T cell therapy.

SUMMARY OF THE INVENTION

The present disclosure provides a method for delaying or inhibiting T cell maturation or differentiation in vitro for a T cell therapy, comprising contacting one or more T cells from a subject in need of a T cell therapy with an AKTi and at least one of exogenous IL-7 and exogenous IL-15, wherein the resulting T cells exhibit delayed maturation or differentiation.

The present disclosure further provides a method for delaying or inhibiting T cell maturation or differentiation in vitro comprising culturing one or more T cells in a medium comprising an AKTi and at least one of an exogenous IL-7 and exogenous IL-15.

The present disclosure further provides a method for generating stem-cell like CD8$^+$ T cells comprising culturing one or more T cells in a medium comprising contacting one or more T cells with an AKTi and at least one of exogenous IL-7 and exogenous IL-15.

The present disclosure also provides a method for extending the in vivo persistence of one or more T cells in an adoptive cell therapy comprising contacting the one or more T cells with an AKTi and at least one of an exogenous IL-7 and exogenous IL-15 prior to administration to a subject.

In certain embodiments, the methods disclosed herein further comprise administering the one or more T cells to a subject in need thereof. In some embodiments, the subject is in need of a T cell therapy.

The present disclosure further provides a method of treating a tumor in a subject in need of a T cell therapy comprising administering to the subject one or more T cells, wherein the one or more T cells have been contacted with (i) an AKTi and (ii) exogenous IL-7 and/or exogenous IL-15.

The present disclosure also provides a method of reducing or decreasing the size of a tumor or inhibiting growth of a tumor in a subject in need of a T cell therapy comprising administering to the subject one or more T cells, wherein the one or more T cells have been contacted with (i) an AKTi and (ii) exogenous IL-7 and/or exogenous IL-15.

In certain embodiments, the T cell therapy comprises an engineered CAR cell therapy or an engineered TCR cell therapy. In one embodiment, the engineered CAR cell or engineered TCR cell therapy treats a tumor in a subject.

BRIEF DESCRIPTION OF THE DRAWINGS

FIG. 1A and FIG. 1C show the percent of the total population of cultured CD4$^+$ T cells and CD8$^+$ T cells, respectively, that were characterized as naïve T cells or central memory T cells (Tcm) at day 7 for IL-2 and IL-7/IL-15 treated cells. FIG. 1B and FIG. 1D show the percent of the total population of cultured CD4$^+$ T cells and CD8$^+$ T cells, respectively, that were characterized as effector memory T cells (Tem) or effector T cells (Teff) at day 7 for IL-2 and IL-7/IL-15 treated cells. FIG. 1E show the percent of the total population of cultured CD8$^+$ T cells that were characterized as naïve T cells or central memory T cells (Tcm) at day 14 for IL-2 and IL-7/IL-15 treated cells. FIG. 1F show the percent of the total population of cultured CD8$^+$ T cells that were characterized as effector memory T cells (Tem) or effector T cells (Teff) at day 14 for IL-2 and IL-7/IL-15 treated cells. Individual data points reflect individual samples. Horizontal lines denote the average, and error bars indicate the standard deviation. Statistical significance is indicated by the p value ("ns" stands for "not significant").

FIG. 2A and FIG. 2C show the percent of the total population of cultured CD4$^+$ T cells and CD8$^+$ T cells, respectively, that were characterized as naïve T cells or Tcm cells at day 7 for IL-7/IL-15 and IL-7/IL-15/AKTi treated cells. FIG. 2B and FIG. 2D show the percent of the total population of cultured CD4$^+$ T cells and CD8$^+$ T cells, respectively, that were characterized as Tem or Teff cells at day 7 IL-7/IL-15 and IL-7/IL-15/AKTi treated cells. Individual data points reflect individual samples. Horizontal lines denote the average, and error bars indicate the standard deviation. Statistical significance is indicated by the p value ("ns" stands for "not significant").

FIG. 3A shows the transduction efficiency of donor T cells contacted with IL-2 alone; IL-2 and AKTi; IL-7 and IL-15; and IL-7, IL-15, and AKTi. Transduction efficiency is indicated by the percent of total T cells that are CD3$^+$ and that have positive soluble MHC-tetramer staining (Tet$^+$). Dark grey bars represent the percent of CD3$^+$ Tet$^+$ cells in T cell samples contacted with IL-2. Downward-striped bars represent the percent of CD3$^+$ Tet$^+$ cells in T cell samples contacted with IL-2 and AKTi. Light grey bars represent the percent of CD3$^+$ Tet$^+$ cells in T cell samples contacted with IL-7 and IL-15. Upward-striped bars represent the percent of CD3$^+$ Tet$^+$ cells in T cell samples contacted with IL-7, IL-15, and AKTi. Error bars indicate the standard deviation.

FIGS. 4A-4D illustrate cell expansion over the course of 7 days for cells from four donors cultured in the presence of IL-2 (circles); IL-2 and AKTi (squares); IL-7 and IL-15 (triangles); or IL-7, IL-15, and AKTi (inverted triangles). Each of FIGS. 4A-4D represents cell expansion for a single donor cell line. Source material for expansion protocol were peripheral blood mononuclear cells.

FIGS. 9B-9C: squares) or IL-7, IL-15, and AKTi (FIG. 9A: squares; FIGS. 9B-9C: circles). Cells were grown at large manufacturing scale in a XURI™ Cell Expansion System. Each of FIGS. 9A-9D represents cell expansion for a single donor cell line. Source material for expansion protocol were isolated CD4+ and CD8+ cells.

FIGS. 11C and 11F show FACS analyses of the distribution of cells expressing the CDR and the transduced TCR for both donors.

FIG. 16A shows the amount of IFNg produced (pg/mL; y-axis) by T cells from three donors (x-axis) following coculture with a tumor cell line (Caski; cervical carcinoma cell line) expressing the TCR antigen in the presence of IL-2 alone; IL-2 and AKTi; IL-7 and IL-15; or IL-7, IL-15, and AKTi.

FIGS. 17A-17D are FACS histograms showing T cell proliferation following culture in the presence (FIGS. 17B and 17D) or absence of AKTi (FIGS. 17A and 17C). T cells from Donor 3 were grown in IL-2 (FIG. 17A), IL-2 and AKTi (FIG. 17B), IL-7 and IL-15 (FIG. 17C) and IL-7, IL-15 and AKTi (FIG. 17D), transduced with a class II TCR (MAGE-A3), and cocultured with a tumor cell line expressing the TCR antigen for 4 days. T cell proliferation was measured by carboxyfluorescein succinimidyl ester (CFSE) staining (FIGS. 17A-17D). L=late proliferation; M=medium proliferation; and E=early proliferation.

DETAILED DESCRIPTION

Figure 1A:
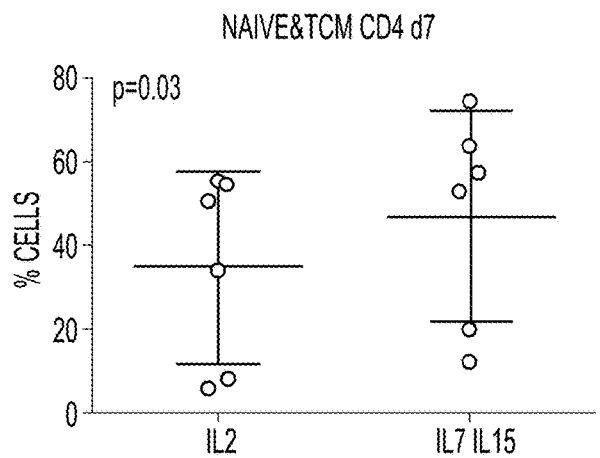
FIG. 1A-FIG. 1F show the phenotype of CD4$^+$ T cells and CD8+ T cells following culture in the presence of IL-2 or in the presence of IL-7 and IL-15 at 7 and 14 days.

The present invention relates to methods for preparing T cells for use in a T cell therapy. In particular, the present invention relates to methods of modulating, e.g., delaying or inhibiting, T cell maturation or differentiation in vitro by contacting one or more T cells with an AKTi and at least one of exogenous IL-7 and exogenous IL-15. By delaying or inhibiting T cell maturation or differentiation, a collection of donor T cells can be enriched for immature, less differentiated T cells (e.g., naïve T cells of central memory Tcm cells), increasing the potential persistence of the one or more T cells once administered to a subject, e.g., a patient. As a result, the enriched population of immature T cells is more likely to generate a sustained anti-tumor effect than a population of T cells at mixed stages of differentiation.

Definitions

In order that the present disclosure can be more readily understood, certain terms are first defined. As used in this application, except as otherwise expressly provided herein, each of the following terms shall have the meaning set forth below. Additional definitions are set forth throughout the application.

Unless defined otherwise, all technical and scientific terms used herein have the same meaning as commonly understood by one of ordinary skill in the art to which this disclosure is related. For example, the Concise Dictionary of Biomedicine and Molecular Biology, Juo, Pei-Show, 2nd ed., 2002, CRC Press; The Dictionary of Cell and Molecular Biology, 3rd ed., 1999, Academic Press; and the Oxford Dictionary Of Biochemistry And Molecular Biology, Revised, 2000, Oxford University Press, provide one of skill with a general dictionary of many of the terms used in this disclosure.

Units, prefixes, and symbols are denoted in their Système International de Unites (SI) accepted form. Numeric ranges are inclusive of the numbers defining the range. The headings provided herein are not limitations of the various aspects of the disclosure, which can be had by reference to the specification as a whole. Accordingly, the terms defined immediately below are more fully defined by reference to the specification in its entirety.

As used herein, the indefinite articles "a" or "an" should be understood to refer to "one or more" of any recited or enumerated component.

The terms "about" or "comprising essentially of" refer to a value or composition that is within an acceptable error range for the particular value or composition as determined by one of ordinary skill in the art, which will depend in part on how the value or composition is measured or determined, i.e., the limitations of the measurement system. For example, "about" or "comprising essentially of" can mean within 1 or more than 1 standard deviation per the practice in the art. Alternatively, "about" or "comprising essentially of" can mean a range of up to 10% (i.e., ±10%). For example, about 3 mg can include any number between 2.7 mg and 3.3 mg (for 10%). Furthermore, particularly with respect to biological systems or processes, the terms can mean up to an order of magnitude or up to 5-fold of a value. When particular values or compositions are provided in the application and claims, unless otherwise stated, the meaning of "about" or "comprising essentially of" should be assumed to be within an acceptable error range for that particular value or composition.

As described herein, any concentration range, percentage range, ratio range or integer range is to be understood to include the value of any integer within the recited range and, when appropriate, fractions thereof (such as one-tenth and one-hundredth of an integer), unless otherwise indicated.

The term "and/or" where used herein is to be taken as specific disclosure of each of the two specified features or components with or without the other. Thus, the term "and/or" as used in a phrase such as "A and/or B" herein is intended to include "A and B," "A or B," "A" (alone), and "B" (alone). Likewise, the term "and/or" as used in a phrase such as "A, B, and/or C" is intended to encompass each of the following aspects: A, B, and C; A, B, or C; A or C; A or B; B or C; A and C; A and B; B and C; A (alone); B (alone); and C (alone).

It is understood that wherever aspects are described herein with the language "comprising," otherwise analogous aspects described in terms of "consisting of" and/or "consisting essentially of" are also provided. The term "activation" or "activated" refers to the state of an immune cell, e.g., a T cell, that has been sufficiently stimulated to induce detectable cellular proliferation. Activation can also be associated with induced cytokine production and detectable effector functions. The term "activated T cells" refers to, among other things, T cells that are undergoing cell division. T cell activation can be characterized by increased T cell expression of one or more biomarker, including, but not limited to, CD57, PD1, CD107a, CD25, CD137, CD69, and/or CD71.

"Administering" refers to the physical introduction of an agent to a subject, using any of the various methods and delivery systems known to those skilled in the art. Exemplary routes of administration for the T cells prepared by the methods disclosed herein include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, the T cells prepared by the present methods is administered via a non-parenteral route, e.g., orally. Other non-parenteral routes include a topical, epidermal or mucosal route of administration, for example, intranasally, vaginally, rectally, sublingually or topically. Administering can also be performed, for example, once, a plurality of times, and/or over one or more extended periods.

The term "AKT inhibitor," "AKTI," or "AKTi" can be used interchangeably and refers to any molecule (e.g., AKT antagonist), including, but not limited to a small molecule, a polynucleotide (e.g., DNA or RNA), or a polypeptide (e.g., an antibody or an antigen-binding portion thereof), capable of blocking, reducing, or inhibiting the activity of AKT. AKT is a serine/threonine kinase, also known as protein kinase B or PKB. An AKT inhibitor can act directly on AKT, e.g., by binding AKT, or it can act indirectly, e.g., by interfering with the interaction between AKT and a binding partner or by inhibiting the activity of another member of the PI3K-AKT-mTOR pathway. Non-limiting examples of AKTi are shown in other sections of this application.

The term "antibody" (Ab) includes, without limitation, an immunoglobulin which binds specifically to an antigen. In general, an antibody can comprise at least two heavy (H) chains and two light (L) chains interconnected by disulfide bonds. Each H chain comprises a heavy chain variable region (abbreviated herein as VH) and a heavy chain constant region. The heavy chain constant region can comprise three or four constant domains, CH1, CH2 CH3, and/or CH4. Each light chain comprises a light chain variable region (abbreviated herein as VL) and a light chain constant region. The light chain constant region can comprise one constant domain, CL. The VH and VL regions can be further subdivided into regions of hypervariability, termed complementarity determining regions (CDRs), interspersed with regions that are more conserved, termed framework regions (FR). Each VH and VL comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen, e.g., AKT.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the Ab class or subclass (e.g., IgM or IgG1) that is encoded by the heavy chain constant region genes. The term "antibody" includes, by way of example, both naturally occurring and non-naturally occurring Abs; monoclonal and polyclonal Abs; chimeric and humanized Abs; human or nonhuman Abs; wholly synthetic Abs; and single chain Abs. A nonhuman Ab can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain Ab.

An "antigen binding molecule" or "antibody fragment" refers to any portion of an antibody less than the whole. An antigen binding molecule can include the antigenic complementarity determining regions (CDRs). Examples of antibody fragments include, but are not limited to, Fab, Fab', F(ab')2, and Fv fragments, dAb, linear antibodies, scFv antibodies, and multispecific antibodies formed from antigen binding molecules.

The term "autologous" refers to any material derived from the same individual to which it is later to be re-introduced. For example, the engineered autologous cell therapy (eACT™) method described herein involves collection of lymphocytes from a donor, e.g., a patient, which are then engineered to express, e.g., a CAR construct, and then administered back to the same donor, e.g., patient.

The term "allogeneic" refers to any material derived from one individual which is then introduced to another individual of the same species, e.g., allogeneic T cell transplantation.

A "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. A "cancer" or "cancer tissue" can include a tumor at various stages. In certain embodiments, the cancer or tumor is stage 0, such that, e.g., the cancer or tumor is very early in development and has not metastasized. In some embodiments, the cancer or tumor is stage I, such that, e.g., the cancer or tumor is relatively small in size, has not spread into nearby tissue, and has not metastasized. In other embodiments, the cancer or tumor is stage II or stage III, such that, e.g., the cancer or tumor is larger than in stage 0 or stage I, and it has grown into neighboring tissues but it has not metastasized, except potentially to the lymph nodes. In other embodiments, the cancer or tumor is stage IV, such that, e.g., the cancer or tumor has metastasized. Stage IV can also be referred to as advanced or metastatic cancer.

An "anti-tumor effect" as used herein, refers to a biological effect that can present as a decrease in tumor volume, an inhibition of tumor growth, a decrease in the number of tumor cells, a decrease in tumor cell proliferation, a decrease in the number of metastases, an increase in overall or progression-free survival, an increase in life expectancy, or amelioration of various physiological symptoms associated with the tumor. An anti-tumor effect can also refer to the prevention of the occurrence of a tumor, e.g., a vaccine.

The term "progression-free survival," which can be abbreviated as PFS, as used herein refers to the time from the treatment date to the date of disease progression per the revised IWG Response Criteria for Malignant Lymphoma or death from any cause.

"Disease progression" is assessed by measurement of malignant lesions on radiographs or other methods should not be reported as adverse events. Death due to disease progression in the absence of signs and symptoms should be reported as the primary tumor type (e.g., DLBCL).

The "duration of response," which can be abbreviated as DOR, as used herein refers to the period of time between a subject's first objective response to the date of confirmed disease progression, per the revised IWG Response Criteria for Malignant Lymphoma, or death.

The term "overall survival," which can be abbreviated as OS, is defined as the time from the date of treatment to the date of death.

A "cytokine," as used herein, refers to a non-antibody protein that can be released by immune cells, including macrophages, B cells, T cells, and mast cells to propagate an immune response. In some embodiments, one or more cytokines are released in response to the T cell therapy. In certain embodiments, those cytokines secreted in response to the T cell therapy can be a sign of effective T cell therapy.

A "therapeutically effective amount" or "therapeutically effective dosage," as used herein, refers to an amount of the T cells or the DC cells that are produced by the present methods and that, when used alone or in combination with another therapeutic agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of the T cells or DC cells to promote disease regression can be evaluated using a variety of methods known to the skilled practitioner, such as in human subjects during clinical trials, in animal model systems predictive of efficacy in humans, or by assaying the activity of the agent in in vitro assays.

The term "effective amount" or "effective dose" as used herein, refers to the amount of one or more inhibitors of T cell maturation, (e.g., an AKTi, IL-7, and IL-15), which together elicits a desired response. Therefore, an effective amount of AKTi, an effective amount of IL-7, and an effective amount of IL-15 to delay or inhibit T cell differentiation or maturation can be lower than an effective amount of AKTi only, an effective amount of IL-7 only, or an effective amount of IL-15 only. In other embodiments, an effective dose of an AKTi can refer to the amount, e.g., the concentration, of an AKTi, which reduces AKT activity by a desired amount, such as by at least about 10%, at least 20%, at least about 30%, at least about 40%, at least about 50%, at least about 60%, at least about 70%, at least about 80%, at least about 90%, or about 100%.

The term "lymphocyte" as used herein can include natural killer (NK) cells, T cells, or B cells. NK cells are a type of cytotoxic (cell toxic) lymphocyte that represent a major component of the inherent immune system. NK cells reject tumors and cells infected by viruses. It works through the process of apoptosis or programmed cell death. They were termed "natural killers" because they do not require activation in order to kill cells. T-cells play a major role in cell-mediated-immunity (no antibody involvement). Its T-cell receptors (TCR) differentiate themselves from other lymphocyte types. The thymus, a specialized organ of the immune system, is primarily responsible for the T cell's maturation.

There are several types of T-cells, namely: Helper T-cells (e.g., CD4+ cells, effector $T_{EFF}$ cells), Cytotoxic T-cells (also known as TC, cytotoxic T lymphocyte, CTL, T-killer cell, cytolytic T cell, CD8+ T-cells or killer T cell), Memory T-cells ((i) stem memory $T_{SCM}$ cells, like naïve cells, are CD45RO−, CCR7+, CD45RA+, CD62L+(L-selectin), CD27+, CD28+ and IL-7Rα+, but they also express large amounts of CD95, IL-2Rβ, CXCR3, and LFA-1, and show numerous functional attributes distinctive of memory cells); (ii) central memory $T_{CM}$ cells express L-selectin and are $CCR7^+$ and $CD45RO^+$ and they secrete IL-2, but not IFNγ or IL-4, and (iii) effector memory $T_{EM}$ cells, however, do not express L-selectin or CCR7 but do express CD45RO and produce effector cytokines like IFNγ and IL-4), Regulatory T-cells (Tregs, suppressor T cells, or CD4+CD25+ regulatory T cells), Natural Killer T-cells (NKT), and Gamma Delta T-cells. T cells found within tumors are referred to as "tumor infiltrating lymphocytes" or "TIL." B-cells, on the other hand, play a principal role in humoral immunity (with antibody involvement). It makes antibodies and antigens and performs the role of antigen-presenting cells (APCs) and turns into memory B-cells after activation by antigen interaction. In mammals, immature B-cells are formed in the bone marrow, where its name is derived from.

A "naïve" T cell refers to a mature T cell that remains immunologically undifferentiated. Following positive and negative selection in the thymus, T cells emerge as either $CD4^+$ or $CD8^+$ naïve T cells. In their naïve state, T cells express L-selectin ($CD62L^+$), IL-7 receptor-α (IL-7R-α), and CD132, but they do not express CD25, CD44, CD69, or CD45RO. As used herein, "immature" can also refers to a T cell which exhibits a phenotype characteristic of either a naïve T cell or an immature T cell, such as a $T_{SCM}$ cell or a $T_{CM}$ cell. For example, an immature T cell can express one or more of L-selectin ($CD62L^+$), IL-7Rα, CD132, CCR7, CD45RA, CD45RO, CD27, CD28, CD95, CXCR3, and LFA-1. Naïve or immature T cells can be contrasted with terminal differentiated effector T cells, such as $T_{EM}$ cells and $T_{EFF}$ cells.

"T cell function," as referred to herein, refers to normal characteristics of healthy T cells. In some embodiments, a T cell function comprises T cell proliferation. In some embodiments, a T cell function comprises a T cell activity. In some embodiments, the T cell function comprises cytolytic activity. In some embodiments, the methods of the present invention, e.g., culturing T cells in the presence of an AKT inhibitor (and optionally IL-7 and/or IL-15), increase one or more T cell function, thereby making the T cells more fit and/or more potent for a T cell therapy. In some embodiments, T cells cultured according to the present methods have increased T cell function as compared to T cells cultured under conditions lacking an AKT inhibitor (or an AKTi, IL-7, and IL-15). In certain embodiments, T cells cultured according to the present methods have increased T cell proliferation as compared to T cells cultured under conditions lacking an AKT inhibitor (or an AKTi, IL-7, and IL-15). In certain embodiments, T cells cultured according to the present methods have increased T cell activity as compared to T cells cultured under conditions lacking an AKT inhibitor (or an AKTi, IL-7, and IL-15). In certain embodiments, T cells cultured according to the present methods have increased cytolytic activity as compared to T cells cultured under conditions lacking an AKT inhibitor (or an AKTi, IL-7, and IL-15).

Cell "proliferation," as used herein, refers to the ability of T cells to grow in numbers through cell division. Proliferation can be measured by staining cells with carboxyfluorescein succinimidyl ester (CFSE). Cell proliferation can occur in vitro, e.g., during T cell culture, or in vivo, e.g., following administration of a T cell therapy.

"T cell activity," as used herein, refers to any activity common to healthy T cells. In some embodiments, the T cell activity comprises cytokine production. In certain embodiments, the T cell activity comprises production of one or more cytokine selected from interferon gamma (IFNg), tissue necrosis factor alpha (TNFa), and both.

A "cytolytic activity" or "cytotoxicity," as used herein, refers to the ability of a T cell to destroy a target cell. In some embodiments, the target cell is a cancer cell, e.g., a tumor cell. In some embodiments, the T cell expresses a chimeric antigen receptor (CAR) or a T cell receptor (TCR), and the target cell expresses a target antigen.

The term "genetically engineered," "gene editing," or "engineered" refers to a method of modifying the genome of a cell, including, but not limited to, deleting a coding or non-coding region or a portion thereof or inserting a coding region or a portion thereof. In some embodiments, the cell that is modified is a lymphocyte, e.g., a T cell, which can either be obtained from a patient or a donor. The cell can be modified to express an exogenous construct, such as, e.g., a chimeric antigen receptor (CAR) or a T cell receptor (TCR), which is incorporated into the cell's genome.

An "immune response" refers to the action of a cell of the immune system (for example, T lymphocytes, B lymphocytes, natural killer (NK) cells, macrophages, eosinophils, mast cells, dendritic cells and neutrophils) and soluble macromolecules produced by any of these cells or the liver (including Abs, cytokines, and complement) that results in selective targeting, binding to, damage to, destruction of, and/or elimination from a vertebrate's body of invading pathogens, cells or tissues infected with pathogens, cancerous or other abnormal cells, or, in cases of autoimmunity or pathological inflammation, normal human cells or tissues.

The term "immunotherapy" refers to the treatment of a subject afflicted with, or at risk of contracting or suffering a recurrence of, a disease by a method comprising inducing, enhancing, suppressing or otherwise modifying an immune response. Examples of immunotherapy include, but are not limited to, T cell therapies. T cell therapy can include adoptive T cell therapy, tumor-infiltrating lymphocyte (TIL) immunotherapy, autologous cell therapy, engineered autologous cell therapy (eACT™), and allogeneic T cell transplantation. However, one of skill in the art would recognize that the methods of preparing T cells disclosed herein would enhance the effectiveness of any transplanted T cell therapy. Examples of T cell therapies are described in U.S. Patent Publication Nos. 2014/0154228 and 2002/0006409, U.S. Pat. No. 5,728,388, and International Publication No. WO 2008/081035.

The T cells of the immunotherapy can come from any source known in the art. For example, T cells can be differentiated in vitro from a hematopoietic stem cell population, or T cells can be obtained from a donor. The donor can be a subject, e.g., a subject in need of an anti-cancer treatment. T cells can be obtained from, e.g., peripheral blood mononuclear cells, bone marrow, lymph node tissue, cord blood, thymus tissue, tissue from a site of infection, ascites, pleural effusion, spleen tissue, and tumors. In addition, the T cells can be derived from one or more T cell lines available in the art. T cells can also be obtained from a unit of blood collected from a subject using any number of techniques known to the skilled artisan, such as FICOLL™ separation and/or apheresis. T cells can also be obtained from an artificial thymic organoid (ATO) cell culture system, which replicates the human thymic environment to support efficient ex vivo differentiation of T-cells from primary and reprogrammed pluripotent stem cells. Additional methods of isolating T cells for a T cell therapy are disclosed in U.S. Patent Publication No. 2013/0287748, which is herein incorporated by references in its entirety.

The term "engineered Autologous Cell Therapy," which can be abbreviated as "eACT™," also known as adoptive cell transfer, is a process by which a patient's own T cells are collected and subsequently genetically altered to recognize and target one or more antigens expressed on the cell surface of one or more specific tumor cells or malignancies. T cells can be engineered to express, for example, chimeric antigen receptors (CAR) or T cell receptor (TCR). CAR positive (+) T cells are engineered to express an extracellular single chain variable fragment (scFv) with specificity for a particular tumor antigen linked to an intracellular signaling part comprising a costimulatory domain and an activating domain. The costimulatory domain can be derived from, e.g., CD28, CTLA4, CD16, OX-40, 4-1BB/CD137, CD2, CD7, CD27, CD30, CD40, programmed death-1 (PD-1), programmed death ligand-1 (PD-L1), inducible T cell costimulator (ICOS), ICOS-L, lymphocyte function-associated antigen-1 (LFA-1 (CD1 1a/CD18), CD3 gamma, CD3 delta, CD3 epsilon, CD247, CD276 (B7-H3), LIGHT (tumor necrosis factor superfamily member 14; TNFSF14), NKG2C, Ig alpha (CD79a), DAP-10, Fc gamma receptor, MHC class I molecule, TNF receptor proteins, Immunoglobulin-like proteins, cytokine receptors, integrins, signaling lymphocytic activation molecules (SLAM proteins), activating NK cell receptors, BTLA, a Toll ligand receptor, ICAM-1, B7-H3, CDS, ICAM-1, GITR, BAFFR, LIGHT, HVEM (LIGHTR), KIRDS2, SLAMF7, NKp80 (KLRF1), NKp44, NKp30, NKp46, CD19, CD4, CD8, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD1 1d, ITGAE, CD103, ITGAL, CD1 1a, LFA-1, ITGAM, CD1 1b, ITGAX, CD1 1c, ITGB1, CD29, ITGB2, CD18, LFA-1, ITGB7, NKG2D, TNFR2, TRANCE/RANKL, DNAM1 (CD226), SLAMF4 (CD244, 2B4), CD84, CD96 (Tactile), CEACAM1, CRT AM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, a ligand that specifically binds with CD83, or any combination thereof; The activating domain can be derived from, e.g., CD3, such as CD3 zeta, epsilon, delta, gamma, or the like. In certain embodiments, the CAR is designed to have two, three, four, or more costimulatory domains. The CAR scFv can be designed to target, for example, CD19, which is a transmembrane protein expressed by cells in the B cell lineage, including all normal B cells and B cell malignances, including but not limited to NHL, CLL, and non-T cell ALL. Example CAR+ T cell therapies and constructs are described in U.S. Patent Publication Nos. 2013/0287748, 2014/0227237, 2014/0099309, and 2014/0050708, and these references are incorporated by reference in their entirety.

A "patient" as used herein includes any human who is afflicted with a cancer (e.g., a lymphoma or a leukemia). The terms "subject" and "patient" are used interchangeably herein. The term "donor subject" refers to herein a subject whose cells are being obtained for further in vitro engineering. The donor subject can be a cancer patient that is to be treated with a population of cells generated by the methods described herein (i.e., an autologous donor), or can be an individual who donates a lymphocyte sample that, upon generation of the population of cells generated by the methods described herein, will be used to treat a different individual or cancer patient (i.e., an allogeneic donor). Those subjects who receive the cells that were prepared by the present methods can be referred to as "recipient subject."

"Stimulation," as used herein, refers to a primary response induced by binding of a stimulatory molecule with its cognate ligand, wherein the binding mediates a signal transduction event. A "stimulatory molecule" is a molecule on a T cell, e.g., the T cell receptor (TCR)/CD3 complex, that specifically binds with a cognate stimulatory ligand present on an antigen present cell. A "stimulatory ligand" is a ligand that when present on an antigen presenting cell (e.g., an artificial antigen presenting cell (aAPC), a dendritic cell, a B-cell, and the like) can specifically bind with a stimulatory molecule on a T cell, thereby mediating a primary response by the T cell, including, but not limited to, activation, initiation of an immune response, proliferation, and the like. Stimulatory ligands include, but are not limited to, an MHC Class I molecule loaded with a peptide, an anti-CD3 antibody, a superagonist anti-CD28 antibody, and a superagonist anti-CD2 antibody. An "activated" or "active," as used herein, refers to a T cell that has been stimulated. An active T cell can be characterized by expression of one or more marker selected form CD137, CD25, CD71, CD26, CD27, CD28, CD30, CD154, CD40L, and CD134.

The term "exogenous" refers to any substance derived from an external source. For example, exogenous IL-7 or exogenous IL-15 can be obtained commercially or produced recombinantly. "Exogenous IL-7" or "exogenous IL-15," when added in or contacted with one or more T cells, indicates that the IL-7 and/or IL-15 are not produced by the T cells. In some embodiments, the T cells prior to being mixed with exogenous IL-7 or IL-15 can contain a trace amount of IL-7 and/or IL-15 that were produced by the T cells or isolated from the subject with the T cells (i.e., endogenous IL-7 or IL-15). The one or more T cells described herein can be contacted with exogenous IL-7 and/or exogenous IL-15 through any means known in the art, including addition of isolated IL-7 and/or IL-15 to the culture, inclusion of IL-7 and/or IL-15 in the culture medium, or expression of IL-7 and/or IL-15 by one or more cells in the culture other than the one or more T cells, such as by a feeder layer.

The term "persistence," as used herein, refers to the ability of, e.g., one or more transplanted T cells administered to a subject or their progenies (e.g., differentiated or matured T cells) to remain in the subject at a detectable level for a period of time. As used herein, increasing the persistence of one or more transplanted T cells or their progenies (e.g., differentiated or matured T cells) refers to increasing the amount of time the transplanted T cells are detectable in a subject after administration. For example, the in vivo persistence of one or more transplanted T cells can be increased by at least about at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, at least about 14 days, at least about 3 weeks, at least about 4 weeks, at least about 1 month, at least about 2 months, at least about 3 months, at least about 4 months, at least about 5 months, or at least about 6 months. In addition, the in vivo persistence of one or more transplanted T cells can be increased by at least about 1.5-fold, at least about 2-fold, at least about 2.5-fold, at least about 3-fold, at least about 3.5-fold, at least about 4-fold, at least about 4.5-fold, at least about 5-fold, at least about 6-fold, at least about 7-fold, at least about 8-fold, at least about 9-fold, or at least about 10-fold compared to the one or more transplanted T cells that were not prepared by the present methods disclosed herein.

The terms "reducing" and "decreasing" are used interchangeably herein and indicate any change that is less than the original. "Reducing" and "decreasing" are relative terms, requiring a comparison between pre- and post-measurements. "Reducing" and "decreasing" include complete depletions. In some embodiments, the terms "reducing" and "decreasing" include a comparison of T cell effects between the T cells prepared by the presently disclosed methods (e.g., contacting with an AKTi and at least one of IL-7 and IL-15) and the T cells without the preparation.

The term "modulating" T cell maturation, as used herein, refers to the use of any intervention described herein to control the maturation, e.g. differentiation, of one or more T cells. In some embodiments, "modulating" refers to delaying or inhibiting T cell maturation. In other embodiments, "modulating" refers to accelerating or promoting T cell maturation. In particular, "delaying or inhibiting T cell maturation," as used here, refers to maintaining one or more T cells in an immature or undifferentiated state. For example, "delaying or inhibiting T cell maturation" can refer to maintaining T cells in a naïve or $T_{CM}$ state, as opposed to progressing to a $T_{EM}$ or $T_{EFF}$ state. "Delaying or inhibiting T cell maturation" can also refer to increasing or enriching the overall percentage of immature or undifferentiated T cells (e.g., naïve T cells and/or $T_{CM}$ cells) within a mixed population of T cells. The state of a T cell (e.g., as mature or immature) can be determined, e.g., by screening for the expression of various genes and the presence of various proteins expressed on the surface of the T cells. For example, the presence of one or more marker selected from the group consisting of L-selectin (CD62L+), IL-7R-α, CD132, CR7, CD45RA, CD45RO, CD27, CD28, CD95, IL-2Rβ, CXCR3, LFA-1, and any combination thereof can be indicative of less mature, undifferentiated T cells.

"Treatment" or "treating" of a subject refers to any type of intervention or process performed on, or the administration of one or more T cells prepared by the present invention to, the subject with the objective of reversing, alleviating, ameliorating, inhibiting, slowing down or preventing the onset, progression, development, severity or recurrence of a symptom, complication or condition, or biochemical indicia associated with a disease. In one embodiment, "treatment" or "treating" includes a partial remission. In another embodiment, "treatment" or "treating" includes a complete remission.

Various aspects of the invention are described in further detail in the following subsections.

Methods of Preparing Immune Cells

The present disclosure relates to methods for preparing immune cells (e.g., lymphocytes or dendritic cells) for use in a cell therapy. It is found that certain in vitro engineered cells (e.g., CAR T cells, TCR cells, or dendritic cells) are not as effective when administered to a patient after the in vitro engineering. Not being bound by any theory, it is noted that one reason can be that lymphocytes can be prematurely differentiated in vitro before being administered to a patient.

The present disclosure, in certain embodiments, sets forth a method to delay, prevent or inhibit premature differentiation of cells in vitro by adding an AKTi and at least one of exogenous IL-7 and exogenous IL-15.

In one embodiment, the present disclosure relates to methods of modulating, e.g., delaying or inhibiting, T cell or DC cell maturation or differentiation in vitro by contacting one or more cells obtained from a donor subject with an AKT inhibitor and at least one of exogenous IL-7 and exogenous IL-15 (or both). Delaying or inhibiting T cell or DC cell maturation or differentiation can increase the percentage of immature, less differentiated cells (e.g., naïve T cells of central memory Tcm cells) in the population of collected T cells or DC cells. Accordingly, the methods described herein can be used to increase the in vivo persistence of transplanted T cells or DC cells or their progenies in a cell therapy (e.g., T cell therapy or DC cell therapy). In addition, the present disclosure provides that the resulting T cells or DC cells exhibit increased expansion in vitro and in vivo and superior anti-tumor activity.

In another embodiment, the invention includes a method for modulating, e.g., delaying or inhibiting, cell (e.g., T cell) maturation or differentiation in vitro for a cell therapy (e.g., T cell therapy), comprising contacting one or more cells (e.g., T cells or DC cells) from a subject in need of a cell therapy (e.g., T cell therapy) with (i) an AKT inhibitor and at least one of exogenous Interleukin-7 (IL-7) and exogenous Interleukin-15 (IL-15), wherein the resulting T cells exhibit delayed maturation or differentiation. The contacting can comprise adding (i) the AKT inhibitor and (ii) exogenous IL-7 and/or exogenous IL-15 directly to the one or more T cells or to the buffer or medium containing the T cells, mixing (i) the AKT inhibitor and (ii) exogenous IL-7 and/or exogenous IL-15 with other components, and/or adding the one or more cells in a medium comprising (i) the AKT inhibitor and (ii) exogenous IL-7 and/or exogenous IL-15. In certain embodiments, the one or more T cells are not contacted with exogenous Interleukin-2 (IL-2). Further preparation of the T cells are described elsewhere herein.

The present disclosure shows that contacting one or more T cells or DC cells in vitro with an AKT inhibitor and at least one of IL-7 and IL-15 can increase the concentration of naïve T cells and $T_{CM}$ cells in a sample, relative to the concentration of more terminally differentiated T cells. Accordingly, in another embodiment, the invention includes a method for generating stem cell-like CD4$^+$ T cells or CD8$^+$ T cells comprising culturing one or more T cells in a medium comprising (i) an AKT inhibitor and (ii) exogenous IL-7, exogenous IL-15, or both. In other embodiments, the invention includes a method of enriching a population of CD8$^-$/CD45RA$^+$/CCR7$^+$ T cells in a sample comprising (a) obtaining one or more T cells from a subject; (b) contacting the one or more T cells with (i) an AKT inhibitor and (ii) exogenous IL-7, exogenous IL-15, or both; and (c) expanding the one or more T cells in the presence of the AKT inhibitor and the exogenous IL-7, exogenous IL-15, or both. Generating an increased concentration of immature and undifferentiated T cells or DC cells can increase the in vivo persistence of the cells upon transplantation to a subject in need of a cell therapy (e.g., T cell therapy or DC cell therapy). Thus, in another embodiment, the invention includes a method for extending the in vivo persistence of one or more T cells or DC cells in an adoptive cell therapy comprising contacting the one or more T cells or DC cells with (i) an AKT inhibitor and (ii) exogenous IL-7, exogenous IL-15, or both prior to administration to a subject; wherein the in vivo persistence is extended relative to one or more transplanted T cells not contacted with an AKT inhibitor and exogenous IL-7, exogenous IL-15, or both.

The methods disclosed herein comprise modulating, e.g., delaying or inhibiting, the maturation or differentiation of one or more T cells or DC cells in vitro. The delay or inhibition of the maturation or differentiation of the one or more T cells or DC cells can be measured by any methods known in the art. For example, the delay or inhibition of the maturation or differentiation of the one or more T cells or DC cells can be measured by detecting the presence of one or biomarker. The presence of the one or more biomarker can be detected by any method known in the art, including, but not limited to, immunohistochemistry and/or fluorescence-activated cells sorting (FACS). In some embodiments, the one or more biomarker is selected from the group consisting of L-selectin (CD62L$^+$), IL-7Rα, CD132, CCR7, CD45RA, CD45RO, CD27, CD28, CD95, IL-2Rβ, CXCR3, LFA-1, or any combination thereof. In certain embodiments, the delay or inhibition of the maturation or differentiation of the one or more T cells or DC cell) can be measured by detecting the presence of one or more of L-selectin (CD62L$^+$), IL-7Rα, and CD132. One of skill in the art would recognize that though the present methods can increase the relative proportion of immature and undifferentiated T cells or DC cells in a population of collected cells, some mature and differentiated cells can still be present. As a result, the delay or inhibition of the maturation or differentiation of the one or more T cells or DC cells can be measured by calculating the total percent of immature and undifferentiated cells in a cell population before and after contacting one or more cells with an AKT inhibitor and at least one of exogenous IL-7 and exogenous IL-15. In some embodiments, the methods disclosed herein increase the percentage of immature and undifferentiated T cells in a T cell population. In certain embodiments, the one or more T cells contacted with an AKT inhibitor and at least one of exogenous IL-7 and exogenous IL-15 comprise at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% immature or undifferentiated T cells. In other embodiments, the one or more T cells or DC cells contacted with an AKT inhibitor and at least one of exogenous IL-7 and exogenous IL-15 comprise at least about 10% to at least about 90%, at least about 20% to at least about 80%, at least about 30% to at least about 70%, at least about 40% to at least about 60%, at least about 10% to at least about 50%, at least about 20% to at least about 40%, at least about 35% to at least about 45%, at least about 20% to at least about 60%, or at least about 50% to at least about 90% immature or undifferentiated T cells or DC cells. In certain embodiments, the immature or undifferentiated T cells are naïve T cells and/or central memory Tcm cells.

The methods disclosed herein comprise contacting one or more T cells or DC cells with an AKT inhibitor and one or more of exogenous IL-7 and exogenous IL-15. In some embodiments, the method comprises contacting one or more T cells or DC cells with an AKT inhibitor, exogenous IL-7, and exogenous IL-15. In another embodiment, the method comprises contacting the one or more T cells or DC cells with an AKT inhibitor and exogenous IL-7. In another embodiment, the method comprises contacting the one or more T cells or DC cells with an AKT inhibitor and exogenous IL-15. In one particular embodiment, the one or more T cells or DC cells are also contacted with exogenous IL-2. In another embodiment, the one or more T cells or DC cells are not contacted with exogenous IL-2.

The one or more T cells or DC cells can be contacted with an AKT inhibitor and exogenous IL-7 and/or IL-15 through any means known in the art. For example, the AKT inhibitor and IL-7/IL-15 can be added to a culture medium used to culture the one or more T cells or DC cells. Alternatively, the AKT inhibitor and IL-7/IL-15 can be produced by one or more cells co-cultured with the one or more T cells or DC cells, e.g., by a feeder cell layer. The AKT inhibitor, IL-7, and IL-15 can be added together or can be added individually. For example, the AKT inhibitor can be added to the culture medium and IL-7 and/or IL-15 can be produced by a cell co-cultured with the one or more T cells.

In addition, the one or more T cells or DC cells can be contacted with the AKT inhibitor and exogenous IL-7 and/or exogenous IL-15 at the same time, at different times, at overlapping times, or sequentially. For example, the one or more T cells or DC cells can be contacted with exogenous IL-7 and/or exogenous IL-15 prior to being contacted with the AKT inhibitor. Alternatively, the one or more T cells or DC cells can be contacted with the AKT inhibitor prior to being contacted with exogenous IL-7 and/or exogenous IL-15. In one particular embodiment, the one or more T cells or DC cells are first contacted with exogenous IL-7 and/or exogenous IL-15 alone and then contacted with the AKT inhibitor and exogenous IL-7 and/or exogenous IL-15 concurrently. In another embodiment, the one or more T cells or DC cells are first contacted with the AKT inhibitor alone and then contacted with the AKT inhibitor and exogenous IL-7 and/or exogenous IL-15 concurrently. In some embodiments the one or more T cells or DC cells are washed to remove the AKT inhibitor, exogenous IL-7, and/or exogenous IL-15.

The one or more T cells or DC cells of the present disclosure can be administered to a subject for use in a T cells or DC cell therapy. Accordingly, the one or more T cells or DC cells can be collected from a subject in need of a T cell therapy or from a donor. Once collected, the one or more T cells can be processed for any suitable period of time before being administered to a subject. During this time, the one or more T cells can be contacted with the AKT inhibitor, exogenous IL-7, and/or exogenous IL-15 for any period of time between the collection of the T cells from the donor and the administration of a subject. For example, the one or more T cells can be contacted with, e.g., cultured in the presence of, the AKT inhibitor, the exogenous IL-7, and/or the exogenous IL-15 for at least about 1 day, at least about 2 days, at least about 3 days, at least about 4 days, at least about 5 days, at least about 6 days, at least about 7 days, at least about 8 days, at least about 9 days, at least about 10 days, at least about 11 days, at least about 12 days, at least about 13 days, or at least about 14 days. In some embodiments, the one or more T cells are contacted with, e.g., cultured in the presence of, the AKT inhibitor, the exogenous IL-7, and/or the exogenous IL-15 for about 1 day to about 14 days, for about 1 day to about 10 days, for about 1 day to about 7 days, from about 1 day to about 6 days, from about 1 day to about 5 days, from about 1 day to about 4 days, from about 1 day to about 3 days, from about 1 day to about 2 days, from about 2 days to about 3 days, from about 2 days to about 4 days, from about 2 days to about 5 days, or from about 2 days to about 6 days. In one particular embodiment, the one or more T cells are contacted with, e.g., cultured in the presence of, the AKT inhibitor, the exogenous IL-7, and/or the exogenous IL-15 from the day the T cells are collected (e.g., day-0) until the day the T cells are administered to a subject. In another embodiment, the T cells are contacted with, e.g., cultured in the presence of, the AKT inhibitor, the exogenous IL-7, and/or the exogenous IL-15 from day 0 to administration, from day 1 to administration, from day 2 to administration, from day 3 to administration from day 4 to administration, from day 5 to administration, or from day 6 to administration. In some embodiments, the one or more T cells are washed prior to administration to remove the AKT inhibitor, exogenous IL-7, and/or exogenous IL-15.

In certain embodiments, the present disclosure is directed to a method of modulating, e.g., delaying or inhibiting, T cell or DC cell maturation or differentiation in vitro by contacting one or more T cells or DC cells obtained from a donor subject with an AKT inhibitor and at least one of exogenous IL-7 and exogenous IL-15 (or both), wherein the one or more cells are not contacted with exogenous IL-2. In one embodiment, the one or more cells treated with AKTi and at least one of IL-7 and IL-15 (or both), but without IL-2, exhibit delayed or inhibited maturation or differentiation higher than the one or more cells treated with IL-2 alone or IL-2 and AKTi. The one or more T cells or DC cells can show an increased percentage of immature, less differentiated cells (e.g., naïve T cells of central memory Tcm cells) compared to the one or more T cells or DC cells that are treated with IL-2 alone or IL-2 and AKTi. Accordingly, the methods described herein can be used to increase the in vivo persistence of transplanted T cells or DC cells or their progenies in a cell therapy (e.g., T cell therapy or DC cell therapy). In addition, the present disclosure provides that the resulting T cells or DC cells exhibit increased expansion in vitro and in vivo and superior anti-tumor activity. In some embodiments, the one or more T cells are CD4 cells. In other embodiments, the one or more T cells are CD8 cells. In particular embodiments, the contacting with an AKTi and at least one of IL-7 and IL-15 is performed for at least 1, at least about 2, at least about 3, at least about 4, at least about 5, at least about 6, at least about 7, at least about 8, at least about 9, at least about 10, at least about 11, at least about 12, or about 13 days. In other embodiments, the contacting with an AKTi and at least one of IL-7 and IL-15 is performed more than one day to less than 14 days, less than 13 days, less than 12 days, less than 11 days, less than 10 days, less than 9 days, or less than 8 days.

The methods described herein can further comprise enriching a population of lymphocytes obtained from a donor. Enrichment of a population of lymphocytes, e.g., the one or more T cells, can be accomplished by any suitable separation method including, but not limited to, the use of a separation medium (e.g., FICOLL-PAQUE™, ROSET-TESEP™ HLA Total Lymphocyte enrichment cocktail, Lymphocyte Separation Medium (LSA) (MP Biomedical Cat. No. 0850494X), or the like), cell size, shape or density separation by filtration or elutriation, immunomagnetic separation (e.g., magnetic-activated cell sorting system, MACS), fluorescent separation (e.g., fluorescence activated cell sorting system, FACS), or bead based column separation.

The methods described herein can further comprise stimulating the population of lymphocytes with one or more T-cell stimulating agents to produce a population of activated T cells under a suitable condition. Any combination of one or more suitable T-cell stimulating agents can be used to produce a population of activated T cells including, including, but not limited to, an antibody or functional fragment thereof which targets a T-cell stimulatory or co-stimulatory molecule (e.g., anti-CD2 antibody, anti-CD3 antibody, anti-CD28 antibody, or a functional fragment thereof), or any other suitable mitogen (e.g., tetradecanoyl phorbol acetate (TPA), phytohaemagglutinin (PHA), concanavalin A (conA), lipopolysaccharide (LPS), pokeweed mitogen (PWM)), or a natural ligand to a T-cell stimulatory or co-stimulatory molecule.

The suitable condition for stimulating the population of lymphocytes as described herein can include a temperature, for an amount of time, and/or in the presence of a level of $CO_2$. In certain embodiments, the temperature for stimulation is about 34° C., about 35° C., about 36° C., about 37° C., or about 38° C. In certain embodiments, the temperature for stimulation is about 34-38° C. In certain embodiments, the temperature for stimulation is from about 35-37° C. In certain embodiments, the temperature for stimulation is from about 36-38° C. In certain embodiments, the temperature for stimulation is about 36-37° C. or about 37° C.

Another condition for stimulating the population of lymphocytes as described herein can include a time for stimulation. In some embodiments, the time for stimulation is about 24-72 hours. In some embodiments, the time for stimulation is about 24-36 hours, about 30-42 hours, about 36-48 hours, about 40-52 hours, about 42-54 hours, about 44-56 hours, about 46-58 hours, about 48-60 hours, about 54-66 hours, or about 60-72 hours. In one particular embodiment, the time for stimulation is about 48 hours or at least about 48 hours. In other embodiments, the time for stimulation is about 44-52 hours. In certain embodiments, the time for stimulation is about 40-44 hours, about 40-48 hours, about 40-52 hours, or about 40-56 hours.

Other conditions for stimulating the population of lymphocytes as described herein can include a $CO_2$ Level. In some embodiments, the level of $CO_2$ for stimulation is about 1.0-10% $CO_2$. In some embodiments, the level of $CO_2$ for stimulation is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ for stimulation is about 3-7% $CO_2$. In other embodiments, the level of $CO_2$ for stimulation is about 4-6% $CO_2$. In still other embodiments, the level of $CO_2$ for stimulation is about 4.5-5.5% $CO_2$. In one particular embodiment, the level of $CO_2$ for stimulation is about 5% $CO_2$.

The conditions for stimulating the population of lymphocytes can comprise a temperature, for an amount of time for stimulation, and/or in the presence of a level of $CO_2$ in any combination. For example, the step of stimulating the population of lymphocytes can comprise stimulating the population of lymphocytes with one or more T-cell stimulating agents at a temperature of about 36-38° C., for an amount of time of about 44-52 hours, and in the presence of a level of $CO_2$ of about 4.5-5.5% $CO_2$.

The concentration of lymphocytes useful for the methods herein is about $1.0$-$10.0 \times 10^6$ cells/mL. In certain embodiments, the concentration of lymphocytes is about $1.0$-$2.0 \times 10^6$ cells/mL, about $1.0$-$3.0 \times 10^6$ cells/mL, about $1.0$-$4.0 \times 10^6$ cells/mL, about $1.0$-$5.0 \times 10^6$ cells/mL, about $1.0$-$6.0 \times 10^6$ cells/mL, about $1.0$-$7.0 \times 10^6$ cells/mL, about $1.0$-$8.0 \times 10^6$ cells/mL, $1.0$-$9.0 \times 10^6$ cells/mL, or about $1.0$-$10.0 \times 10^6$ cells/mL. In certain embodiments, the concentration of lymphocytes is about $1.0$-$2.0 \times 10^6$ cells/mL. In certain embodiments, the concentration of lymphocytes is about $1.0$-$1.2 \times 10^6$ cells/mL, about $1.0$-$1.4 \times 10^6$ cells/mL, about $1.0$-$1.6 \times 10^6$ cells/mL, about $1.0$-$1.8 \times 10^6$ cells/mL, or about $1.0$-$2.0 \times 10^6$ cells/mL. In certain embodiments, the concentration of lymphocytes is at least about $1.0 \times 10^6$ cells/mL, at least about $1.1 \times 10^6$ cells/mL, at least about $1.2 \times 10^6$ cells/mL, at least about $1.3 \times 10^6$ cells/mL, at least about $1.4 \times 10^6$ cells/mL, at least about $1.5 \times 10^6$ cells/mL, at least about $1.6 \times 10^6$ cells/mL, at least about $1.7 \times 10^6$ cells/mL, at least about $1.8 \times 10^6$ cells/mL, at least about $1.9 \times 10^6$ cells/mL, at least about $2.0 \times 10^6$ cells/mL, at least about $4.0 \times 10^6$ cells/mL, at least about $6.0 \times 10^6$ cells/mL, at least about $8.0 \times 10^6$ cells/mL, or at least about $10.0 \times 10^6$ cells/mL.

An anti-CD3 antibody (or functional fragment thereof), an anti-CD28 antibody (or functional fragment thereof), or a combination of anti-CD3 and anti-CD28 antibodies can be used in accordance with the step of stimulating the population of lymphocytes. Any soluble or immobilized anti-CD2, anti-CD3 and/or anti-CD28 antibody or functional fragment thereof can be used (e.g., clone OKT3 (anti-CD3), clone 145-2C11 (anti-CD3), clone UCHT1 (anti-CD3), clone L293 (anti-CD28), clone 15E8 (anti-CD28)). In some aspects, the antibodies can be purchased commercially from vendors known in the art including, but not limited to, Miltenyi Biotec, BD Biosciences (e.g., MACS GMP CD3 pure 1 mg/mL, Part No. 170-076-116), and eBioscience, Inc. Further, one skilled in the art would understand how to produce an anti-CD3 and/or anti-CD28 antibody by standard methods. In some embodiments, the one or more T cell stimulating agents that are used in accordance with the step of stimulating the population of lymphocytes include an antibody or functional fragment thereof which targets a T-cell stimulatory or co-stimulatory molecule in the presence of a T cell cytokine. In one aspect, the one or more T cell stimulating agents include an anti-CD3 antibody and IL-2. In certain embodiments, the T cell stimulating agent includes an anti-CD3 antibody at a concentration of from about 20 ng/mL-100 ng/mL. In certain embodiments, the concentration of anti-CD3 antibody is about 20 ng/mL, about 30 ng/mL, about 40 ng/mL, about 50 ng/mL, about 60 ng/mL, about 70 ng/mL, about 80 ng/mL, about 90 ng/mL, or about 100 ng/mL. In one particular embodiment, the concentration of anti-CD3 antibody is about 50 ng/mL. In an alternative embodiment, T cell activation is not needed. In such embodiment, the step of stimulating the population of lymphocytes to produce a population of activated T cells is omitted from the method, and the population of lymphocytes, which can be enriched for T lymphocytes, is transduced in accordance with the steps below.

The methods described herein can comprise transducing the population of activated T cells with a viral vector comprising a nucleic acid molecule which encodes the cell surface receptor, using a single cycle transduction to produce a population of transduced T cells. Several recombinant viruses have been used as viral vectors to deliver genetic material to a cell. Viral vectors that can be used in accordance with the transduction step can be any ecotropic or amphotropic viral vector including, but not limited to, recombinant retroviral vectors, recombinant lentiviral vectors, recombinant adenoviral vectors, and recombinant adeno-associated viral (AAV) vectors. In some embodiments, the method further comprises transducing the one or more T cells with a retrovirus. In one embodiment, the viral vector used to transduce the population of activated T cells is an MSGV1 gamma retroviral vector. In certain embodiments, the viral vector used to transduce the population of activated T cells is the PG13-CD19-H3 Vector described by Kochenderfer, *J. Immunother.* 32(7): 689-702 (2009). According to one aspect of this embodiment, the viral vector is grown in a suspension culture in a medium which is specific for viral vector manufacturing referred to herein as a "viral vector inoculum." Any suitable growth media and/or supplements for growing viral vectors can be used in the viral vector inoculum in accordance with the methods described herein. According to some aspects, the viral vector inoculum is then be added to the serum-free culture media described below during the transduction step.

In some embodiments, the one or more T cells can be transduced with a retrovirus. In one embodiment, the retrovirus comprises a heterologous gene encoding a cell surface receptor. In one particular embodiment, the cell surface receptor is capable of binding an antigen on the surface of a target cell, e.g., on the surface of a tumor cell.

The conditions for transducing the population of activated T cells as described herein can comprise a specific time, at a specific temperature and/or in the presence of a specific level of $CO_2$. In certain embodiments, the temperature for transduction is about 34° C., about 35° C., about 36° C., about 37° C., or about 38° C. In one embodiment, the temperature for transduction is about 34-38° C. In another embodiment, the temperature for transduction is from about 35-37° C. In another embodiment, the temperature for transduction is from about 36-38° C. In still another embodiment, the temperature for transduction is about 36-37° C. In one particular embodiment, the temperature for transduction is about 37° C.

In certain embodiments, the time for transduction is about 12-36 hours. In some embodiments, the time for transduction is about 12-16 hours, about 12-20 hours, about 12-24 hours, about 12-28 hours, or about 12-32 hours. In other embodiments, the time for transduction is about 20 hours or at least about 20 hours. In one embodiment, the time for transduction is about 16-24 hours. In other embodiments, the time for transduction is at least about 14 hours, at least about 16 hours, at least about 18 hours, at least about 20 hours, at least about 22 hours, at least about 24 hours, or at least about 26 hours.

In certain embodiments, the level of $CO_2$ for transduction is about 1.0-10% $CO_2$. In other embodiments, the level of $CO_2$ for transduction is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ for transduction is about 3-7% $CO_2$. In another embodiment, the level of $CO_2$ for transduction can be about 4-6% $CO_2$. In another embodiment, the level of $CO_2$ for transduction is about 4.5-5.5% $CO_2$. In one particular embodiment, the level of $CO_2$ for transduction is about 5% $CO_2$.

In some embodiments, transducing the population of activated T cells as described herein can be performed for a particular time, at a specific temperature and/or in the presence of a specific level of $CO_2$ in any combination: a temperature of about 36-38° C., for an amount of time of about 16-24 hours, and in the presence of a level of $CO_2$ of about 4.5-5.5% $CO_2$.

The methods described herein can comprise expanding the population of transduced one or more T cells for a particular time to produce a population of engineered T cells. The predetermined time for expansion can be any suitable time which allows for the production of (i) a sufficient number of cells in the population of engineered T cells for at least one dose for administering to a patient, (ii) a population of engineered T cells with a favorable proportion of juvenile cells compared to a typical longer process, or (iii) both (i) and (ii). This time will depend on the cell surface receptor expressed by the T cells, the vector used, the dose that is needed to have a therapeutic effect, and other variables. Thus, in some embodiments, the predetermined time for expansion can be 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, or more than 21 days. In some aspects, the time for expansion is shorter than expansion methods known in the art. For example, the predetermined time for expansion can be shorter by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, or can be shorter by more than 75%. In one aspect, the time for expansion is about 3 days, and the time from enrichment of the population of lymphocytes to producing the engineered T cells is about 6 days.

The conditions for expanding the population of transduced T cells can include a temperature and/or in the presence of a level of $CO_2$. In certain embodiments, the temperature is about 34° C., about 35° C., about 36° C., about 37° C., or about 38° C. In one embodiment, the temperature is about 34-38° C. In another embodiment, the temperature is from about 35-37° C. In another embodiment, the temperature is from about 36-38° C. In yet another embodiment, the temperature is about 36-37° C. In one particular embodiment the temperature is about 37° C. In certain embodiments, the level of $CO_2$ is 1.0-10% $CO_2$. In other embodiments, the level of $CO_2$ is about 1.0%, about 2.0%, about 3.0%, about 4.0%, about 5.0%, about 6.0%, about 7.0%, about 8.0%, about 9.0%, or about 10.0% $CO_2$. In one embodiment, the level of $CO_2$ is about 4.5-5.5% $CO_2$. In another embodiment, the level of $CO_2$ is about 5% $CO_2$. In other embodiments, the level of $CO_2$ is about 3.5%, about 4.0%, about 4.5%, about 5.0%, about 5.5%, or about 6.5% $CO_2$. In some embodiments, the conditions for expanding the population of transduced T cells include a temperature and/or in the presence of a level of $CO_2$ in any combination. For example, conditions for expanding the population of transduced T cells comprise a temperature of about 36-38° C. and in the presence of a level of $CO_2$ of about 4.5-5.5% $CO_2$.

Each step of the methods described herein can be performed in a closed system. In certain embodiments, the closed system is a closed bag culture system, using any suitable cell culture bags (e.g., Miltenyi Biotec MACS® GMP Cell Differentiation Bags, Origen Biomedical PermaLife Cell Culture bags). In some embodiments, the cell culture bags used in the closed bag culture system are coated with a recombinant human fibronectin fragment during the transduction step. The recombinant human fibronectin fragment can include three functional domains: a central cell-binding domain, heparin-binding domain II, and a CS1-sequence. The recombinant human fibronectin fragment can be used to increase gene efficiency of retroviral transduction of immune cells by aiding co-localization of target cells and viral vector. In certain embodiments, the recombinant human fibronectin fragment is RETRONECTIN® (Takara Bio, Japan). In certain embodiments, the cell culture bags are coated with recombinant human fibronectin fragment at a concentration of about 1-60 µg/mL or about 1-40 µg/mL. In other embodiments, the cell culture bags are coated with recombinant human fibronectin fragment at a concentration of about 1-20 µg/mL, 20-40 µg/mL, or 40-60 µg/mL. In some embodiments, the cell culture bags are coated with about 1 µg/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 11 µg/mL, about 12 µg/mL, about 13 µg/mL, about 14 µg/mL, about 15 µg/mL, about 16 µg/mL, about 17 µg/mL, about 18 µg/mL, about 19 µg/mL, or about 20 µg/mL recombinant human fibronectin fragment. In other embodiments, the cell culture bags are coated with about 2-5 μg/mL, about 2-10 μg/mL, about 2-20 μg/mL, about 2-25 μg/mL, about 2-30 μg/mL, about 2-35 μg/mL, about 2-40 μg/mL, about 2-50 μg/mL, or about 2-60 μg/mL recombinant human fibronectin fragment. In certain embodiments, the cell culture bags are coated with at least about 2 μg/mL, at least about 5 μg/mL, at least about 10 μg/mL, at least about 15 μg/mL, at least about 20 μg/mL, at least about 25 μg/mL, at least about 30 μg/mL, at least about 40 μg/mL, at least about 50 μg/mL, or at least about 60 μg/mL recombinant human fibronectin fragment. In one particular embodiment, the cell culture bags are coated with at least about 10 μg/mL recombinant human fibronectin fragment. The cell culture bags used in the closed bag culture system can optionally be blocked with human albumin serum (HSA) during the transduction step. In an alternative embodiment, the cell culture bags are not blocked with HSA during the transduction step.

In other aspects, at least one of (a) contacting the population of lymphocytes with an AKT inhibitor and at least one of exogenous IL-7 and exogenous IL-15, (b) stimulating the population of lymphocytes, (c) transducing the population of activated T cells, and (d) expanding the population of transduced T cells is performed using a serum-free culture medium which is free from added serum. In some aspect, each of (a) to (d) is performed using a serum-free culture medium which is free from added serum. In another aspect, at least one of (a) contacting the population of lymphocytes with an AKT inhibitor and at least one of exogenous IL-7 and exogenous IL-15, (b) stimulating the population of lymphocytes, (c) transducing the population of activated T cells, and (d) expanding the population of transduced T cells is performed using a serum-free culture medium. In some aspect, each of (a) to (d) is performed using a serum-free culture medium which is free from added serum. As referred to herein, the term "serum-free media" or "serum-free culture medium" means that the growth media used is not supplemented with serum (e.g., human serum or bovine serum). In other words, in some embodiments, no serum is added to the culture medium as an individually separate and distinct ingredient for the purpose of supporting the viability, activation and grown of the cultured cells. Any suitable culture medium T cell growth media can be used for culturing the cells in suspension in accordance with the methods described herein. For example a T cell growth media can include, but is not limited to, a sterile, low glucose solution that includes a suitable amount of buffer, magnesium, calcium, sodium pyruvate, and sodium bicarbonate. In one embodiment, the T cell growth media is OPTMIZER™ (Life Technologies). In contrast to typical methods for producing engineered T cells, the methods described herein can use culture medium that is not supplemented with serum (e.g., human or bovine).

AKT Inhibitors

The AKT kinase family has three highly homologous isoforms: AKT1 (PKBα), AKT2 (PKBβ), and AKT3 (PKBγ), each with unique and overlapping functions. As part of the PI3K-AKT-mTOR signaling pathway, AKT acts downstream of PI3K to activate mTOR, eliciting a variety of responses in the cell including survival, growth, proliferation, migration, and metabolism.

Any AKT inhibitor known in the art can be used in the present invention, including any inhibitor of AKT1, AKT2, AKT3, or any combination thereof. For the AKT inhibitor can be selected from A6730, B2311, 124018, GSK2110183 (afuresertib), Perifosine (KRX-0401), GDC-0068 (ipatasertib), RX-0201, VQD-002, LY294002, A-443654, A-674563, Akti-1, Akti-2, Akti-1/2, AR-42, API-59CJ-OMe, ATI-13148, AZD-5363, erucylphosphocholine, GSK-2141795 (GSK795), KP372-1, L-418, NL-71-101, PBI-05204, PIA5, PX-316, SR13668, triciribine, GSK 690693 (CAS #937174-76-0), FPA 124 (CAS #902779-59-3), Miltefosine, PHT-427 (CAS #1 191951-57-1), 10-DEBC hydrochloride, Akt inhibitor III, Akt inhibitor VIII, MK-2206 dihydrochloride (CAS #1032350-13-2), SC79, AT7867 (CAS #857531-00-1), CCT128930 (CAS #885499-61-6), A-674563 (CAS #552325-73-2), AGL 2263, AS-041 164 (5-benzo[1,3]dioxol-5-ylmethylene-thiazolidine-2,4-dione), BML-257 (CAS #32387-96-5), XL-418, CAS #612847-09-3, CAS #98510-80-6, H-89 (CAS #127243-85-0), OXY-1 1 1 A, 3-[1-[[4-(7-phenyl-3H-imidazo[4,5-g]quinoxalin-6-yl)phenyl]methyl]piperidin-4-yl]-1H-benzimidazol-2-one, and any combination thereof. The AKT inhibitor can also be selected from 1-{1-[4-(7-phenyl-1H-imidazo[4,5-g]quinoxalin-6-yl)benzyl]piperidin-4-yl}-1,3-dihydro-2H-benzimidazol-2-one; N,N-dimethyl-1-[4-(6-phenyl-1H-imidazo[4,5-g]quinoxalin-7-yl)phenyl]metha-namine; 1-{1-[4-(3-phenylbenzo[g]quinoxalin-2-yl)benzyl]piperidin-4-yl}-1,-3-dihydro-2H-benzimidazol-2-one; 1-{1-[4-(7-phenyl-1H-imidazo[4,5-g]quinoxalin-6-yl)benzyl]piperidin-4-yl}-1,3-dihydro-2H-benzimidazol-2-one; N,N-dimethyl-1-[4-(6-phenyl-1H-imidazo[4,5-g]quinoxalin-7-yl)phenyl]metha-namine; 1-{1-[4-(3-phenylbenzo[g]quinoxalin-2-yl)benzyl]piperidin-4-yl}-1,-3-dihydro-2H-benzimidazol-2-one (also called as 3-[1-[[4-(7-phenyl-3H-imidazo[4,5-g]quinoxalin-6-yl)phenyl]methyl]piperidin-4-yl]-1H-benzimidazol-2-one); a compound having a structure comprising Formula I, Formula II, Formula III, Formula IV, Formula V, Formula VI, Formula VII, and Formula VIII disclosed in U.S. Pat. No. 7,273,869, published Sep. 25, 2007, which is incorporated herein by reference in its entirety; a stereoisomer thereof; any AKTi disclosed in U.S. Pat. No. 7,273,869, published Sep. 25, 2007, which is incorporated herein by reference in its entirety; and any combination thereof. In one example, the AKTi comprises formula I.

In one particular embodiment, the AKT inhibitor is 3-[1-[[4-(7-phenyl-3H-imidazo[4,5-g]quinoxalin-6-yl)phenyl]methyl]piperidin-4-yl]-1H-benzimidazol-2-one. In another embodiment, the AKT inhibitor is Akt inhibitor VIII.

In some embodiments, the AKT comprises a formula illustrated by the Formula I:

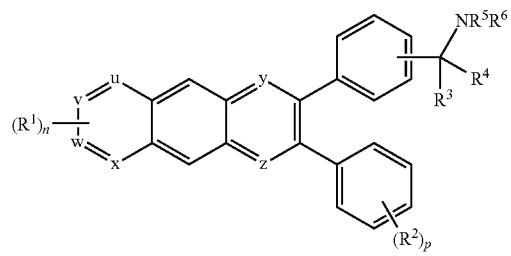

wherein: a is 0 or 1; b is 0 or 1; m is 0, 1 or 2; n is 0, 1 or 2; p is 0, 1, 2 or 3; r is 0 or 1; s is 0 or 1; t is 2, 3, 4, 5 or 6; u, v and x are independently selected from: CH and N; w is selected from a bond, CH and N; y and z are independently selected from: CH and N, provided that at least one of y and z is N; $R^1$ is independently selected from: 1) $(C=O)_aO_bC_1-C_{10}$ alkyl, 2) $(C=O)_aO_b$aryl, 3) $C_2-C_{10}$ alkenyl, 4) $C_2-C_{10}$ alkynyl, 5) $(C=O)_aO_b$ heterocyclyl, 6) $(C=O)_aO_bC_3-C_8$ cycloalkyl, 7) $CO_2H$, 8) halo, 9) CN, 10) OH, 11) $O_bC_1-C_6$ perfluoroalkyl, 12) $O_a(C=O)_bNR^7R^8$, 13)

$NR^c(C=O)NR7R^8$, 14) $S(O)_mR^a$, 15) $S(O)_2NR^7R^8$, 16) $NWS(O)_mR^a$, 17) oxo, 18) CHO, 19) $NO_2$, 20) $NR^c(C=O)O_bR^a$, 21) $O(C=O)O_bC_1$-$C_{10}$ alkyl, 22) $O(C=O)O_bC_3$-$C_8$ cycloalkyl, 23) $O(C=O)O_b$aryl, and 24) $O(C=O)O_b$-heterocycle; said alkyl, aryl, alkenyl, alkynyl, heterocyclyl, and cycloalkyl optionally substituted with one or more substituents selected from $R^z$; $R^2$ is independently selected from: 1) $(C=O)_aO_bC_1$-$C_{10}$ alkyl, 2) $(C=O)_aO_a$aryl, 3) $C_2$-$C_{10}$ alkenyl, 4) $C_2$-$C_{10}$ alkynyl, 5) $(C=O)_aO_b$ heterocyclyl, 6) $(C=O)_aO_bC_3$-$C_8$ cycloalkyl, 7) $CO_2H$, 8) halo, 9) CN, 10) OH, 11) $O_bC_1$-$C_6$ perfluoroalkyl, 12) $O_a(C=O)_bNR^7R^8$, 13) $NR^c(C=O)NR7R^8$, 14) $S(O)_mR^a$, 15) $S(O)_2NR^7R^8$, 16) $NR^cS(O)_mR^a$, 17) CHO, 18) $NO_2$, 19) $NR^c(C=O)O_bR^a$, 20) $O(C=O)O_bC_1$-$C_{10}$ alkyl, 21) $O(C=O)O_bC_3$-$C_8$ cycloalkyl, 22) $O(C=O)O_b$aryl, and 23) $O(C=O)O_b$-heterocycle; said alkyl, aryl, alkenyl, alkynyl, heterocyclyl, and cycloalkyl optionally substituted with one, two or three substituents selected from $R^z$; $R^3$ and $R^4$ are independently selected from: H, $C_1$-$C_6$-alkyl and $C_1$-$C_6$-perfluoroalkyl, or $R^3$ and $R^4$ are combined to form —$(CH_2)_t$— wherein one of the carbon atoms is optionally replaced by a moiety selected from O, $S(O)_m$, —$N(R^b)C(O)$—, and —$N(COR^a)$—; $R^5$ and $R^6$ are independently selected from: 1) H, 2) $(C=O)O_bR^a$, 3) $C_1$-$C_{10}$ alkyl, 4) aryl, 5) $C_2$-$C_{10}$ alkenyl, 6) $C_2$-$C_{10}$ alkynyl, 7) heterocyclyl, 8) $C_3$-$C_8$ cycloalkyl, 9) $SO_2R^a$, and 10) $(C=O)NR^b_2$, said alkyl, cycloalkyl, aryl, heterocyclyl, alkenyl, and alkynyl is optionally substituted with one or more substituents selected from $R^z$, or $R^5$ and $R^6$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with Q and also optionally substituted with one or more substituents selected from $R^z$; Q is selected from: —$NR^7R^8$, aryl and heterocyclyl, said aryl and heterocyclyl optionally substituted with one to three substituents selected from $R^z$; $R^7$ and $R^8$ are independently selected from: 1) H, 2) $(C=O)O_bC_1$-$C_{10}$ alkyl, 3) $(C=O)O_bC_3$-$C_8$ cycloalkyl, 4) $(C=O)O_b$aryl, 5) $(C=O)O_b$heterocyclyl, 6) $C_1$-$C_{10}$ alkyl, 7) aryl, 8) $C_2$-$C_{10}$ alkenyl, 9) $C_2$-$C_{10}$ alkynyl, 10) heterocyclyl, 11) $C_3$-$C_8$ cycloalkyl, 12) $SO_2R^a$, and 13) $(C=O)NR^b_2$; said alkyl, cycloalkyl, aryl, heterocylyl, alkenyl, and alkynyl is optionally substituted with one or more substituents selected from $R^z$, or $R^7$ and $R^8$ can be taken together with the nitrogen to which they are attached to form a monocyclic or bicyclic heterocycle with 5-7 members in each ring and optionally containing, in addition to the nitrogen, one or two additional heteroatoms selected from N, O and S, said monocyclic or bicyclic heterocycle optionally substituted with one or more substituents selected from $R^z$; $R^z$ is selected from: 1) $(C=O)_rO_s(C_1$-$C_{10})$alkyl, 2) $O_r(C_1$-$C_3)$perfluoroalkyl, 3) $(C_0$-$C_6)$alkylene-$S(O)_mR^a$, 4) oxo, 5) OH, 6) halo, 7) CN, 8) $(C=O)_rO_s(C_2$-$C_{10})$alkenyl, 9) $(C=O)_rO_s(C_2$-$C_{10})$alkynyl, 10) $(C=O)_rO_s(C_3$-$C_6)$cycloalkyl, 11) $(C=O)_rO_s(C_0$-$C_6)$alkylene-aryl, 12) $(C=O)_rO_s(C_0$-$C_6)$alkylene-heterocyclyl, 13) $(C=O)_rO_s(C_0$-$C_6)$alkylene-$N(R^b)_2$, 14) $C(O)R^a$, 15) $(C_0$-$C_6)$alkylene-$CO_2R^a$, 16) C(O)H, 17) $(C_0$-$C_6)$alkylene-$CO_2H$, 18) $C(O)N(R^b)_2$, 19) $S(O)_mR^a$, 20) $S(O)_2N(R^b)_2$, 21) $NR^c(C=O)O_bR^a$, 22) $O(C=O)O_bC_1$-$C_{10}$ alkyl, 23) $O(C=O)O_bC_3$-$C_8$ cycloalkyl, 24) $O(C=O)O_b$aryl, and 25) $O(C=O)O_b$-heterocycle; said alkyl, alkenyl, alkynyl, cycloalkyl, aryl, and heterocyclyl is optionally substituted with up to three substituents selected from $R^b$, OH, $(C_1$-$C_6)$alkoxy, halogen, $CO_2H$, CN, $O(C=O)$ $C_1$-$C_6$ alkyl, oxo, and $N(R^b)_2$; $R^a$ is substituted or unsubstituted $(C_1$-$C_6)$alkyl, substituted or unsubstituted $(C_2$-$C_6)$alkenyl, substituted or unsubstituted $(C_2$-$C_6)$alkynyl, substituted or unsubstituted $(C_3$-$C_6)$cycloalkyl, substituted or unsubstituted aryl, $(C_1$-$C_6)$perfluoroalkyl, 2,2,2-trifluoroethyl, or substituted or unsubstituted heterocyclyl; and $R^b$ is H, $(C_1$-$C_6)$alkyl, substituted or unsubstituted aryl, substituted or unsubstituted benzyl, substituted or unsubstituted heterocyclyl, $(C_3$-$C_6)$cycloalkyl, $(C=O)OC_1$-$C_6$ alkyl, $(C=O)C_1$-$C_6$ alkyl or $S(O)_2R^a$; $R^c$ is selected from: 1) H, 2) $C_1$-$C_{10}$ alkyl, 3) aryl, 4) $C_2$-$C_{10}$ alkenyl, 5) $C_2$-$C_{10}$ alkynyl, 6) heterocyclyl, 7) $C_3$-$C_8$ cycloalkyl, 8) $C_1$-$C_6$ perfluoroalkyl, said alkyl, cycloalkyl, aryl, heterocylyl, alkenyl, and alkynyl is optionally substituted with one or more substituents selected from $R^z$; or a pharmaceutically acceptable salt or a stereoisomer thereof.

In certain embodiments, the AKT signaling can be inhibited directly, e.g., by a molecule that binds AKT, or indirectly, e.g., by interfering with another member of the PI3K-AKT-mTOR signaling pathway. Accordingly, the AKT inhibitor can be a molecule which inhibits the activity of one or more members of the PI3K-AKT-mTOR signaling pathway. For example, the one or more T cells can be contacted with an AKT inhibitor, a PI3K inhibitor, an mTOR inhibitor, or an any combination thereof.

The amount of the AKT inhibitor useful for the methods described herein can be an amount that is capable of reducing or inhibiting the activity of AKT in the one or more T cells (i.e., effective amount). In another embodiment, the amount of the AKT inhibitor useful for the invention can be an amount that is capable of delaying or inhibiting maturation or differentiation of T cells or DC cells in vitro in combination with exogenous IL-7 and/or exogenous IL-15. Accordingly, in one embodiment, the one or more T cells can be contacted with an AKT inhibitor, e.g., 3-[1-[[4-(7-phenyl-3H-imidazo[4,5-g]quinoxalin-6-yl)phenyl]methyl]piperidin-4-yl]-1H-benzimidazol-2-one, at a concentration of at least about 1 nM, at least about 10 nM, at least about 50 nM, at least about 100 nM, at least about 200 nM, at least about 300 nM, at least about 400 nM, at least about 500 nM, at least about 1 μM, at least about 2 μM, at least about 3 μM, at least about 4 μM, at least about 5 μM, at least about 6 μM, at least about 7 μM, at least about 8 μM, at least about 9 μM, at least about 10 μM, at least about 11 μM, at least about 12 μM, at least about 13 μM, at least about 14 μM, at least about 15 μM, at least about 16 μM, at least about 17 μM, at least about 18 μM, at least about 19 μM, at least about 20 μM, at least about 25 μM, at least about 30 μM, at least about 35 μM, at least about 40 μM, at least about 45 μM, at least about 50 μM, at least about 60 μM, at least about 70 μM, at least about 80 μM, at least about 90 μM, at least about 100 μM, at least about 200 μM, at least about 300 μM, at least about 400 μM, at least about 500 μM, or at least about 1 mM. In another embodiment, the one or more T cells can be contacted with an AKT inhibitor, e.g., 3-[1-[[4-(7-phenyl-3H-imidazo[4,5-g]quinoxalin-6-yl)phenyl]methyl]piperidin-4-yl]-1H-benzimidazol-2-one, at a concentration of from about 1 nM to about 1 mM, from about 10 nM to about 1 mM, from about 100 nM to about 1 mM, from about 1 μM to about 1 mM, from about 10 μM to about 1 mM, from about 100 μM to about 1 mM, from about 1 nM to about 100 μM, from about 1 nM to about 10 μM, from about 1 nM to about 1 μM, from about 1 nM to about 100 nM, from about 1 nM to about 50 nM, from about 100 nM to about 100 μM, from about 500 nM to about 50 μM, from about 1 μM to about 50 μM, from about 1 μM to about 10 μM, or from about 5 μM to about 10 μM.

Any reduction of AKT activity can be achieved according to the present methods. For example, AKT activity can be reduced or inhibited by an AKT inhibitor by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, or about 100%.

Exogenous IL-7 and Exogenous IL-15

Interleukin-7 (IL-7) is a cytokine that promotes lymphocyte homeostasis and is necessary for T cell development. Endogenous IL-7 is produced by epithelial cells in the thymus and bone marrow, and its receptor, IL-7 receptor-α (IL-7R-α) is expressed by a subset of T cells, including naïve T cells and $T_{CM}$ cells. IL-7 signaling occurs various tyrosine kinases, including the Janus kinase/signal transducer and activator of transcription (Jak/STAT) pathway, PI3K, and Src family tyrosine kinases.

Any exogenous IL-7 can be used in the methods described herein. In some embodiments, the exogenous IL-7 is human IL-7. In some embodiments, the exogenous IL-7 is wild-type IL-7. In other embodiments, the exogenous IL-7 is recombinant IL-7. The IL-7 can be produced and obtained by any methods known in the art, including but not limited to isolated IL-7 from one more IL-7 producing cells or obtaining a commercially available IL-7.

Any concentration of IL-7 can be used in the methods described herein. For example, the present method can include contacting the one or more T cells with at least about 0.001 ng/ml IL-7, at least about 0.005 ng/ml IL-7, at least about 0.01 ng/ml IL-7, at least about 0.05 ng/ml IL-7, at least about 0.1 ng/ml IL-7, at least about 0.5 ng/ml IL-7, at least about 1.0 ng/ml IL-7, at least about 1 ng/ml IL-7, at least about 2 ng/ml IL-7, at least about 3 ng/ml IL-7, at least about 4 ng/ml IL-7, at least about 5 ng/ml IL-7, at least about 6 ng/ml IL-7, at least about 7 ng/ml IL-7, at least about 8 ng/ml IL-7, at least about 9 ng/ml IL-7, at least about 10 ng/ml IL-7, at least about 11 ng/ml IL-7, at least about 12 ng/ml IL-7, at least about 13 ng/ml IL-7, at least about 14 ng/ml IL-7, at least about 15 ng/ml IL-7, at least about 20 ng/ml IL-7, at least about 25 ng/ml IL-7, at least about 30 ng/ml IL-7, at least about 35 ng/ml IL-7, at least about 40 ng/ml IL-7, at least about 45 ng/ml IL-7, at least about 50 ng/ml IL-7, at least about 100 ng/ml IL-7, at least about 200 ng/ml IL-7, at least about 300 ng/ml IL-7, at least about 400 ng/ml IL-7, at least about 500 ng/ml IL-7, or at least about 1000 ng/ml IL-7. In one embodiment, the one or more T cells are contacted with about 0.001 to about 500 ng/ml IL-7, about 0.01 to about 100 ng/ml IL-7, about 0.1 to about 50 ng/ml IL-7, about 1 to about 10 ng/ml IL-7, about 1 to about 5 ng/ml IL-7, about 5 to about 10 ng/ml IL-7, about 3 to about 7 ng/ml IL-7, or about 4 to about 6 ng/ml IL-7. In one particular embodiment, the one or more T cells are contacted with about 5 ng/ml IL-7.

Interleukin-15 (IL-15) is a cytokine that promotes T cell proliferation. It is expressed by members of the monocyte/macrophage lineage, blood-derived dendritic cells, bone marrow stromal cells, and epithelium cells of the thymus. IL-15 signals through its receptor, IL-15 receptor, to, e.g., activate the Jak/STAT pathway, stimulate the Ras/Raf/MAPK pathway, and to activate NF-κB.

Any exogenous IL-15 can be used in the methods described herein. In some embodiments, the exogenous IL-15 is human IL-15. In some embodiments, the exogenous IL-15 is wildtype IL-15. In other embodiments, the exogenous IL-15 is recombinant IL-15. The IL-15 can be produced and obtained by any methods known in the art, including but not limited to isolated IL-15 from one more IL-15 producing cells or obtaining a commercially available IL-15.

Any concentration of IL-15 can be used in the methods described herein. For example, the present method can include contacting the one or more T cells with at least about 0.001 ng/ml IL-15, at least about 0.005 ng/ml IL-15, at least about 0.01 ng/ml IL-15, at least about 0.05 ng/ml IL-15, at least about 0.1 ng/ml IL-15, at least about 0.5 ng/ml IL-15, at least about 1.0 ng/ml IL-15, at least about 1 ng/ml IL-15, at least about 2 ng/ml IL-15, at least about 3 ng/ml IL-15, at least about 4 ng/ml IL-15, at least about 5 ng/ml IL-15, at least about 6 ng/ml IL-15, at least about 7 ng/ml IL-15, at least about 8 ng/ml IL-15, at least about 9 ng/ml IL-15, at least about 10 ng/ml IL-15, at least about 11 ng/ml IL-15, at least about 12 ng/ml IL-15, at least about 13 ng/ml IL-15, at least about 14 ng/ml IL-15, at least about 15 ng/ml IL-15, at least about 20 ng/ml IL-15, at least about 25 ng/ml IL-15, at least about 30 ng/ml IL-15, at least about 35 ng/ml IL-15, at least about 40 ng/ml IL-15, at least about 45 ng/ml IL-15, at least about 50 ng/ml IL-15, at least about 100 ng/ml IL-15, at least about 200 ng/ml IL-15, at least about 300 ng/ml IL-15, at least about 400 ng/ml IL-15, at least about 500 ng/ml IL-15, or at least about 1000 ng/ml IL-15. In one embodiment, the one or more T cells are contacted with about 0.001 to about 500 ng/ml IL-15, about 0.01 to about 100 ng/ml IL-15, about 0.1 to about 50 ng/ml IL-15, about 1 to about 10 ng/ml IL-15, about 1 to about 5 ng/ml IL-15, about 5 to about 10 ng/ml IL-15, about 3 to about 7 ng/ml IL-15, or about 4 to about 6 ng/ml IL-15. In one particular embodiment, the one or more T cells are contacted with about 5 ng/ml IL-15.

In some embodiments, the one or more T cells are contacted with exogenous IL-7 and not exogenous IL-15. In other embodiments, the one or more T cells are contacted with exogenous IL-15 and not exogenous IL-7. In still other embodiments, the one or more T cells are contacted with both exogenous IL-7 and exogenous IL-15. When the one or more T cells are contacted with both exogenous IL-7 and exogenous IL-15, the one or more T cells can be contacted with equal or different concentrations of exogenous IL-7 and exogenous IL-15. In certain embodiments, the one or more T cells are contacted with equal concentrations of exogenous IL-7 and exogenous IL-15. In other embodiments, the one or more T cells are contacted with different concentrations of exogenous IL-7 and exogenous IL-15. In one embodiment, the one or more T cells are contacted with a higher concentration of exogenous IL-7 than exogenous IL-15. In another embodiment, the one or more T cells are contacted with a lower concentration of exogenous IL-7 than exogenous IL-15. In one particular embodiment, the one or more T cells are contacted with about 5 ng/ml exogenous IL-7 and about 5 ng/ml exogenous IL-15.

Furthermore, the one or more T cells can be contacted with exogenous IL-7 and exogenous IL-15 at the same time, e.g., concurrently, or at a different time, e.g., sequentially. In some embodiments, the one or more T cells are contacted with exogenous IL-7 before exogenous IL-15. In other embodiments, the one or more T cells are contacted with exogenous IL-15 before exogenous IL-7. In some embodiments, the one or more T cells are contacted with exogenous IL-7 and exogenous IL-15 at the same time.

T Cells

The one or more T cells described herein can be obtained from any source, including, for example, a human donor. The donor can be a subject in need of an anti-cancer treatment, e.g., treatment with one T cells generated by the methods described herein (i.e., an autologous donor), or can be an individual that donates a lymphocyte sample that, upon generation of the population of cells generated by the methods described herein, will be used to treat a different individual or cancer patient (i.e., an allogeneic donor). The population of lymphocytes can be obtained from the donor by any suitable method used in the art. For example, the population of lymphocytes can be obtained by any suitable extracorporeal method, venipuncture, or other blood collection method by which a sample of blood and/or lymphocytes is obtained. In one embodiment, the population of lymphocytes is obtained by apheresis. The one or more T cells can be collected from any tissue that comprises one or more T cells, including, but not limited to, a tumor. In some embodiments, a tumor or a portion thereof is collected from a subject, and one or more T cells are isolated from the tumor tissue. Any T cell can be used in the methods disclosed herein, including any T cells suitable for a T cell therapy. For example, the one or more cells useful for the invention can be selected from the group consisting of tumor infiltrating lymphocytes (TIL), cytotoxic T cells, CAR T cells, engineered TCR T cells, natural killer T cells, Dendritic cells, and peripheral blood lymphocytes. In one particular embodiment, the T cells are tumor infiltrating leukocytes. In certain embodiments, the one or more T cells express CD8, e.g., are $CD8^+$ T cells. In other embodiments, the one or more T cells express CD4, e.g., are $CD4^+$ T cells.

The methods described herein can be used to delay or inhibit T cell maturation or differentiation in vitro by contacting one or more T cells from a donor with an AKT inhibitor and at least one of exogenous IL-7 and exogenous IL-15. The inventors have found that treatment of one or more T cells with an AKT inhibitor and IL-7 and/or IL-15 increases the concentration of naïve and immature T cells in vitro. In particular, following treatment, the one or more T cells can express one or more genes indicative of undifferentiated or immature T cells. The one or more genes indicative of undifferentiated or immature T cells can be selected from the group CD8, CD45RA, CCR7, CD45RO, CD62L, CD28, CD95, IL-7Rα, CXCR4, TCF7, FOXO1, ID3, BCL6, and any combination thereof. For example, contacting one or more T cells with an AKT inhibitor and IL-7 and/or IL-15 can result in an increase in the percent of cells expressing one or more genes indicative of undifferentiated or immature T cells selected from CD8, CD45RA, CCR7, and any combination thereof.

In other embodiments, the one or more T cells express CCR7 and CD45RO following the contact with the AKT inhibitor and the exogenous IL-7 and/or exogenous IL-15. In one particular embodiment, a greater percentage of the one or more T cells express CCR7 and CD45RO after as compared to before being contacted with an AKT inhibitor and at least one of exogenous IL-7 and exogenous IL-15. In another embodiment, the one or more T cells express CCR7 and CD45RA following the contact with the AKT inhibitor and the exogenous IL-7 and/or exogenous IL-15. In one particular embodiment, a greater percentage of the one or more T cells express CCR7 and CD45RA after as compared to before being contacted with an AKT inhibitor and at least one of exogenous IL-7 and exogenous IL-15. In another embodiment, the T cells exhibit increased expression of CCR7, CD45RO, CD45RA, or any combination thereof following the contact with the AKT inhibitor and the exogenous IL-7 and/or exogenous IL-15, as compared to the expression of CCR7, CD45RO, and CD45RA by T cells not contacted with the AKT inhibitor and exogenous IL-7 and/or exogenous IL-15.

In other embodiments, the one or more T cells express CD62L, CD28, or both following the contact with the AKT inhibitor and the exogenous IL-7 and/or exogenous IL-15. In one particular embodiment, a greater percentage of the one or more T cells express CD62L, CD28, or both after as compared to before being contacted with an AKT inhibitor and at least one of exogenous IL-7 and exogenous IL-15. In another embodiment, the one or more T cells exhibit increased expression of CD62L, CD28, or both following the contact with the AKT inhibitor and the exogenous IL-7 and/or exogenous IL-15, as compared to the expression of CD62L and CD28 by T cells not contacted with the AKT inhibitor and the exogenous IL-7 and/or exogenous IL-15.

In one particular embodiment, the T cells exhibit increased expression of CD95, IL-7 receptor alpha (IL-7Rα), CXCR4, TCF7, FOXO1, ID3, BCL6, CD62L, CD45RA, or any combination thereof following the contact with the AKT inhibitor and the exogenous IL-7, exogenous IL-15, or both, as compared to the expression of CD95, IL-7 receptor alpha (IL-7Rα), CXCR4, TCF7, FOXO1, ID3, BCL6, CD62L, and CD45RA by T cells not contacted with the AKT inhibitor and the exogenous IL-7 and/or exogenous IL-15.

T Cell Therapy

The present invention provides methods of modulating, e.g., delaying or inhibiting, T cell maturation or differentiation in vitro for a T cell therapy, comprising contacting one or more T cells from a subject in need of a T cell therapy with (i) an AKT inhibitor and at least one of exogenous Interleukin-7 (IL-7) and exogenous Interleukin-15 (IL-15), wherein the resulting T cells exhibit delayed maturation or differentiation. In some embodiments, the method further includes administering the one or more T cells to a subject in need thereof. One of skill in the art would understand that the one or more T cells produced by the methods described herein can be used in any method of treating a patient comprising administering to the patient one or more T cells.

For example, and without limitation, the methods described herein can enhance the effectiveness of a T cell therapy, which can be an adoptive T cell therapy selected from the group consisting of tumor-infiltrating lymphocyte (TIL) immunotherapy, autologous cell therapy, engineered autologous cell therapy (eACT™), allogeneic T cell transplantation, non-T cell transplantation, and any combination thereof. Adoptive T cell therapy broadly includes any method of selecting, enriching in vitro, and administering to a patient autologous or allogeneic T cells that recognize and are capable of binding tumor cells. TIL immunotherapy is a type of adoptive T cell therapy, wherein lymphocytes capable of infiltrating tumor tissue are isolated, enriched in vitro, and administered to a patient. The TIL cells can be either autologous or allogeneic. Autologous cell therapy is an adoptive T cell therapy that involves isolating T cells capable of targeting tumor cells from a patient, enriching the T cells in vitro, and administering the T cells back to the same patient. Allogeneic T cell transplantation can include transplant of naturally occurring T cells expanded ex vivo or genetically engineered T cells. Engineered autologous cell therapy, as described in more detail above, is an adoptive T cell therapy wherein a patient's own lymphocytes are isolated, genetically modified to express a tumor targeting molecule, expanded in vitro, and administered back to the patient. Non-T cell transplantation can include autologous or allogeneic therapies with non-T cells such as, but not limited to, natural killer (NK) cells.

In one particular embodiment, the T cell therapy of the present invention is engineered Autologous Cell Therapy (eACT™). According to this embodiment, the method can include collecting blood cells from a donor. The isolated blood cells (e.g., T cells) can then be contacted with an AKT inhibitor and one or more of exogenous IL-7 and exogenous IL-15. The T cells can then be engineered to express a chimeric antigen receptor ("engineered CAR T cells") or T cell receptor ("engineered TCR T cells"). In one particular embodiment, the engineered CAR T cells or the engineered TCR T cells that were contacted with the AKT inhibitor and one or more of exogenous IL-7 and exogenous IL-15 are administered to a subject. In some embodiments, the engineered T cells treat a tumor in the subject.

In some embodiments, the one or more T cells are transduced with a retrovirus comprising a heterologous gene encoding a cell surface receptor. In one particular embodiment, the cell surface receptor is capable of binding an antigen on the surface of a target cell, e.g., on the surface of a tumor cell. In some embodiments the cell surface receptor is a chimeric antigen receptor or a T cell receptor.

In one embodiment, the one or more T cells can be engineered to express a chimeric antigen receptor. The chimeric antigen receptor can comprise a binding molecule to a tumor antigen. The binding molecule can be an antibody or an antigen binding molecule thereof. For example, the antigen binding molecule can be selected from scFv, Fab, Fab', Fv, F(ab')2, and dAb, and any fragments or combinations thereof.

The chimeric antigen receptor can further comprise a hinge region. The hinge region can be derived from the hinge region of IgG1, IgG2, IgG3, IgG4, IgA, IgD, IgE, IgM, CD28, or CD8 alpha. In one particular embodiment, the hinge region is derived from the hinge region of IgG4.

The chimeric antigen receptor can also comprise a transmembrane domain. The transmembrane domain can be a transmembrane domain of any transmembrane molecule that is a co-receptor on immune cells or a transmembrane domain of a member of the immunoglobulin superfamily. In certain embodiments, the transmembrane domain is derived from a transmembrane domain of CD28, CD28T, CD8 alpha, CD4, or CD19. In one particular embodiment, the transmembrane domain comprises a domain derived from a CD28 transmembrane domain. In another embodiment, the transmembrane domain comprises a domain derived from a CD28T transmembrane domain.

The chimeric antigen receptor can further comprise one or more costimulatory signaling regions. For example, the costimulatory signaling region can be a signaling region of CD28, CD28T, OX-40, 41BB, CD27, inducible T cell costimulator (ICOS), CD3 gamma, CD3 delta, CD3 epsilon, CD247, Ig alpha (CD79a), or Fc gamma receptor. In one particular embodiment, the costimulatory signaling region is a CD28 signaling region. In another embodiment, the costimulatory signaling region is a CD28T signaling region.

In one embodiment, the chimeric antigen receptor further comprises a CD3 zeta signaling domain.

The chimeric antigen receptor can be engineered to target a particular tumor antigen. In some embodiments, the tumor antigen is selected from 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), x-light chain, LAGE (L antigen), LDLR/FUT (low density lipid receptor/GDP-L-fucose: b-D-galactosidase 2-a-Lfucosyltransferase), LeY (Lewis-Y antibody), L1CAM (L1 cell adhesion molecule), MAGE (melanoma antigen), MAGE-A1 (Melanoma-associated antigen 1), MAGE-A3, MAGE-A6, mesothelin, Murine CMV infected cells, MART-1/Melan-A (melanoma antigen recognized by T cells-1/Melanoma antigen A), MC1R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), WT1 (Wilms' tumor gene), and any combination thereof. In one particular embodiment, the tumor antigen is CD19.

In another embodiment, the T cell therapy comprises administering to the patient engineered T cells expressing T cell receptor ("engineered TCR T cells"). The T cell receptor (TCR) can comprise a binding molecule to a tumor antigen. In some embodiments, the tumor antigen is selected from the group consisting of 707-AP, AFP, ART-4, BAGE, BCMA, Bcr-abl, CAIX, CD19, CD20, CD22, CD30, CD33, CD44v7/8, CAMEL, CAP-1, CASP-8, CDC27m, CDK4/m, CEA, CT, Cyp-B, DAM, EGFR, EGFRvIII, EGP-2, EGP-40, Erbb2, 3, 4, ELF2M, ETV6-AML1, FBP, fAchR, G250, GAGE, GD2, GD3, GnT-V, Gp100, HAGE, HER-2/neu, HLA-A, HPV, HSP70-2M, HST-2, hTERT or hTRT, iCE, IL-13R-a2, KIAA0205, KDR, κ-light chain, LAGE, LDLR/ FUT, LeY, L1CAM, MAGE, MAGE-A1, mesothelin, Murine CMV infected cells, MART-1/Melan-A, MC1R, Myosin/m, MUC1, MUM-1, -2, -3, NA88-A, NKG2D ligands, NY-BR-1, NY-ESO-1, oncofetal antigen, P15, p190 minor bcr-abl, Pml/RARa, PRAME, PSA, PSCA, PSMA, RAGE, RU1 or RU2, SAGE, SART-1 or SART-3, SSX1, -2, -3, 4, TAA, TAG-72, TEL/AML1, TPI/m, TRP-1, TRP-2, TRP-2/INT2, VEGF-R2, WT1, and any combination thereof.

In one embodiment, the TCR comprises a binding molecule to a viral oncogene. In one particular embodiment, the viral oncogene is selected from human papilloma virus (HPV), Epstein-Barr virus (EBV), and human T-lymphotropic virus (HTLV).

In still another embodiment, the TCR comprises a binding molecule to a testicular, placental, or fetal tumor antigen. In one particular embodiment, the testicular, placental, or fetal tumor antigen is selected from the group consisting of NY-ESO-1, synovial sarcoma X breakpoint 2 (SSX2), melanoma antigen (MAGE), and any combination thereof.

In another embodiment, the TCR comprises a binding molecule to a lineage specific antigen. In one particular embodiment, the lineage specific antigen is selected from the group consisting of melanoma antigen recognized by T cells 1 (MART-1), gp100, prostate specific antigen (PSA), prostate specific membrane antigen (PSMA), prostate stem cell antigen (PSCA), and any combination thereof.

In one embodiment, the T cell therapy comprises administering to the patient engineered CAR T cells expressing a chimeric antigen receptor that binds to CD19 and further comprises a CD28 costimulatory domain and a CD3-zeta signaling region. In a particular embodiment, the T cell therapy comprises administering to a patient KTE-C19.

In one embodiment, the antigenic moieties also include, but are not limited to, an Epstein-Barr virus (EBV) antigen (e.g., EBNA-1, EBNA-2, EBNA-3, LMP-1, LMP-2), a hepatitis A virus antigen (e.g., VP1, VP2, VP3), a hepatitis B virus antigen (e.g., HBsAg, HBcAg, HBeAg), a hepatitis C viral antigen (e.g., envelope glycoproteins E1 and E2), a herpes simplex virus type 1, type 2, or type 8 (HSV1, HSV2, or HSV8) viral antigen (e.g., glycoproteins gB, gC, gC, gE, gG, gH, gI, gJ, gK, gL. gM, UL20, UL32, US43, UL45, UL49A), a cytomegalovirus (CMV) viral antigen (e.g., glycoproteins gB, gC, gC, gE, gG, gH, gI, gJ, gK, gL. gM or other envelope proteins), a human immunodeficiency virus (HIV) viral antigen (glycoproteins gp120, gp41, or p24), an influenza viral antigen (e.g., hemagglutinin (HA) or neuraminidase (NA)), a measles or mumps viral antigen, a human papillomavirus (HPV) viral antigen (e.g., L1, L2), a parainfluenza virus viral antigen, a rubella virus viral antigen, a respiratory syncytial virus (RSV) viral antigen, or a varicella-zostser virus viral antigen. In such embodiments, the cell surface receptor can be any TCR, or any CAR which recognizes any of the aforementioned viral antigens on a target virally infected cell.

In other embodiments, the antigenic moiety is associated with cells having an immune or inflammatory dysfunction. Such antigenic moieties can include, but are not limited to, myelin basic protein (MBP) myelin proteolipid protein (PLP), myelin oligodendrocyte glycoprotein (MOG), carcinoembryonic antigen (CEA), pro-insulin, glutamine decarboxylase (GAD65, GAD67), heat shock proteins (HSPs), or any other tissue specific antigen that is involved in or associated with a pathogenic autoimmune process.

The methods disclosed herein can involve a T cell therapy comprising the transfer of one or more T cells to a patient.

The T cells can be administered at a therapeutically effective amount. For example, a therapeutically effective amount of T cells, e.g., engineered CAR+ T cells or engineered TCR+ T cells, can be at least about $10^4$ cells, at least about $10^5$ cells, at least about $10^6$ cells, at least about $10^7$ cells, at least about $10^8$ cells, at least about $10^9$, or at least about $10^{10}$. In another embodiment, the therapeutically effective amount of the T cells, e.g., engineered CAR+ T cells or engineered TCR+ T cells, is about $10^4$ cells, about $10^5$ cells, about $10^6$ cells, about $10^7$ cells, or about $10^8$ cells. In one particular embodiment, the therapeutically effective amount of the T cells, e.g., engineered CAR+ T cells or engineered TCR+ T cells, is about $2\times10^6$ cells/kg, about $3\times10^6$ cells/kg, about $4\times10^6$ cells/kg, about $5\times10^6$ cells/kg, about $6\times10^6$ cells/kg, about $7\times10^6$ cells/kg, about $8\times10^6$ cells/kg, about $9\times10^6$ cells/kg, about $1\times10^7$ cells/kg, about $2\times10^7$ cells/kg, about $3\times10^7$ cells/kg, about $4\times10^7$ cells/kg, about $5\times10^7$ cells/kg, about $6\times10^7$ cells/kg, about $7\times10^7$ cells/kg, about $8\times10^7$ cells/kg, or about $9\times10^7$ cells/kg.

In some embodiments, the patient is preconditioned prior to administration of the T cell therapy. The patient can be preconditioned according to any methods known in the art, including, but not limited to, treatment with one or more chemotherapy drug and/or radiotherapy. In some embodiments, the preconditioning can include any treatment that reduces the number of endogenous lymphocytes, removes a cytokine sink, increases a serum level of one or more homeostatic cytokines or pro-inflammatory factors, enhances an effector function of T cells administered after the conditioning, enhances antigen presenting cell activation and/or availability, or any combination thereof prior to a T cell therapy. In one embodiment, the preconditioning comprises increasing a serum level of one or more cytokines in the subject.

Cancer Treatment

The methods of the invention can be used to treat a cancer in a subject, reduce the size of a tumor, kill tumor cells, prevent tumor cell proliferation, prevent growth of a tumor, eliminate a tumor from a patient, prevent relapse of a tumor, prevent tumor metastasis, induce remission in a patient, or any combination thereof. In certain embodiments, the methods induce a complete response. In other embodiments, the methods induce a partial response.

One embodiment, the invention is directed to a method of treating a tumor in a subject in need of a T cell therapy comprising administering to the subject one or more T cells, wherein the one or more T cells have been contacted with (i) an AKT inhibitor and (ii) exogenous IL-7 and/or exogenous IL-15. In another embodiment, the invention is directed to a method of reducing or decreasing the size of a tumor or inhibiting growth of a tumor in a subject in need of a T cell therapy comprising administering to the subject one or more T cells, wherein the one or more T cells have been contacted with (i) an AKT inhibitor and (ii) exogenous IL-7 and/or exogenous IL-15. In certain embodiments, the one or more T cells have not been contacted with exogenous IL-2.

Cancers that can be treated include tumors that are not vascularized, not yet substantially vascularized, or vascularized. The cancer can also include solid or non-solid tumors. In certain embodiments, the cancer can be selected from a tumor derived from acute lymphoblastic leukemia (ALL), acute myeloid leukemia (AML), adenoid cystic carcinoma, adrenocortical, carcinoma, AIDS-related cancers, anal cancer, appendix cancer, astrocytomas, atypical teratoid/rhabdoid tumor, central nervous system, B-cell leukemia, lymphoma or other B cell malignancies, basal cell carcinoma, bile duct cancer, bladder cancer, bone cancer, osteosarcoma and malignant fibrous histiocytoma, brain stem glioma, brain tumors, breast cancer, bronchial tumors, burkitt lymphoma, carcinoid tumors, central nervous system cancers, cervical cancer, chordoma, chronic lymphocytic leukemia (CLL), chronic myelogenous leukemia (CIVIL), chronic myeloproliferative disorders, colon cancer, colorectal cancer, craniopharyngioma, cutaneous t-cell lymphoma, embryonal tumors, central nervous system, endometrial cancer, ependymoblastoma, ependymoma, esophageal cancer, esthesioneuroblastoma, ewing sarcoma family of tumors extracranial germ cell tumor, extragonadal germ cell tumor extrahepatic bile duct cancer, eye cancer fibrous histiocytoma of bone, malignant, and osteosarcoma, gallbladder cancer, gastric (stomach) cancer, gastrointestinal carcinoid tumor, gastrointestinal stromal tumors (GIST), soft tissue sarcoma, germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, kidney cancer, langerhans cell histiocytosis, laryngeal cancer, leukemia, lip and oral cavity cancer, liver cancer (primary), lobular carcinoma in situ (LCIS), lung cancer, lymphoma, macroglobulinemia, male breast cancer, malignant fibrous histiocytoma of bone and osteosarcoma, medulloblastoma, medulloepithelioma, melanoma, merkel cell carcinoma, mesothelioma, metastatic squamous neck cancer with occult primary midline tract carcinoma involving NUT gene, mouth cancer, multiple endocrine neoplasia syndromes, multiple myeloma/plasma cell neoplasm, mycosis fungoides, myelodysplastic syndromes, myelodysplastic/myeloproliferative neoplasms, myelogenous leukemia, chronic (CIVIL), Myeloid leukemia, acute (AML), myeloma, multiple, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, pancreatic cancer, papillomatosis, paraganglioma, paranasal sinus and nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, pregnancy and breast cancer, primary central nervous system (CNS) lymphoma, prostate cancer, rectal cancer, renal cell (kidney) cancer, renal pelvis and ureter, transitional cell cancer, retinoblastoma, rhabdomyosarcoma, salivary gland cancer, sarcoma, sézary syndrome, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, cutaneous, testicular cancer, throat cancer, thymoma and thymic carcinoma, thyroid cancer, transitional cell cancer of the renal pelvis and ureter, trophoblastic tumor, ureter and renal pelvis cancer, urethral cancer, uterine cancer, uterine sarcoma, vaginal cancer, vulvar cancer, Waldenström macroglobulinemia, Wilms Tumor.

In one embodiment, the method can be used to treat a tumor, wherein the tumor is a lymphoma or a leukemia. Lymphoma and leukemia are cancers of the blood that specifically affect lymphocytes. All leukocytes in the blood originate from a single type of multipotent hematopoietic stem cell found in the bone marrow. This stem cell produces both myeloid progenitor cells and lymphoid progenitor cell, which then give rise to the various types of leukocytes found in the body. Leukocytes arising from the myeloid progenitor cells include T lymphocytes (T cells), B lymphocytes (B cells), natural killer cells, and plasma cells. Leukocytes arising from the lymphoid progenitor cells include megakaryocytes, mast cells, basophils, neutrophils, eosinophils, monocytes, and macrophages. Lymphomas and leukemias can affect one or more of these cell types in a patient.

In general, lymphomas can be divided into at least two sub-groups: Hodgkin lymphoma and non-Hodgkin lymphoma. Non-Hodgkin Lymphoma (NHL) is a heterogeneous group of cancers originating in B lymphocytes, T lymphocytes or natural killer cells. In the United States, B cell lymphomas represent 80-85% of cases reported. In 2013 approximately 69,740 new cases of NHL and over 19,000 deaths related to the disease were estimated to occur. Non-Hodgkin lymphoma is the most prevalent hematological malignancy and is the seventh leading site of new cancers among men and women and account for 4% of all new cancer cases and 3% of deaths related to cancer.

Diffuse large B cell lymphoma (DLBCL) is the most common subtype of NHL, accounting for approximately 30% of NHL cases. There are approximately 22,000 new diagnoses of DLBCL in the United States each year. It is classified as an aggressive lymphoma with the majority of patients cured with conventional chemotherapy (NCCN guidelines NHL 2014).

First line therapy for DLBCL typically includes an anthracycline-containing regimen with rituximab, such as R-CHOP (rituximab, cyclophosphamide, doxorubicin, vincristine, and prednisone), which has an objective response rate of about 80% and a complete response rate of about 50% (Coiffier 2002), with about one-third of patients have refractory disease to initial therapy or relapse after R-CHOP (Sehn 2005). For those patients who relapse after response to first line therapy, approximately 40-60% of patients can achieve a second response with additional chemotherapy. The standard of care for second-line therapy for autologous stem cell transplant (ASCT) eligible patients includes rituximab and combination chemotherapy such as R-ICE (rituximab, ifosfamide, carboplatin, and etoposide) and R-DHAP (rituximab, dexamethasone, cytarabine, and cisplatin), which each have an objective response rate of about 63% and a complete response rate of about 26% (Gisselbrecht 2010). Patients who respond to second line therapy and who are considered fit enough for transplant receive consolidation with high-dose chemotherapy and ASCT, which is curative in about half of transplanted patients (Gisselbrecht 2010). Patients who failed ASCT have a very poor prognosis and no curative options.

Primary mediastinal large B cell lymphoma (PMBCL) has distinct clinical, pathological, and molecular characteristics compared to DLBCL. PMBCL is thought to arise from thymic (medullary) B cells and represents approximately 3% of patients diagnosed with DLBCL. PMBCL is typically identified in the younger adult population in the fourth decade of life with a slight female predominance. Gene expression profiling suggests deregulated pathways in PMBCL overlap with Hodgkin lymphoma. Initial therapy of PMBCL generally includes anthracycline-containing regimens with rituximab, such as infusional dose-adjusted etoposide, doxorubicin, and cyclophosphamide with vincristine, prednisone, and rituximab (DA-EPOCH-R), with or without involved field radiotherapy.

Follicular lymphoma (FL), a B cell lymphoma, is the most common indolent (slow-growing) form of NHL, accounting for approximately 20% to 30% of all NHLs. Some patients with FL will transform (TFL) histologically to DLBCL which is more aggressive and associated with a poor outcome. Histological transformation to DLBCL occurs at an annual rate of approximately 3% for 15 years with the risk of transformation continuing to drop in subsequent years. The biologic mechanism of histologic transformation is unknown. Initial treatment of TFL is influenced by prior therapies for follicular lymphoma but generally includes anthracycline-containing regimens with rituximab to eliminate the aggressive component of the disease.

Treatment options for relapsed/refractory PMBCL and TFL are similar to those in DLBCL. Given the low prevalence of these diseases, no large prospective randomized studies in these patient populations have been conducted. Patients with chemotherapy refractory disease have a similar or worse prognosis to those with refractory DLBCL.

In summary, subjects who have refractory, aggressive NHL (e.g., DLBCL, PMBCL and TFL) have a major unmet medical need and further research with novel treatments are warranted in these populations.

Accordingly, in some embodiments, the method can be used to treat a lymphoma or a leukemia, wherein the lymphoma or leukemia is a B cell malignancy. Examples of B cell malignancies include, but are not limited to, Non-Hodgkin's Lymphomas (NHL), Small lymphocytic lymphoma (SLL/CLL), Mantle cell lymphoma (MCL), FL, Marginal zone lymphoma (MZL), Extranodal (MALT lymphoma), Nodal (Monocytoid B-cell lymphoma), Splenic, Diffuse large cell lymphoma, B cell chronic lymphocytic leukemia/lymphoma, Burkitt's lymphoma, and Lymphoblastic lymphoma. In some embodiments, the lymphoma or leukemia is selected from B-cell chronic lymphocytic leukemia/small cell lymphoma, B-cell prolymphocytic leukemia, lymphoplasmacytic lymphoma (e.g., Waldenström macroglobulinemia), splenic marginal zone lymphoma, hairy cell leukemia, plasma cell neoplasms (e.g., plasma cell myeloma (i.e., multiple myeloma), or plasmacytoma), extranodal marginal zone B cell lymphoma (e.g., MALT lymphoma), nodal marginal zone B cell lymphoma, follicular lymphoma (FL), transformed follicular lymphoma (TFL), primary cutaneous follicle center lymphoma, mantle cell lymphoma, diffuse large B cell lymphoma (DLBCL), Epstein-Barr virus-positive DLBCL, lymphomatoid granulomatosis, primary mediastinal (thymic) large B-cell lymphoma (PMBCL), Intravascular large B-cell lymphoma, ALK+ large B-cell lymphoma, plasmablastic lymphoma, primary effusion lymphoma, large B-cell lymphoma arising in HHV8-associated multicentric Castleman's disease, Burkitt lymphoma/leukemia, T-cell prolymphocytic leukemia, T-cell large granular lymphocyte leukemia, aggressive NK cell leukemia, adult T-cell leukemia/lymphoma, extranodal NK/T-cell lymphoma, enteropathy-associated T-cell lymphoma, Hepatosplenic T-cell lymphoma, blastic NK cell lymphoma, Mycosis fungoides/Sezary syndrome, Primary cutaneous anaplastic large cell lymphoma, Lymphomatoid papulosis, Peripheral T-cell lymphoma, Angioimmunoblastic T cell lymphoma, Anaplastic large cell lymphoma, B-lymphoblastic leukemia/lymphoma, B-lymphoblastic leukemia/lymphoma with recurrent genetic abnormalities, T-lymphoblastic leukemia/lymphoma, and Hodgkin lymphoma. In some embodiments, the cancer is refractory to one or more prior treatments, and/or the cancer has relapsed after one or more prior treatments.

In certain embodiments, the cancer is selected from follicular lymphoma, transformed follicular lymphoma, diffuse large B cell lymphoma, and primary mediastinal (thymic) large B-cell lymphoma. In one particular embodiment, the cancer is diffuse large B cell lymphoma.

In some embodiments, the cancer is refractory to or the cancer has relapsed following one or more of chemotherapy, radiotherapy, immunotherapy (including a T cell therapy and/or treatment with an antibody or antibody-drug conjugate), an autologous stem cell transplant, or any combination thereof. In one particular embodiment, the cancer is refractory diffuse large B cell lymphoma.

In some embodiments, the cancer is treated by administering the one or more T cells to a subject, wherein the one or more T cells have been contacted with (i) an AKT inhibitor and (ii) exogenous IL-7 and/or exogenous IL-15. In certain embodiments, the one or more T cells are washed prior to administering the one or more T cells to the subject to remove the AKT inhibitor, exogenous IL-7, and/or exogenous IL-15. In some embodiments, the one or more T cells comprise engineered CAR cells or engineered TCR cell. In one embodiment, the engineered CAR cells or the engineered T cells treat a tumor in the subject.

Kits

Also included within the scope of the present invention are kits, e.g., pharmaceutical kits, comprising an AKT inhibitor and one or more of exogenous IL-7 and exogenous IL-15 for contacting one or more T cells in vitro. Kits typically include a label indicating the intended use of the contents of the kit and instructions for use. The term "label" includes any writing, or recorded material supplied on or with the kit, or which otherwise accompanies the kit.

In some embodiments, the invention provides a kit for preparing one or more T cells for a T cell therapy for a subject in need thereof, the kit comprising:
 (i) an AKT inhibitor,
 (ii) exogenous IL-7, and
 (iii) instructions to contact one or more T cells intended for use in a T cell therapy with the AKT inhibitor and the exogenous IL-7.

In other embodiments, the invention provides a kit for preparing one or more T cells for a T cell therapy for a subject in need thereof, the kit comprising:
 (i) an AKT inhibitor,
 (ii) exogenous IL-15, and
 (iii) instructions to contact one or more T cells intended for use in a T cell therapy with the AKT inhibitor and the exogenous IL-15.

In other embodiments, the invention provides a kit for preparing one or more T cells for a T cell therapy for a subject in need thereof, the kit comprising:
 (i) an AKT inhibitor,
 (ii) exogenous IL-7,
 (iii) exogenous IL-15, and
 (iii) instructions to contact one or more T cells intended for use in a T cell therapy with the AKT inhibitor, the exogenous IL-7, and/or the exogenous IL-15.

The present invention is further illustrated by the following examples which should not be construed as further limiting. The contents of all references cited throughout this application are expressly incorporated herein by reference.

The following examples are intended to illustrate various embodiments of the invention. As such, the specific embodiments discussed are not to be construed as limitations on the scope of the invention. For example, although the Examples below are directed to T cells transduced with an anti-CD19 chimeric antigen receptor (CAR), one skilled in the art would understand that the methods described herein can apply to T cells transduced with any CAR. It will be apparent to one skilled in the art that various equivalents, changes, and modifications can be made without departing from the scope of invention, and it is understood that such equivalent embodiments are to be included herein. Further, all references cited in the disclosure are hereby incorporated by reference in their entirety, as if fully set forth herein.

Embodiments

E1. A method for delaying or inhibiting T cell maturation or differentiation in vitro for a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit delayed maturation or differentiation, and/or wherein the resulting T cells exhibit improved T cell function relative to a T cell function of a T cell cultured in the absence of an AKT inhibitor.

E2. A method for improving T cell function in vitro for a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit an improved T cell function relative to a T cell function of a T cell cultured in the absence of an AKT inhibitor.

E3. The method of E1 or E2, wherein the improved T cell function is selected from the group consisting of:
  (i) increased T cell proliferation;
  (ii) increased cytokine production;
  (iii) increased cytolytic activity; and
  (iv) any combination of (i)-(iii).

E4. A method for increasing T cell proliferation in vitro prior to a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit increased T cell proliferation relative the T cell proliferation of a T cell cultured in the absence of an AKT inhibitor.

E5. A method for increasing T cell cytokine production in vitro prior to a T cell therapy, comprising contacting one or more T cells from a subject in need of a T cell therapy with an AKT inhibitor and exogenous Interleukin-7 (IL-7) and exogenous Interleukin-15 (IL-15), wherein the resulting T cells exhibit increased cytokine production relative the cytokine production of a T cell cultured in the absence of an AKT inhibitor.

E6. The method of E3 or E5, wherein the increased cytokine production is selected from the group consisting of (i) increased interferon gamma (IFNg) production, (ii) increased tissue necrosis factor alpha (TNFa) production, and (iii) both increased IFNg and TNFa production.

E7. A method for increasing T cell cytolytic activity in vitro for a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit increased cytolytic activity relative the T cell cytolytic activity of a T cell cultured in the absence of an AKT inhibitor.

E8. A method for delaying or inhibiting T cell maturation or differentiation in vitro for a T cell therapy, comprising contacting one or more T cells from a subject in need of a T cell therapy with an AKT inhibitor and at least one of exogenous Interleukin-7 (IL-7) and exogenous Interleukin-15 (IL-15), wherein the resulting T cells exhibit delayed maturation or differentiation.

E9. The method of any one of E1 to E8, wherein the contacting comprises culturing the one or more T cells in a medium comprising (i) the AKT inhibitor and (ii) exogenous IL-7 and/or exogenous IL-15.

E10. The method any one of E1 to E9, wherein the one or more T cells are not contacted with exogenous Interleukin-2 (IL-2).

E11. The method of any one of E1 to E10, wherein the T cells are washed to remove the AKT inhibitor, exogenous IL-7, and/or exogenous IL-15.

E12. The method of any one of E1 to E11, wherein the AKT inhibitor is selected from the group consisting of A6730, B2311, 124018, GSK2110183 (afuresertib), Perifosine (KRX-0401), GDC-0068 (ipatasertib), RX-0201, VQD-002, LY294002, A-443654, A-674563, Akti-1, Akti-2, Akti-1/2, AR-42, API-59CJ-OMe, ATI-13148, AZD-5363, erucylphosphocholine, GSK-2141795 (GSK795), KP372-1, L-418, NL-71-101, PBI-05204, PIA5, PX-316, SR13668, triciribine, GSK 690693 (CAS #937174-76-0), FPA 124 (CAS #902779-59-3), Miltefosine, PHT-427 (CAS #1 191951-57-1), 10-DEBC hydrochloride, Akt inhibitor III, Akt inhibitor VIII, MK-2206 dihydrochloride (CAS #1032350-13-2), SC79, AT7867 (CAS #857531-00-1), CCT128930 (CAS #885499-61-6), A-674563 (CAS #552325-73-2), AGL 2263, AS-041 164 (5-benzo[1,3]dioxol-5-ylmethylene-thiazolidine-2,4-dione), BML-257 (CAS #32387-96-5), XL-418, CAS #612847-09-3, CAS #98510-80-6, H-89 (CAS #127243-85-0), OXY-1 1 1 A, 3-[1-[[4-(7-phenyl-3H-imidazo[4,5-g]quinoxalin-6-yl)phenyl]methyl]piperidin-4-yl]-1H-benzimidazol-2-one, and any combination thereof.

E13. The method of any one of E1 to E12, wherein the AKT inhibitor comprises a compound selected from the group consisting of: (i) 3-[1-[[4-(7-phenyl-3H-imidazo[4,5-g]quinoxalin-6-yl)phenyl]methyl]piperidin-4-yl]-1H-benzimidazol-2-one; (ii) N,N-dimethyl-1-[4-(6-phenyl-1H-imidazo[4,5-g]quinoxalin-7-yl)phenyl]metha-namine; or (iii) 1-{1-[4-(3-phenylbenzo[g]quinoxalin-2-yl)benzyl]piperidin-4-yl}-1,-3-dihydro-2H-benzimidazol-2-one.

E14. The method of any one of E1 to E13, wherein the AKT inhibitor is a compound selected from the group consisting of: (i) 3-[1-[[4-(7-phenyl-3H-imidazo[4,5-g]quinoxalin-6-yl)phenyl]methyl]piperidin-4-yl]-1H-benzimidazol-2-one; (ii) N,N-dimethyl-1-[4-(6-phenyl-1H-imidazo[4,5-g]quinoxalin-7-yl)phenyl]metha-namine; or (iii) 1-{1-[4-(3-phenylbenzo[g]quinoxalin-2-yl)benzyl]piperidin-4-yl}-1,-3-dihydro-2H-benzimidazol-2-one.

E15. The method of any one of E1 to E14, wherein the AKT inhibitor is 3-[1-[[4-(7-phenyl-3H-imidazo[4,5-g]quinoxalin-6-yl)phenyl]methyl]piperidin-4-yl]-1H-benzimidazol-2-one.

E16. The method of E15, wherein the AKT inhibitor is at an amount of from about 1 nM to about 1 mM.

E17. The method of E15, wherein the AKT inhibitor is at an amount selected from the group consisting of at least about 1 nM, at least about 10 nM, at least about 50 nM, at least about 100 nM, at least about 200 nM, at least about 300 nM, at least about 400 nM, at least about 500 nM, at least about 1 µM, at least about 2 µM, at least about 3 µM, at least about 4 µM, at least about 5 µM, at least about 6 µM, at least about 7 µM, at least about 8 µM, at least about 9 µM, at least about 10 µM, at least about 11 µM, at least about 12 µM, at least about 13 µM, at least about 14 µM, at least about 15 µM, at least about 16 µM, at least about 17 µM, at least about 18 µM, at least about 19 µM, at least about 20 µM, at least about 25 µM, at least about 30 µM, at least about 35 µM, at least about 40 µM, at least about 45 µM, at least about 50

µM, at least about 60 µM, at least about 70 µM, at least about 80 µM, at least about 90 µM, at least about 100 µM, at least about 200 µM, at least about 300 µM, at least about 400 µM, at least about 500 µM, or at least about 1 mM.

E18. The method of E15, wherein the AKT inhibitor is at an amount of about 8 µM.

E19. The method of any one of E1 to E18, wherein the exogenous IL-7 is at an amount of about 0.001 to about 500 ng/ml IL-7.

E20. The method of any one of E1 to E18, wherein the exogenous IL-7 is at an amount of about 1 to about 10 ng/ml IL-7.

E21. The method of any one of E1 to E18, wherein the exogenous IL-7 is at an amount of at least about 5 ng/ml IL-7.

E22. The method of any one of E1 to E21, wherein the exogenous IL-15 is at an amount of about 0.001 to about 500 ng/ml IL-15.

E23. The method of any one of E1 to E21, wherein the exogenous IL-15 is at an amount of about 1 to about 10 ng/ml IL-15.

E24. The method of any one of E1 to E21, wherein the exogenous IL-15 is at an amount of at least about 5 ng/ml IL-15.

E25. The method of any one of E1 to E24, wherein the one or more T cells express CD8.

E26. The method of E25, wherein the one or more T cells are selected from the group consisting of tumor infiltrating lymphocytes, cytotoxic T cells, CAR T cells, engineered TCR T cells, natural killer T cells, and peripheral blood lymphocytes.

E27. The method of any one of E1 to E26, wherein the one or more T cells are collected from a subject in need of an anti-cancer treatment.

E28. The method of E27, wherein the one or more T cells are collected from a tumor in the subject in need of an anti-cancer treatment.

E29. The method of E20 or E28, wherein the one or more T cells comprise one or more tumor infiltrating leukocytes (TIL).

E30. The method of any one of E1 to E29, wherein the T cells are activated.

E31. The method of E30, wherein the activation of the T cells are in a closed system.

E32. The method of E31, wherein the closed system comprises a closed bag system.

E33. The method of any one of E1 to E32, wherein the T cells are expanded.

E34. The method of E32, wherein the T cells are expanded in vitro.

E35. The method of E32, wherein the T cells are expanded in vivo.

E36. The method of any one of E1 to E35, wherein the contacting the one or more T cells with the AKT inhibitor and the exogenous IL-7 and/or exogenous IL-15 extends the in vivo persistence of the T cells.

E37. The method of any one of E1 to E36, wherein following the contacting of the one or more T cells with the AKT inhibitor and at least one of exogenous IL-7 and exogenous IL-15, the resulting T cells express one or more genes indicative of undifferentiated or immature T cells.

E38. The method of E37, wherein the one or more genes indicative of undifferentiated or immature T cells are selected from the group consisting of CD8, CD45RA, CCR7, and any combination thereof.

E39. The method of any one of E1 to E38, further comprising transducing the T cells with a retrovirus.

E40. The method of E39, wherein the retrovirus comprises a heterologous gene encoding a cell surface receptor.

E41. The method of E40 wherein the cell surface receptor is capable of binding an antigen on the surface of a target cell.

E42. The method of E41, wherein the target cell is a tumor cell.

E43. The method of E41 or E42, wherein the cell surface receptor is a T cell receptor (TCR) or a chimeric antigen receptor (CAR).

E44. The method of any one of E41 to E43, wherein the cell surface receptor is capable of binding an antigen selected from the group consisting of 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2,3,4 (erythroblastic leukemia viral oncogene homolog-2, -3, 4), ELF2M (elongation factor 2 mutated), ETV6-AME1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), K-light chain, LAGE (L antigen), LDLR/FUT (low density lipid receptor/GDP-L-fucose: b-D-galactosidase 2-a-Lfucosyltransferase), LeY (Lewis-Y antibody), L1 CAM (L1 cell adhesion molecule), MAGE (melanoma antigen), MAGE-A1 (Melanoma-associated antigen 1), mesothelin, Murine CMV infected cells, MART-1/Melan-A (melanoma antigen recognized by T cells-1/Melanoma antigen A), MC1R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), WT1 (Wilms' tumor gene), and any combination thereof.

E45. The method of any one of E1 to E44, further comprising administering the resulting T cells to a subject in need thereof.

E46. A method of treating a tumor in a subject in need of a T cell therapy comprising administering to the subject one or more T cells, wherein the one or more T cells have been contacted with (i) an AKT inhibitor and (ii) exogenous IL-7 and/or exogenous IL-15.

E47. A method of reducing or decreasing the size of a tumor or inhibiting growth of a tumor in a subject in need of a T cell therapy comprising administering to the subject one or more T cells, wherein the one or more T cells have been contacted with (i) an AKT inhibitor and (ii) exogenous IL-7 and/or exogenous IL-15.

E48. The method of E46 or E47, wherein the one or more T cells have not been contacted with exogenous IL-2.

E49. The method of any one of E46 to E48, wherein the T cells express CCR7 and CD45RO following the contact with the AKT inhibitor and the exogenous IL-7 and/or exogenous IL-15.

E50. The method of any one of E46 to E48, wherein the T cells express CCR7 and CD45RA following the contact with the AKT inhibitor and the exogenous IL-7, exogenous IL-15, or both.

E51. The method of any one of E46 to E48, wherein the T cells exhibit increased expression of CCR7, CD45RO, CD45RA, or any combination thereof following the contact with the AKT inhibitor and the exogenous IL-7 and/or exogenous IL-15, as compared to the expression of CCR7, CD45RO, and CD45RA by T cells not contacted with the AKT inhibitor and the exogenous IL-7 and/or exogenous IL-15.

E52. The method of any one of E46 to E51, wherein the T cells express CD62L, CD28, or both following the contact with the AKT inhibitor and the exogenous IL-7 and/or exogenous IL-15.

E53. The method of any one of E46 to E52, wherein the T cells exhibit increased expression of CD62L, CD28, or both following the contact with the AKT inhibitor and the exogenous IL-7 and/or exogenous IL-15, as compared to the expression of CD62L and CD28 by T cells not contacted with the AKT inhibitor and the exogenous IL-7 and/or exogenous IL-15.

E54. The method of any one of E46 to E53, wherein the T cells exhibit increased expression of CD95, IL-7 receptor alpha (IL-7Rα), CXCR4, TCF7, FOXO1, ID3, BCL6, CD62L, CD45RA, or any combination thereof following the contact with the AKT inhibitor and the exogenous IL-7, exogenous IL-15, or both, as compared to the expression of CD95, IL-7 receptor alpha (IL-7Rα), CXCR4, TCF7, FOXO1, ID3, BCL6, CD62L, and CD45RA by T cells not contacted with the AKT inhibitor and the exogenous IL-7 and/or exogenous IL-15.

E55. The method of any one of E46 to E54, wherein the one or more T cells are isolated from a donor.

E56. The method of E55, wherein the donor is a subject

E57. The method of any one of E46 to E56, wherein the tumor is a cancer.

E58. The method of E57, wherein the cancer is selected from bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma (NHL), primary mediastinal large B cell lymphoma (PMBC), diffuse large B cell lymphoma (DLBCL), follicular lymphoma (FL), transformed follicular lymphoma, splenic marginal zone lymphoma (SMZL), cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemia, acute myeloid leukemia, chronic myeloid leukemia, acute lymphoblastic leukemia (ALL) (including non T cell ALL), chronic lymphocytic leukemia (CLL), solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, other B cell malignancies, and any combination thereof.

E59. The method of any one of E1 to E58, wherein the T cell therapy comprises engineered CAR cell therapy or engineered TCR cell therapy.

E60. The method of E59, wherein the engineered CAR cell or engineered TCR cell therapy treats a tumor in a subject.

EXAMPLES

Example 1

Figure 1B:
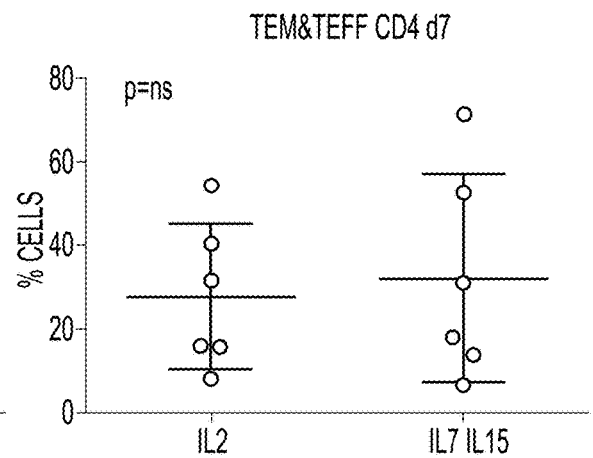
Figure 1C:
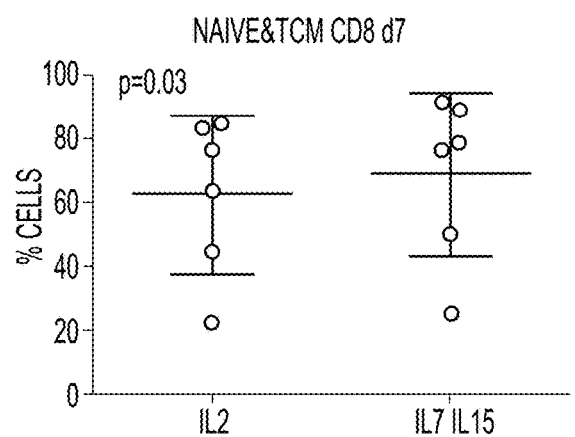
Figure 1D:
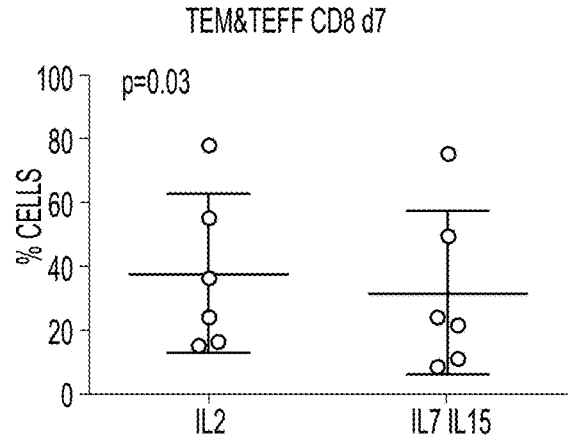
Figure 1E:
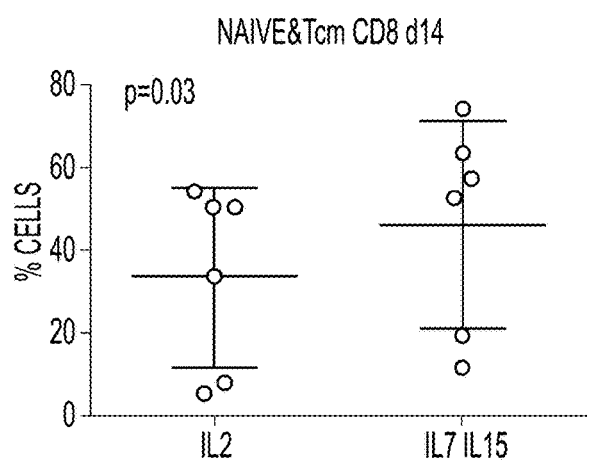
Figure 1F:
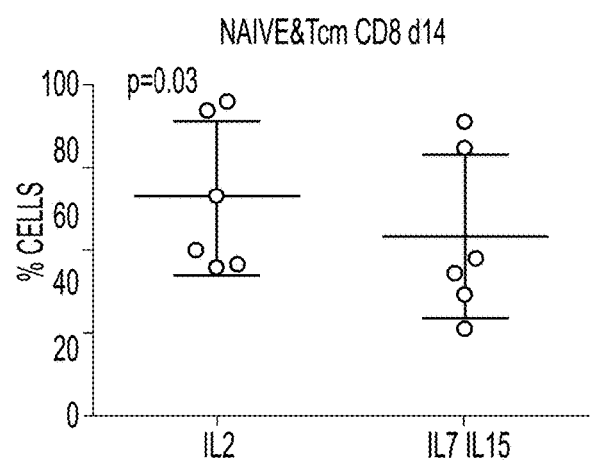

Donor T cells were cultured in the presence of IL-2, IL-7, IL-15, and/or an AKT inhibitor for 10 days, at equal plating concentrations. The T cell phenotype of the cultured T cells was determined for $CD4^+$ T cells and $CD8^+$ T cells cultured for 7 and 14 days in (i) IL-2 alone as compared to IL-7 and IL-15 and (ii) cultured in IL-7 and IL-15 as compared to IL-7, IL-15, and an AKT inhibitor (FIG. 1A-FIG. 1F). A trend towards more juvenile T-cells was observed when cells were grown in the presence of IL-7 and IL-15. In particular, a significantly higher ($p=0.03$, $n=6$) percent of naïve and Tcm cells $CD4^+$ was observed in IL-7/IL-15 treated cells as compared to IL-2 treated cells (FIG. 1A), whereas no difference was observed in the percent of more mature effector T cells (FIG. 1B). This effect was not maintained after long term culture in the $CD4^+$ compartment (data now shown). A similar effect was observed in the $CD8^+$ compartment, with a significantly higher ($p=0.03$, $n=6$) percent of naïve and Tcm cells (FIG. 1C) and a significantly lower ($p=0.03$, $n=6$) percent of effector T cells (FIG. 1D) in the IL-7/IL-15 treated cell culture as compared to the IL-2 treated cell culture. However, unlike in the $CD4^+$ compartment, this affect was observed after long term culture in the $CD8^+$ compartment (FIG. 1E, $p=0.03$, $n=6$; and FIG. 1F, $p=0.03$, $n=6$).

Figure 2A:
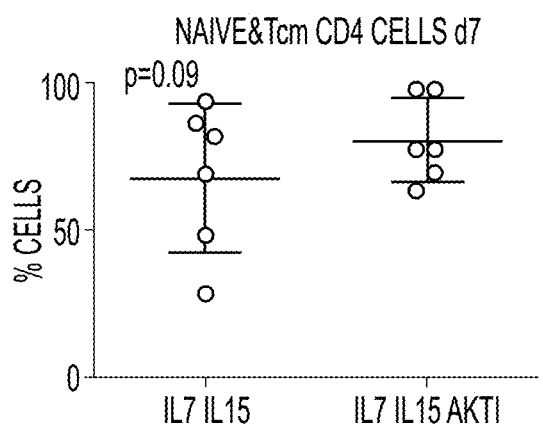
FIG. 2A to FIG. 2D show the phenotype of CD4$^+$ T cells and CD8+ T cells following culture in the presence of IL-7 and IL-15 or in the presence IL-7, IL-15, and AKTi at 7 and 14 days.
Figure 2B:
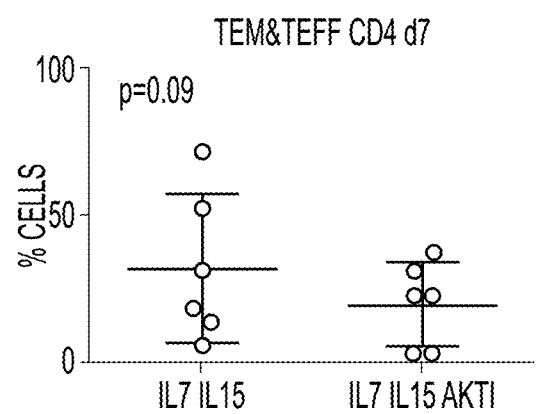
Figure 2C:
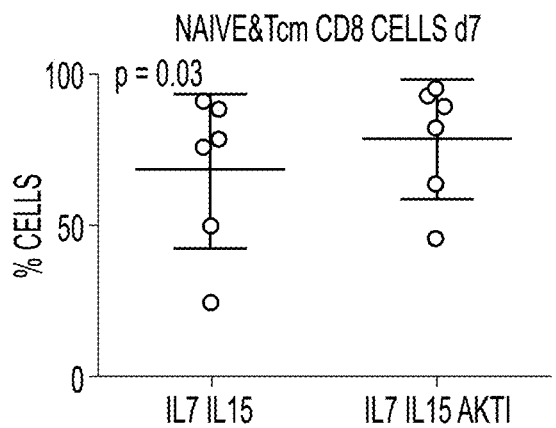
Figure 2D:
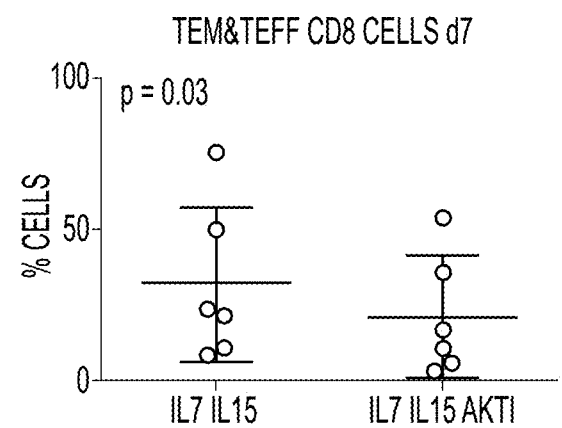

In both the $CD4^+$ and $CD8^+$ compartments, addition of an AKT inhibitor further increased the trend towards more immature T cells. A slightly higher percent of naïve and Tcm $CD4^+$ cells was observed in IL-7/IL-15/AKTi treated cells as compared to IL-7/IL-15 treated cells (FIG. 2A), and a slightly lower percent of effector T cells was observed in IL-7/IL-15/AKTi treated cells as compared to IL-7/IL-15 treated cells (FIG. 2B) at day 7. No significant difference was observed in cells cultured for 14 days (data not shown). However, a significant difference was observed in the CD8$^+$ compartment at day 7. In particular, the percent of naïve and Tcm CD4$^+$ cells was significantly higher (p=0.03, n=6) in IL-7/IL-15/AKTi treated cells as compared to IL-7/IL-15 treated cells (FIG. 2C), and the percent of effector T cells was significantly lower (p=0.03, n=6) in IL-7/IL-15/AKTi treated cells as compared to IL-7/IL-15 treated cells (FIG. 2D) at day 7. However, this effect was not observed at day 14 (data not shown).

Figure 3B:
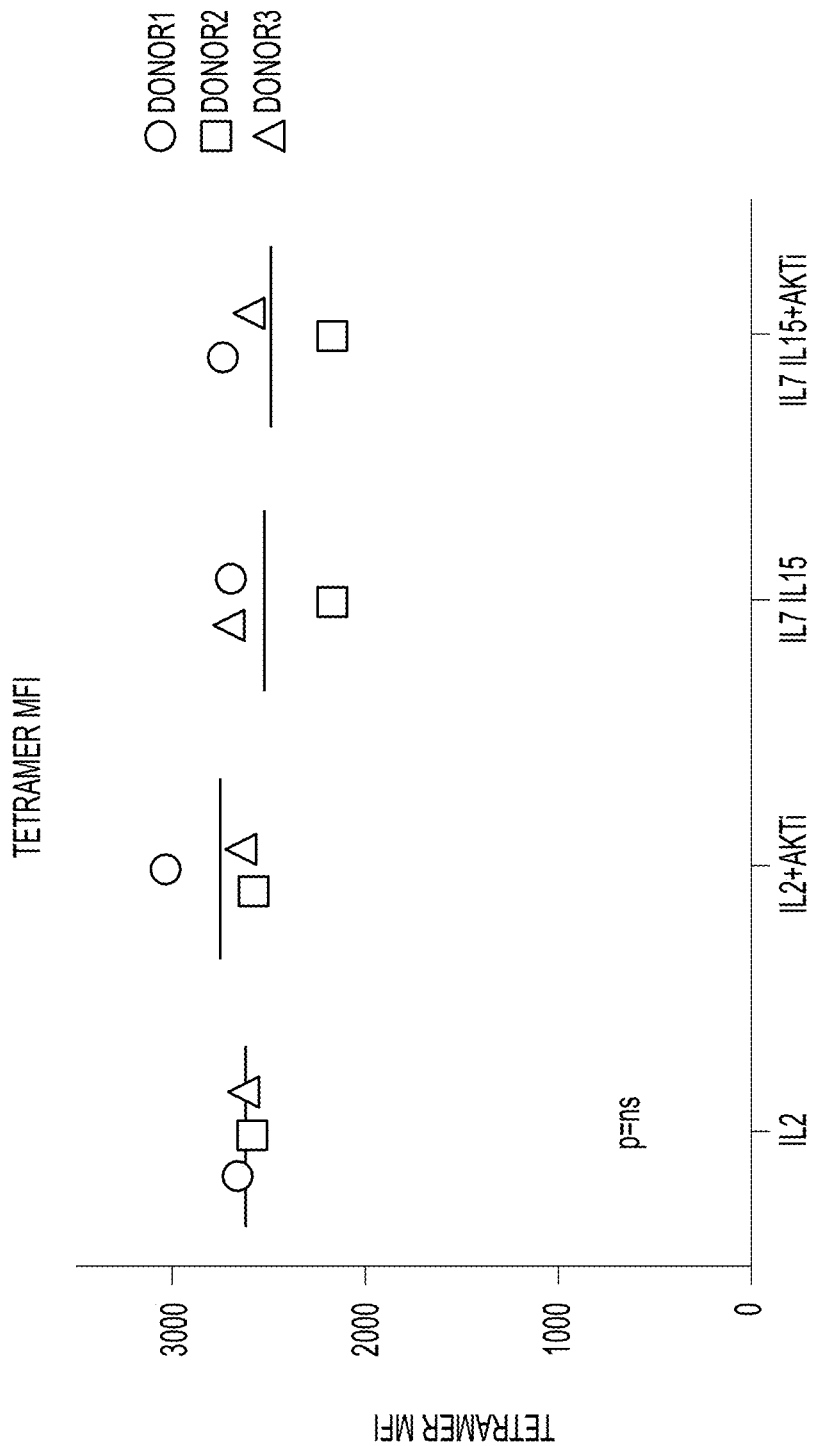
FIG. 3B shows tetramer mean fluorescence intensity (MFI) for cells from Donor 1 (circles), Donor 2 (squares), and Donor 3 (triangles), following culture in the presence of IL-2 alone; IL-2 and AKTi; IL-7 and IL-15; and IL-7, IL-15, and AKTi. A statistical analysis indicated that any differences in tetramer MFI were not significant (p=ns).

To determine whether contacting T cells with one or more of IL-2, IL-7, and/or IL-15 and an AKT inhibitor has an effect on transduction efficiency, T cells collected from 3 donors were transduced with a retrovirus carrying a Class I TCR in an OriGen PERMALIFE™ PL30 bag two days after stimulation. Transduced cells were then cultured in the presence of (i) IL-2; (ii) IL-2 and an AKT inhibitor; (iii) IL-7 and IL-15; and (iv) IL-7, IL-15, and an AKT inhibitor for 10 days. T cells were then analyzed for CD3 expression and positive soluble MHC-tetramer staining (Tet$^+$), an indicator of successful transduction. No major differences were observed in transduction efficiencies depending on the culture conditions (FIG. 3A), and no significant differences were observed in tetramer mean fluorescence intensity (MFI) across the culture conditions (FIG. 3B).

Example 2

The effects of AKTi inhibitors on cell expansion were investigated under various conditions. First, the effect of AKTi culture conditions on various sources of donor cells was evaluated as follows. Apheresis products from four healthy donors were processed using high density centrifugation to obtain peripheral blood mononuclear cells (PBMCs) (FIGS. 4A-4D). Cells from four donors were counted and stimulated using OKT3 (a monoclonal antibody to CD3), and cultured in the presence of IL-2 (circles); IL-2 and AKTi (squares); IL-7 and IL-15 (triangles); or IL-7, IL-15, and AKTi (inverted triangles) for 7 to 10 days (FIGS. 4A-4D). Cell expansion was observed for each donor cell line under each culture condition, and AKTi had no negative impact on cell expansion (FIGS. 4A-4D).

Figure 5A:
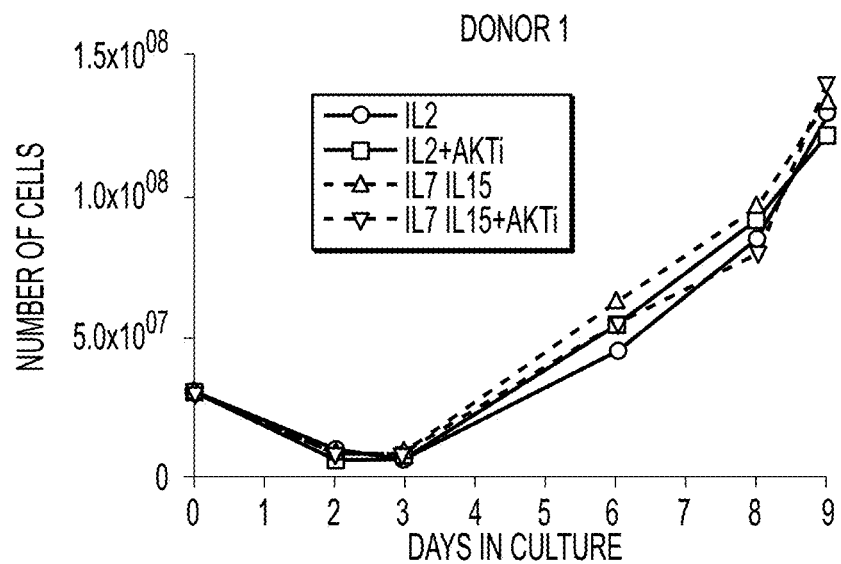
FIGS. 5A-5C show cell expansion over the course of 9 days for cells from three donors transduced with a class I TCR (HPV-E6) and cultured in the presence of IL-2 (circles); IL-2 and AKTi (squares); IL-7 and IL-15 (triangles); or IL-7, IL-15, and AKTi (inverted triangles). Each of FIGS. 5A-5C represents cell expansion for a single donor cell line. Source material for expansion protocol were peripheral blood mononuclear cells.
Figure 5B:
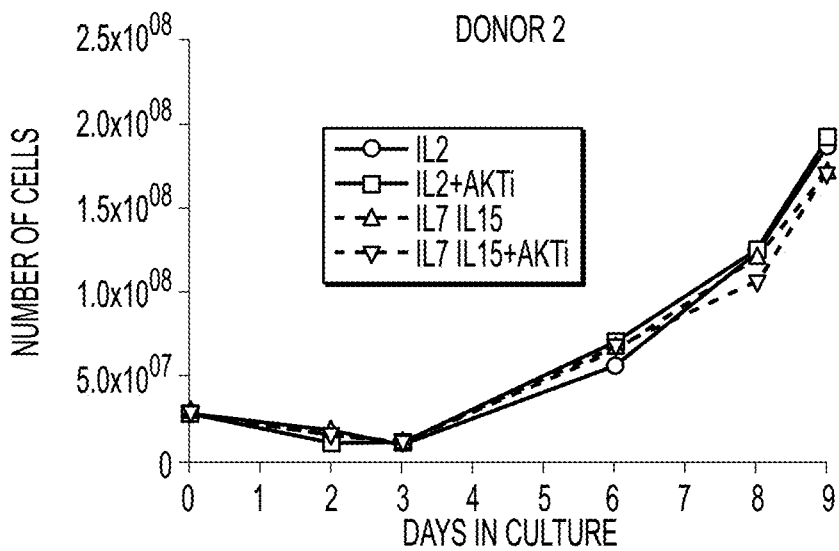
Figure 5C:
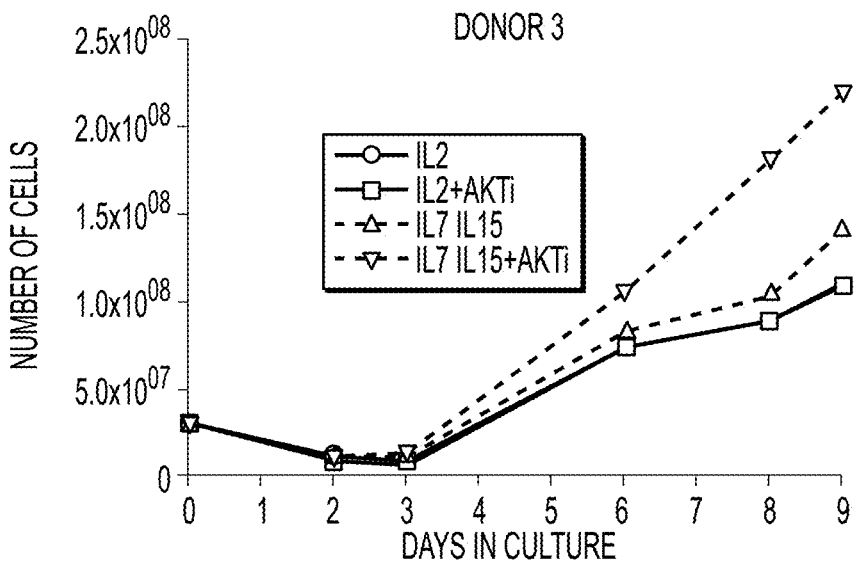

Next, class I TCR transduced (HPV-E6) PBMCs were evaluated. Apheresis products from three healthy donors were again processed using high density centrifugation to obtain PBMC, counted, and stimulated using OKT3. Cells from three donors were then cultured in the presence of IL-2 (circles); IL-2 and AKTi (squares); IL-7 and IL-15 (triangles); or IL-7, IL-15, and AKTi (inverted triangles) (FIGS. 5A-5C). On day 2, the cells were transduced with a class I TCR (HPV-E6). Cell expansion was observed for each donor cell line under each culture condition, and AKTi had no negative impact on cell expansion (FIGS. 5A-5C).

Figure 6A:
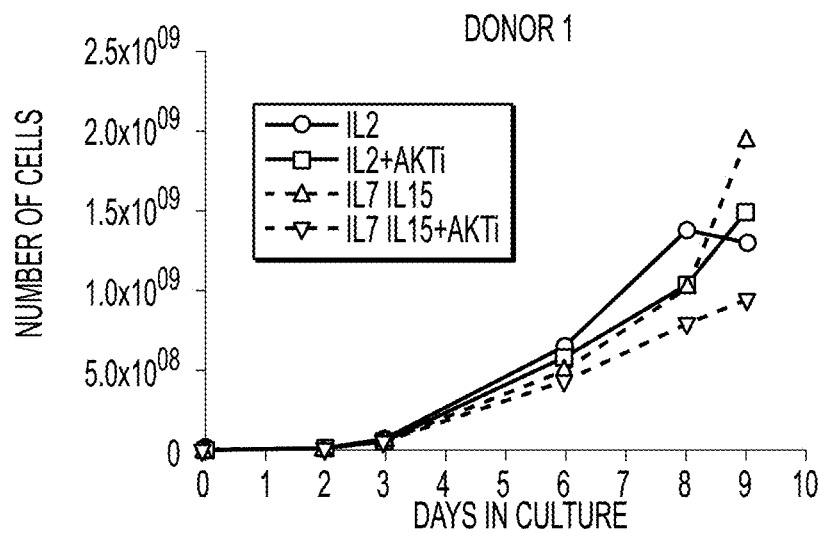
FIGS. 6A-6C show cell expansion over the course of 10 days for isolated CD4$^+$ and CD8$^+$ cells from three donors transduced with a class II TCR (MAGE-A3) and cultured in the presence of IL-2 (circles); IL-2 and AKTi (squares); IL-7 and IL-15 (triangles); or IL-7, IL-15, and AKTi (inverted triangles). Each of FIGS. 6A-6C represents cell expansion for a single donor cell line.
Figure 6B:
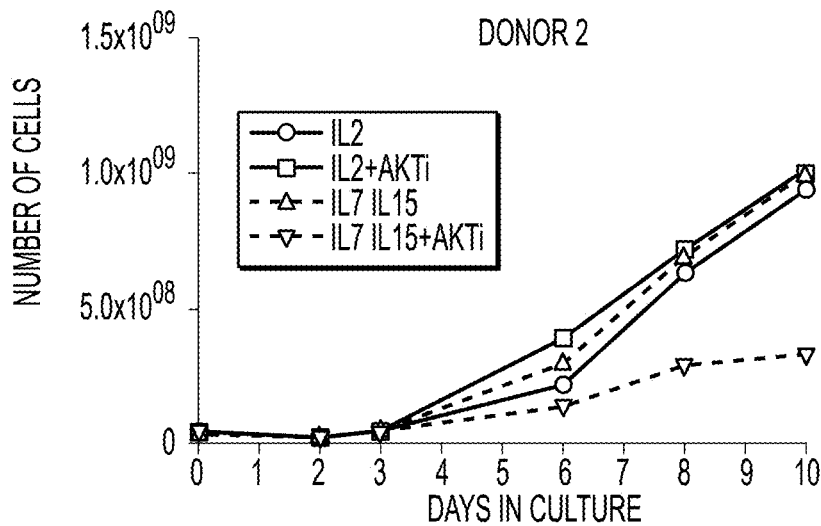
Figure 6C:
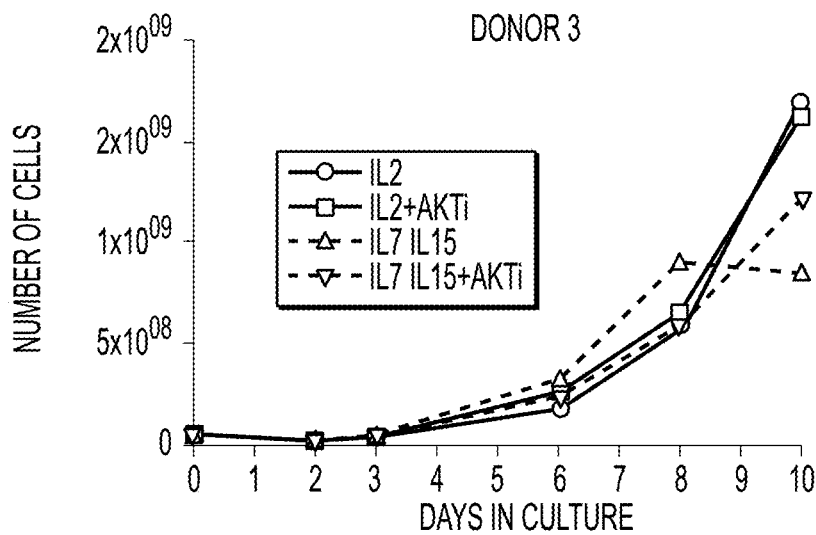

Next, the effect of AKTi culture conditions on CD4$^+$/CD8$^+$ T cells was evaluated. Apheresis products from three healthy donors were again processed using high density centrifugation to obtain PBMCs. PBMCs were then cultured with anti-CD4 and anti-CD8 Ab beads, and CD4$^+$ and CD8$^+$ cells were selected using the CLINIMACS® system (Miltenyi Biotec). CD4$^+$ and CD8$^+$ cells from three donors were counted, stimulated using OKT3 and anti-CD28 Ab. The cells were then cultured in the presence of IL-2 (circles); IL-2 and AKTi (squares); IL-7 and IL-15 (triangles); or IL-7, IL-15, and AKTi (inverted triangles) (FIGS. 6A-6C). Cells were transduced with a class II TCR (MAGE-A3) on day 2. Cell expansion was observed for each donor cell line under each culture condition, and AKTi had no negative impact on cell expansion (FIGS. 6A-6C).

Figure 7A:
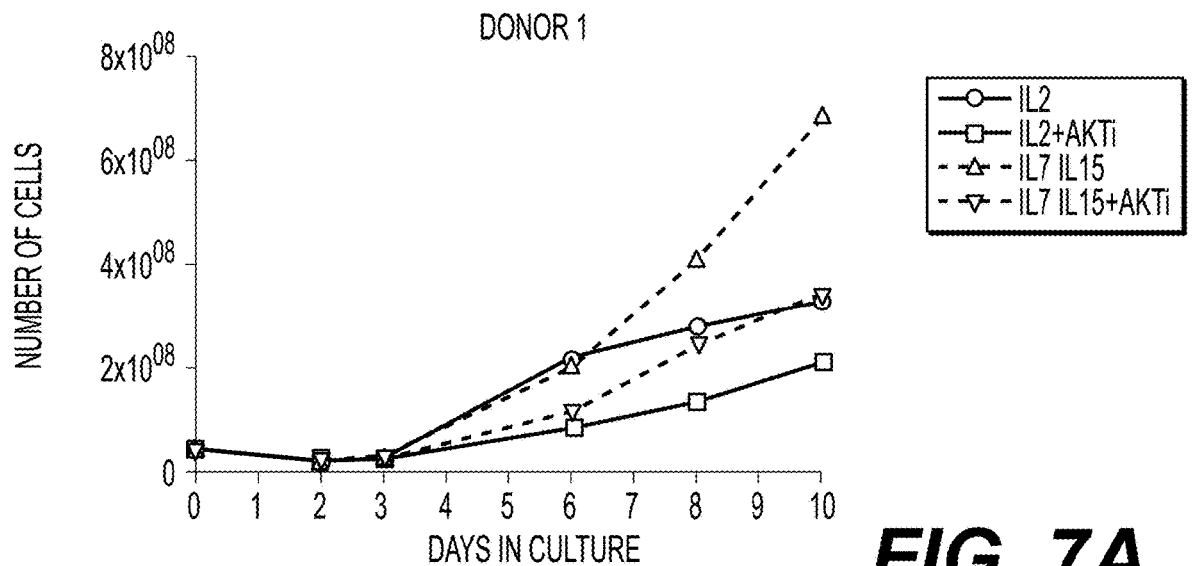
FIGS. 7A-7C show cell expansion over the course of 10 days for isolated CD4$^+$ cells from three donors transduced with a class II TCR (MAGE-A3) and cultured in the presence of IL-2 (circles); IL-2 and AKTi (squares); IL-7 and IL-15 (triangles); or IL-7, IL-15, and AKTi (inverted triangles). Each of FIGS. 7A-7C represents cell expansion for a single donor cell line.
Figure 7B:
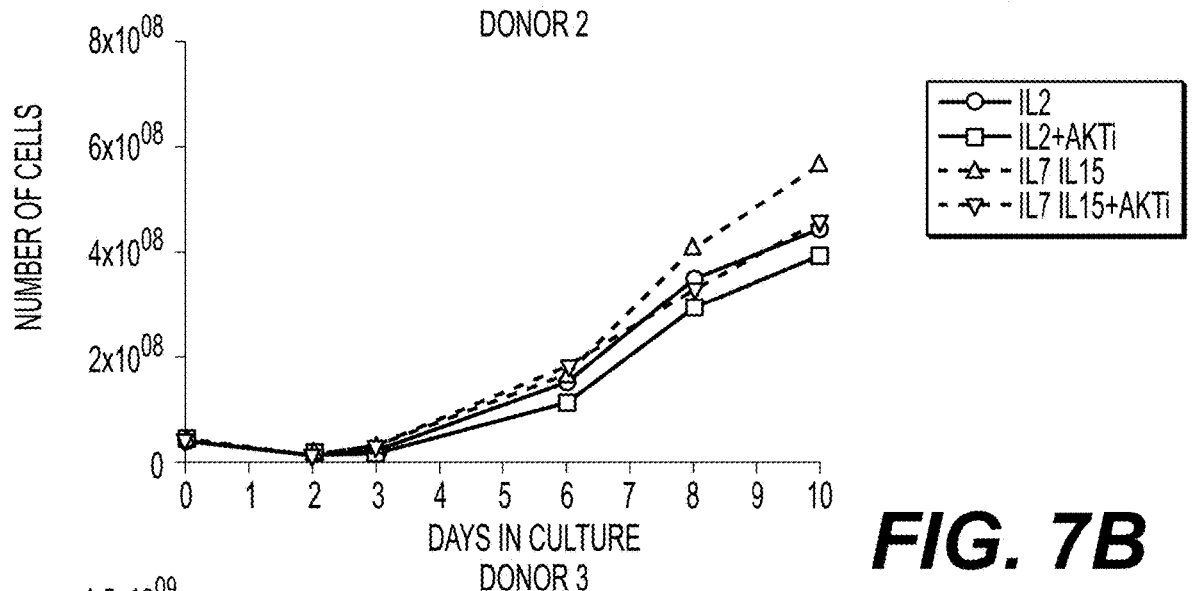
Figure 7C:
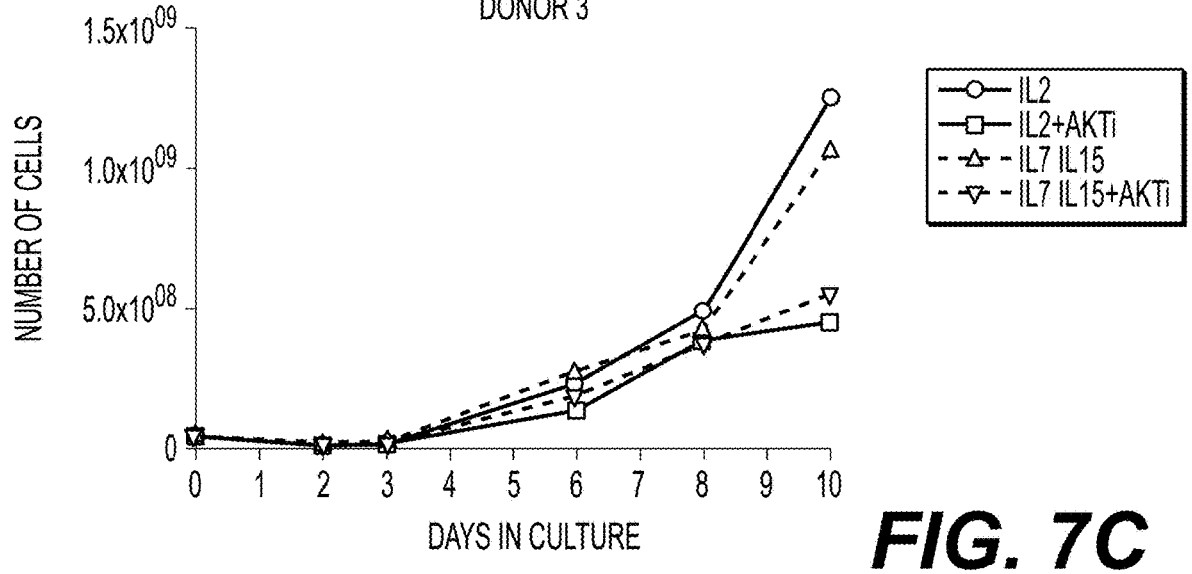
Figure 8A:
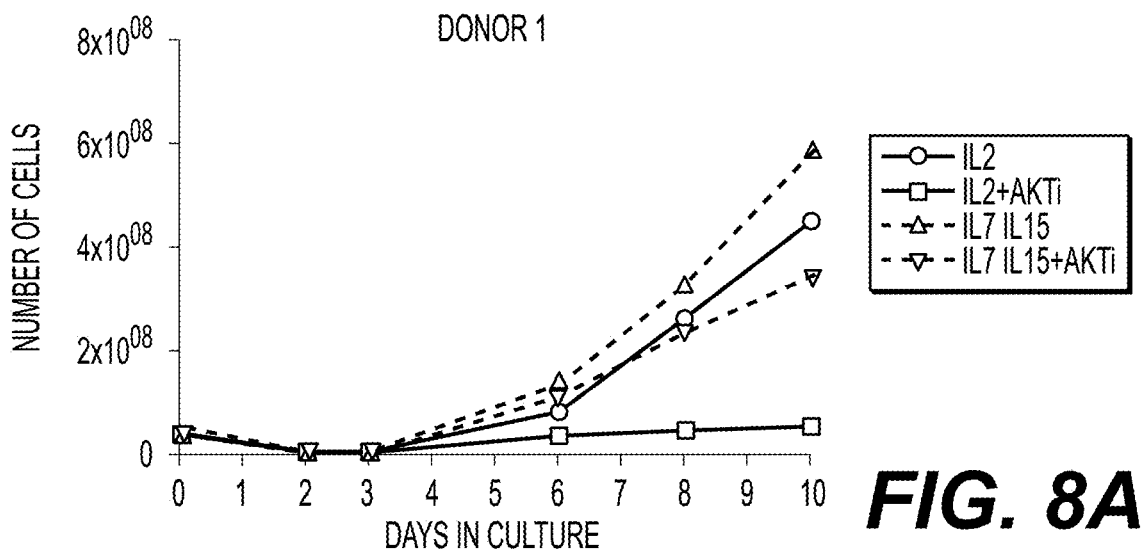
FIGS. 8A-8C show cell expansion over the course of 10 days for isolated CD8$^+$ cells from three donors transduced with a class II TCR (MAGE-A3) and cultured in the presence of IL-2 (circles); IL-2 and AKTi (squares); IL-7 and IL-15 (triangles); or IL-7, IL-15, and AKTi (inverted triangles). Each of FIGS. 8A-8C represents cells from a single donor cell line.
Figure 8B:
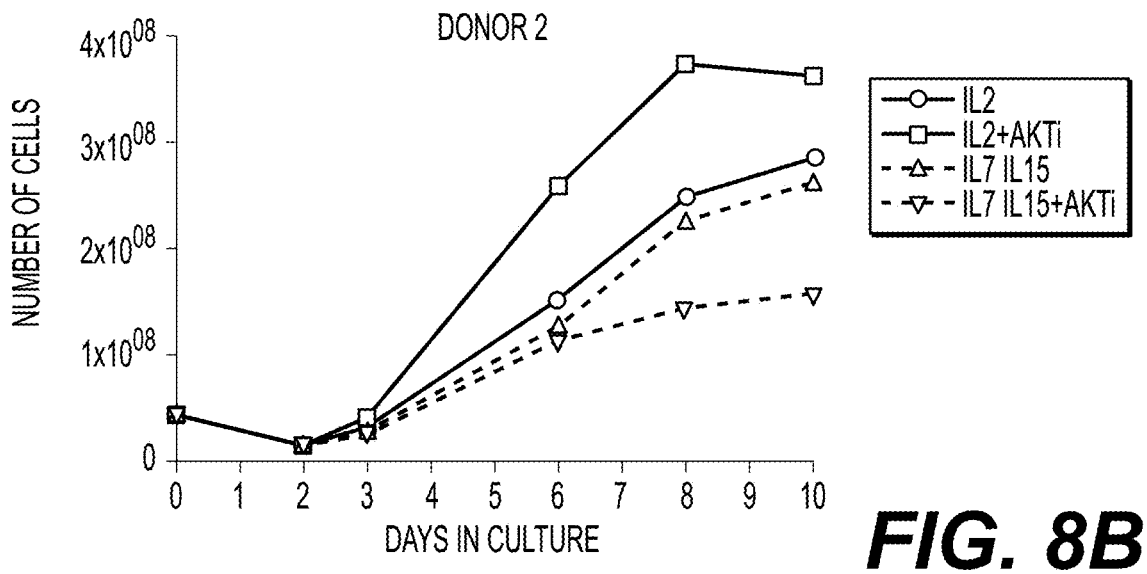
Figure 8C:
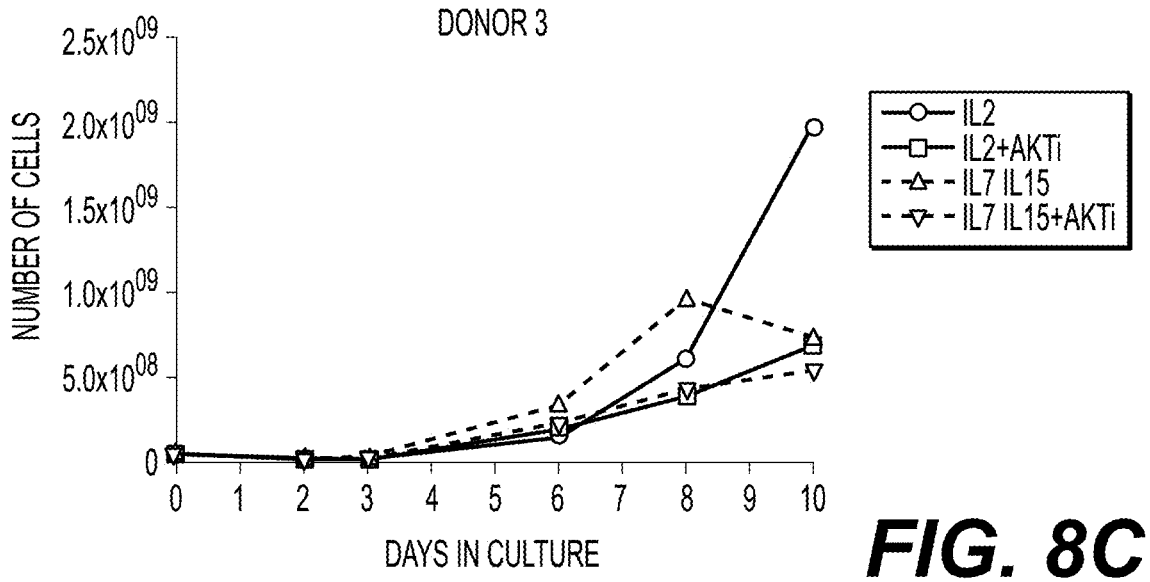

CD4+ and CD+ T cells were then separately evaluated. Apheresis products from three healthy donors were again processed using high density centrifugation to obtain PBMCs. PBMCs were then cultured with either anti-CD4 beads (FIGS. 7A-7C) or anti-CD8 beads (FIGS. 8A-8C), and target cells were selected using the CLINIMACS® system (Miltenyi Biotec). Cells from three donors were then counted and stimulated using OKT3 and anti-CD28 Ab. The cells were then cultured in the presence of IL-2 (circles); IL-2 and AKTi (squares); IL-7 and IL-15 (triangles); or IL-7, IL-15, and AKTi (inverted triangles). Cells were transduced with a class II TCR (MAGE-A3) on day 2. Cell expansion was observed for CD4$^+$ (FIGS. 7A-7C) and CD8$^+$ (FIGS. 8A-8C) cells from each donor cell line under each culture condition, and AKTi had no negative impact on cell expansion.

Figure 9A:
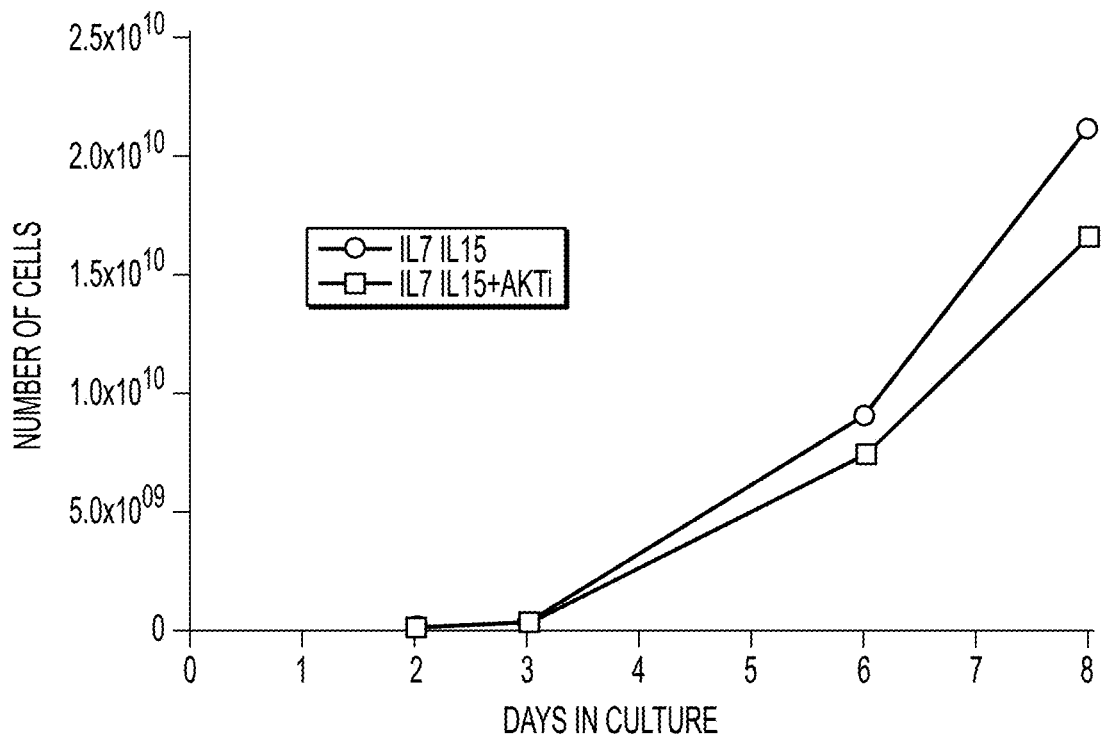
FIGS. 9A-9D show cell expansion over the course of 8 days for CD4$^+$ and CD8$^+$ cells from three donors transduced with a class II TCR (MAGE-A3). Cells were cultured in the presence of IL-7 and IL-15 (FIG. 9A: circles.
Figure 9B:
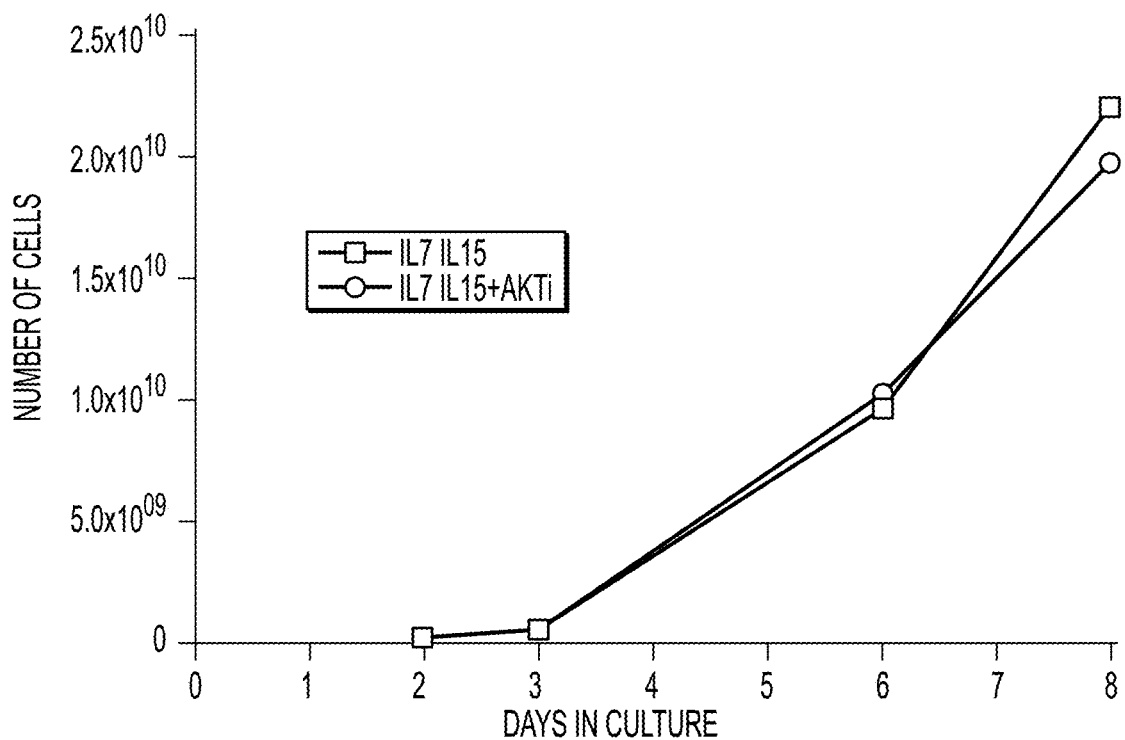
Figure 9C:
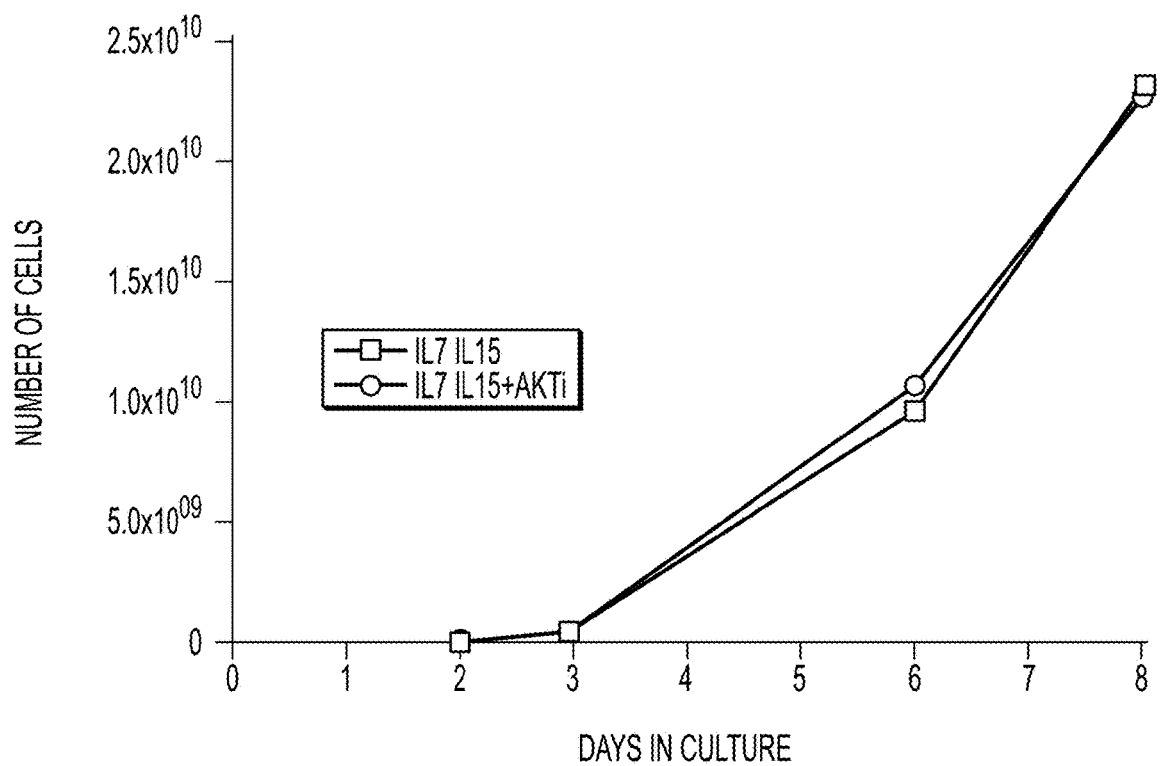
Figure 9D:
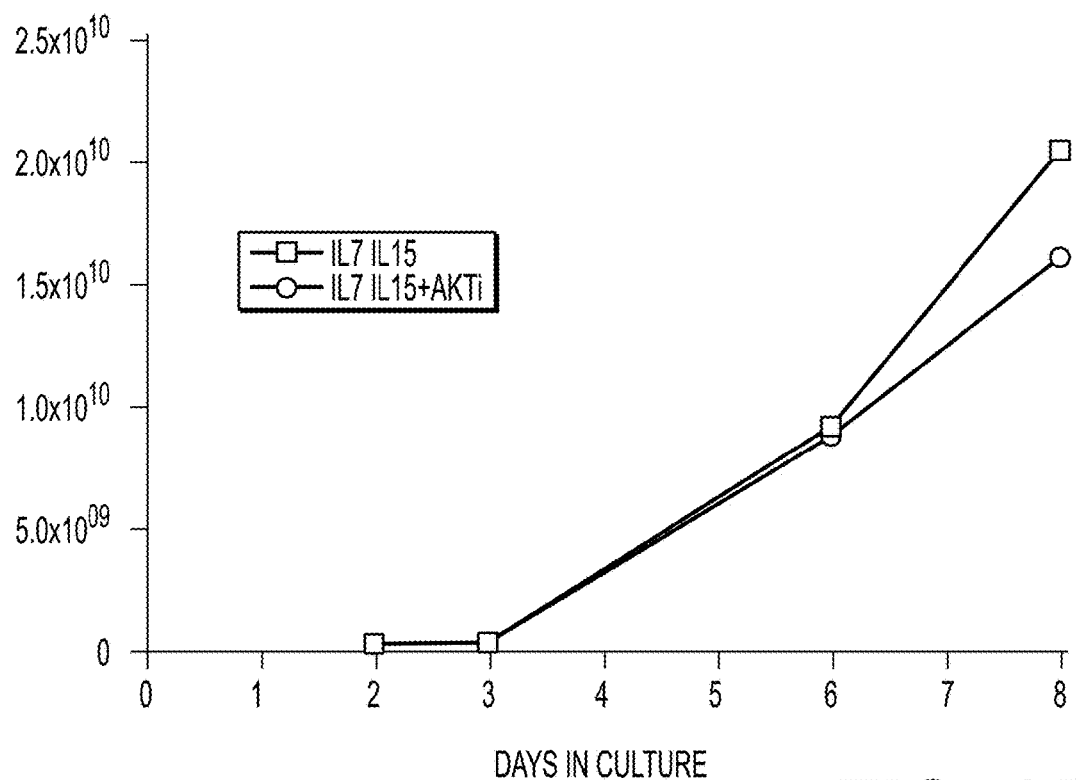
Figure 10:
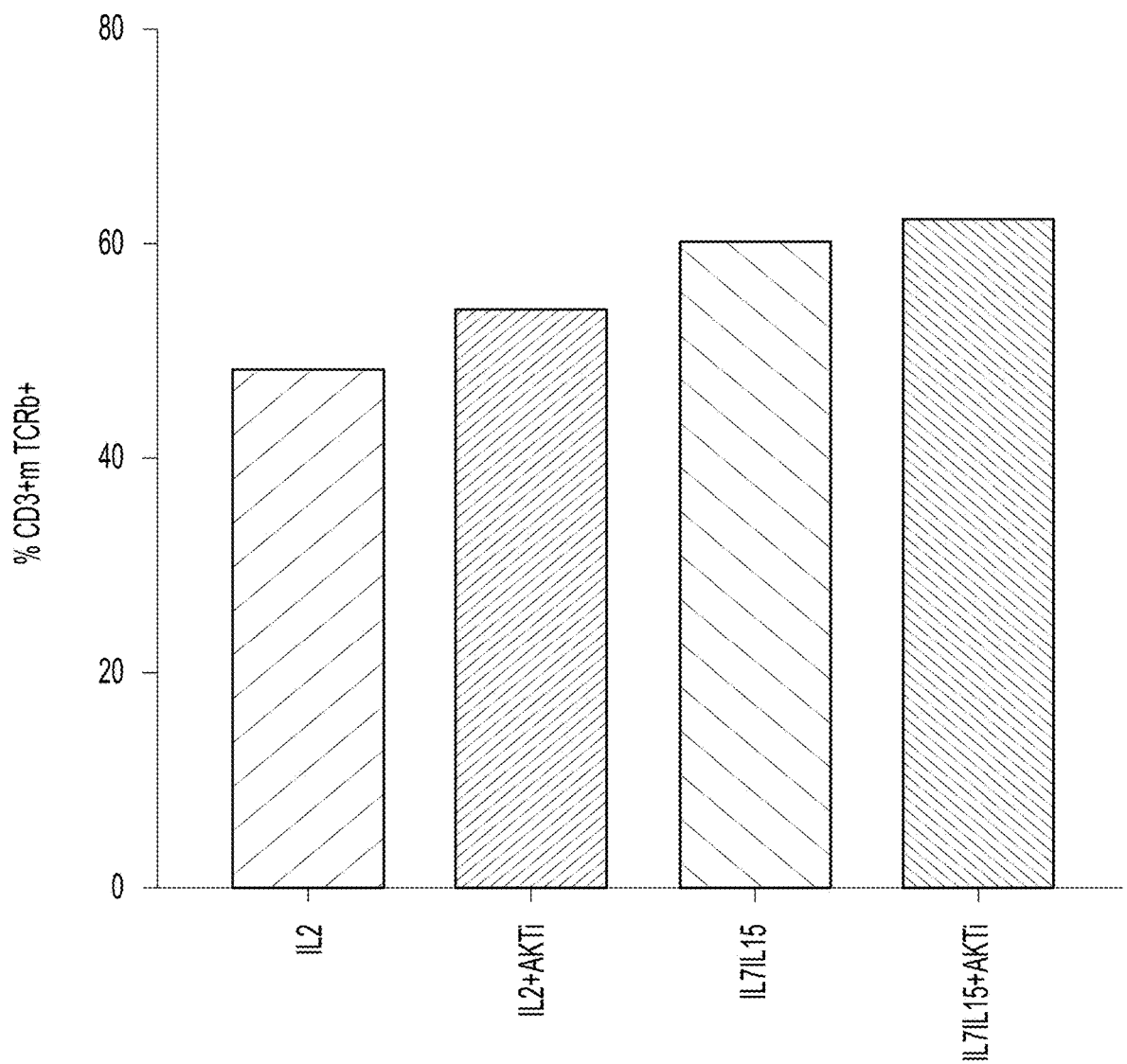
FIG. 10 shows transduction efficiency for T cells transduced with a class I TCR (HPV-E6). Cells were cultured in the presence of IL-2 alone; IL-2 and AKTi; IL-7 and IL-15; or IL-7, IL-15, and AKTi. Cells were transduced on day 2, and transduction efficiency was measured on day 10 by staining the cells with an anti-mTCRb antibody, which specifically recognizes transduced TCR. The percent of cells showing positive anti-mTCRb staining (y-axis) for each culture condition (x-axis) is shown.

The effects of culture conditions during large manufacturing scale culturing were then evaluated. Apheresis products from four healthy donors were again processed using high density centrifugation to obtain peripheral blood mononuclear cells PBMC (FIGS. 9A-9D). PBMC were then cultured with anti-CD4 and anti-CD8 beads, and CD4$^+$/CD8$^+$ cells were selected using the CLINIMACS® system. CD4$^+$/CD8$^+$ cells were counted and stimulated using OKT3 and anti-CD28. Cells were then cultured at large manufacturing scale in a XURI™ Cell Expansion System (GE Healthcare Life Sciences) for 8 days in the presence of IL-7 and IL-15 (FIG. 9A: circles; FIGS. 9B-9C: squares) or IL-7, IL-15, and AKTi (FIG. 9A: squares; FIGS. 9B-9C: circles). Cells were transduced with a class II TCR (MAGE-A3) on day 2 of the culture. Cell expansion was observed for each donor cell line under each culture condition, and AKTi had no negative impact on cell expansion (FIGS. 9A-9D).

Example 3

Figure 11A:
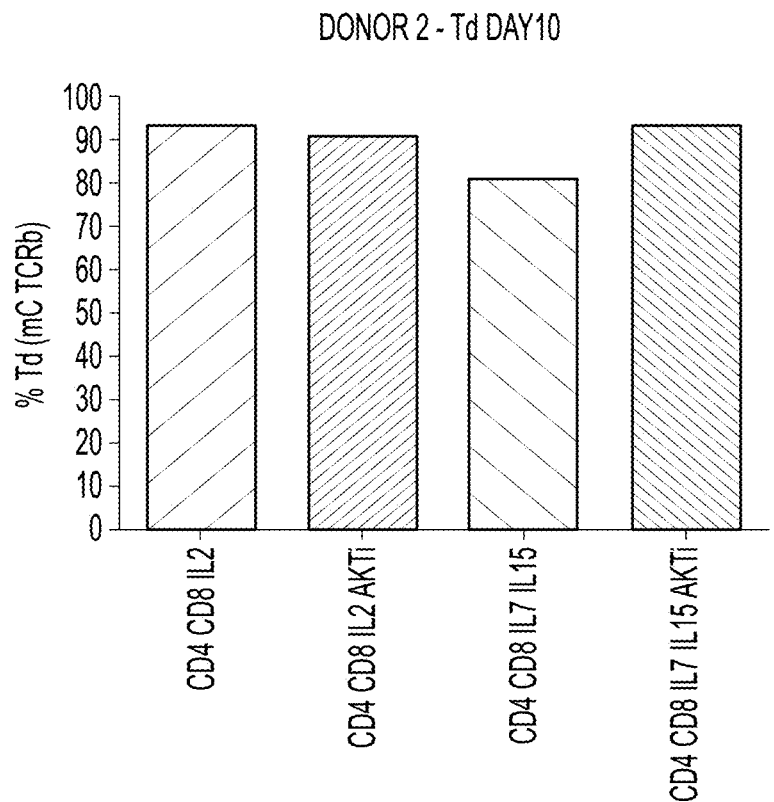
FIGS. 11A-11F show transduction efficiency for T cells transduced with a class II TCR (MAGE-A3) of CD4$^+$/CD8$^+$ T cells from two donors. Cells were cultured in the presence of IL-2 alone; IL-2 and AKTi; IL-7 and IL-15; or IL-7, IL-15, and AKTi. Cells were transduced on day 2, and transduction efficiency was measured on day 10 by staining the cells with an anti-mTCRb antibody (mC TCR PE) (FIGS. 11A and 11D). MFI of the anti-mTCRb staining for each culture condition is shown in FIGS. 11B and 11E.
Figure 11B:
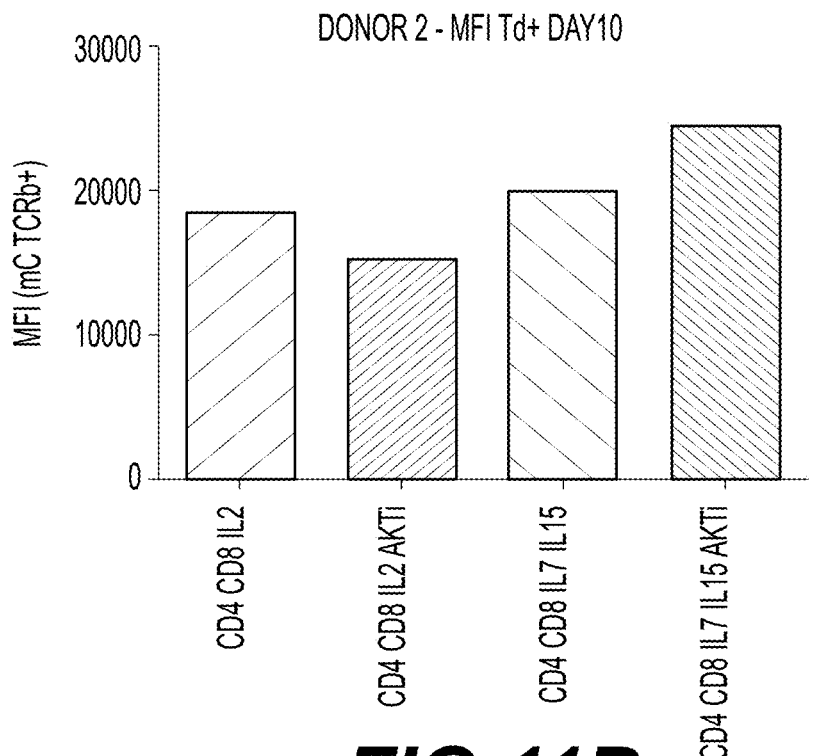
Figure 11C:
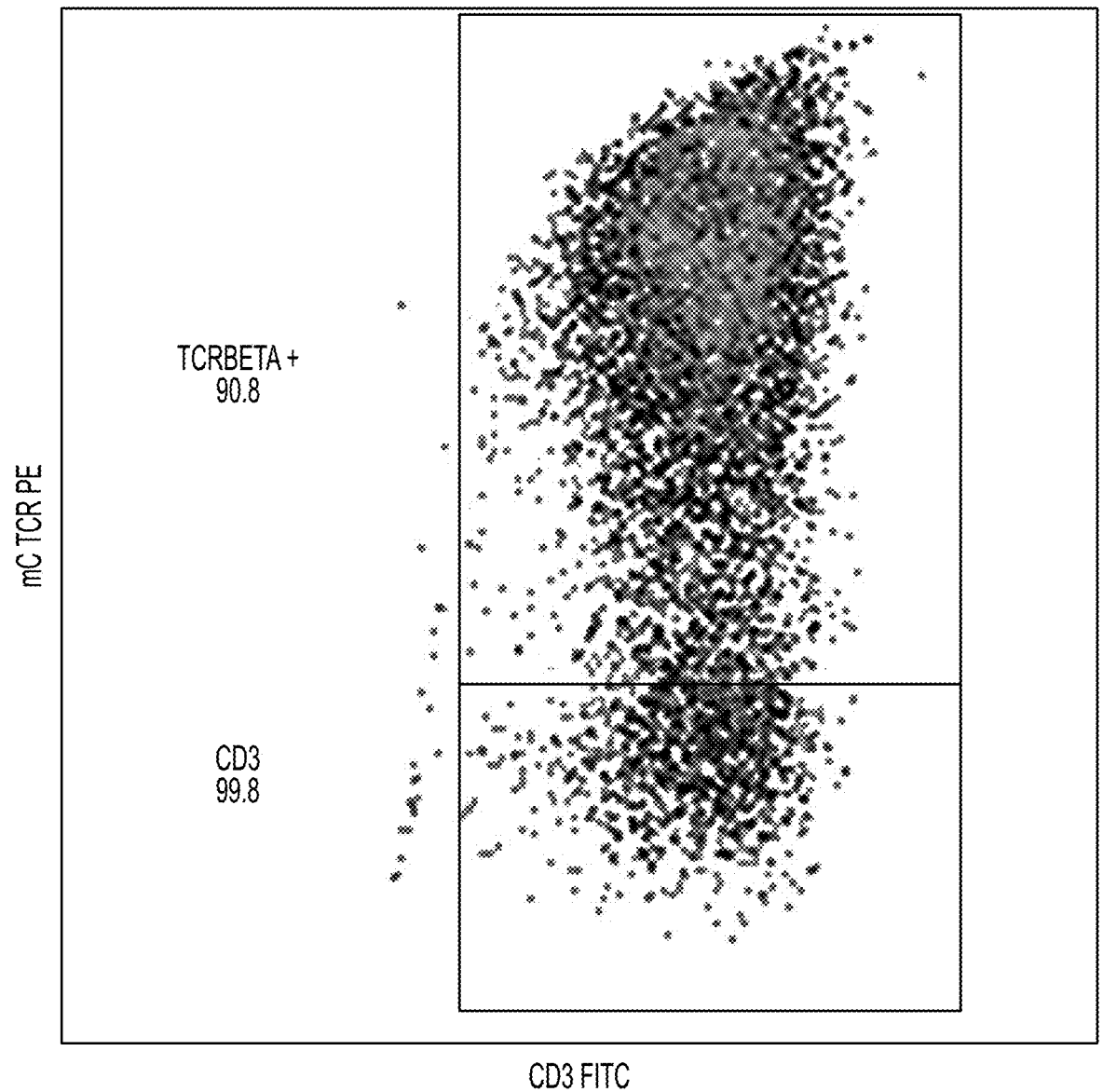
Figure 11D:
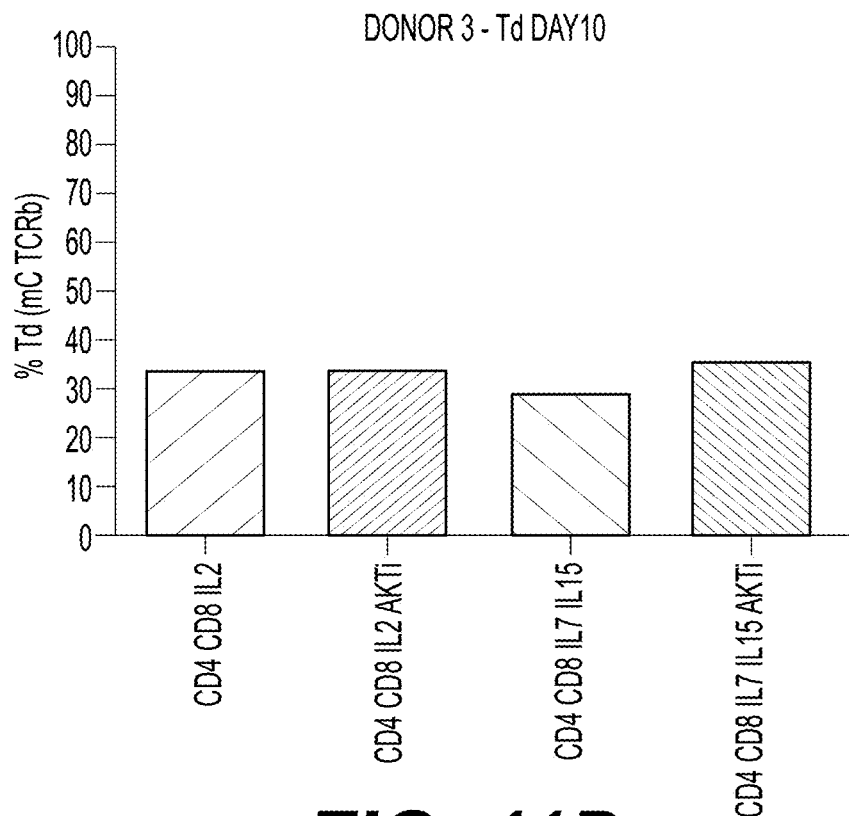
Figure 11E:
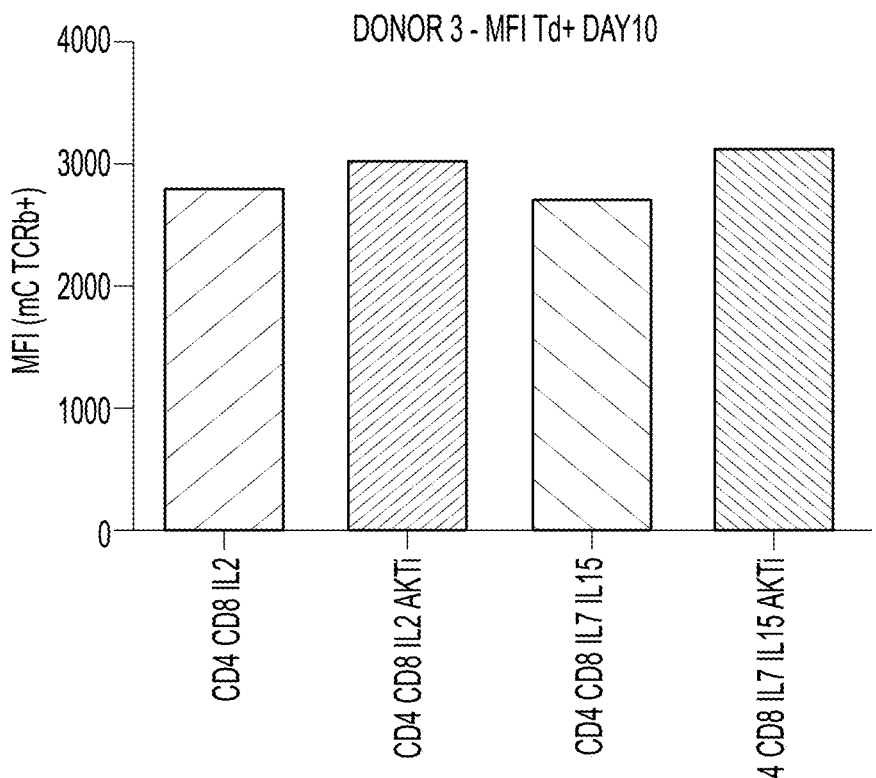
Figure 11F:
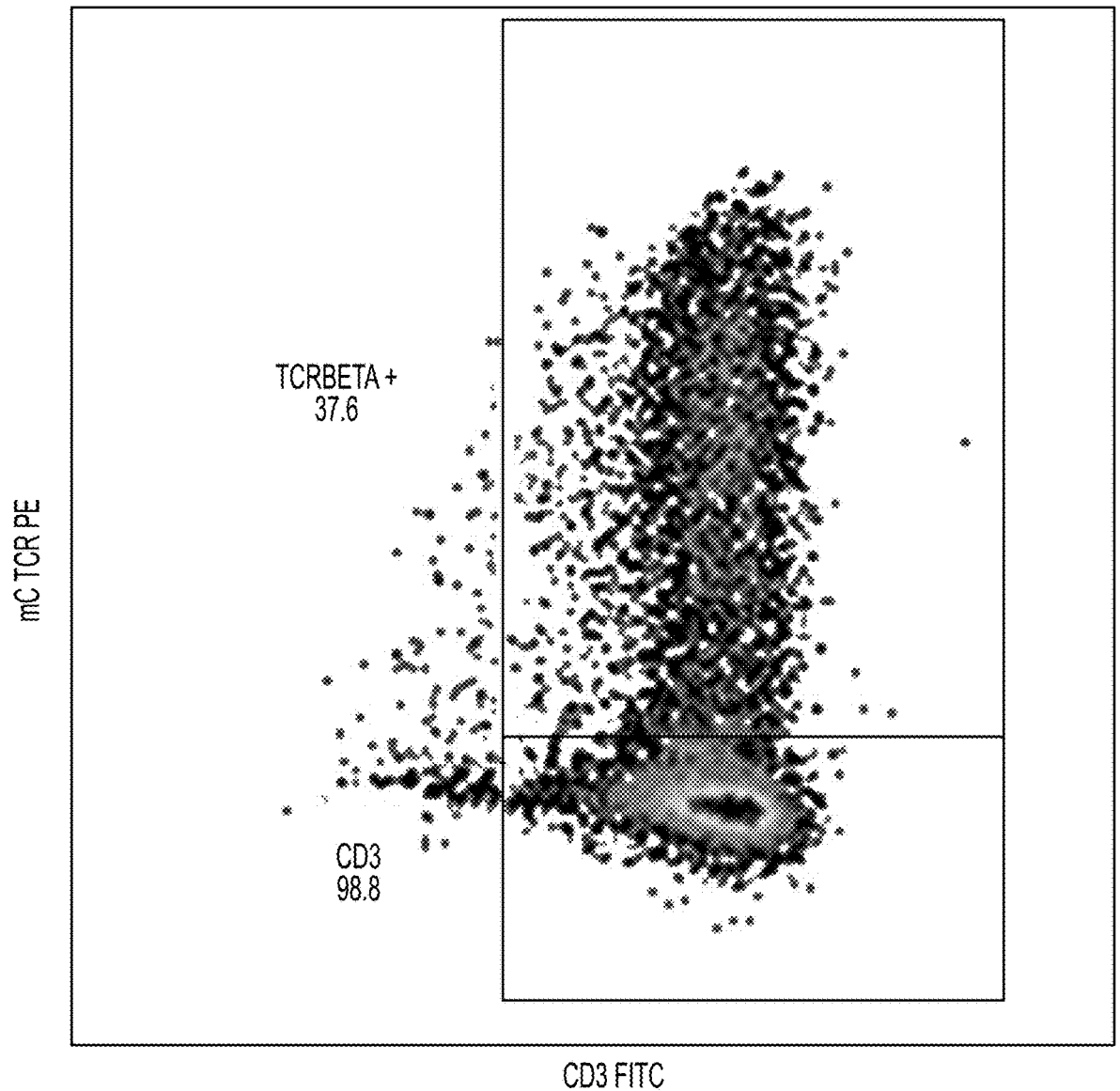

The effect on transduction efficiency of T cells following culture in the presence of AKTi was investigated. Previously frozen donor T cells were stimulated and then cultured for 10 days in the presence of IL-2, IL-2 and AKTi; IL-7 and IL-15; or IL-7, IL-15, and AKTi. The cells were transduced on day 2 post-stimulation with a class I TCR (HPV-E6) in a T-75 tissue culture flask (FIG. 10) or with a class II TCR (MAGE-A3) in OriGen PERMALIFE™ bags (FIGS. 11A-11F). T cell transduction efficiency was measured by anti-mTCRb antibody staining at day 10 (FIGS. 10 and 11A-11F). AKTi had no negative impact on transduction efficiency (FIGS. 10, 11A, 11B, 11D, and 11E), though the anti-mTCRb staining MFI shows slightly greater overall intensity for cells cultured in the presence of IL-7, IL-15, and AKTi, relative to IL-7 and IL-15 alone (FIGS. 11C and 11F).

Figure 12:
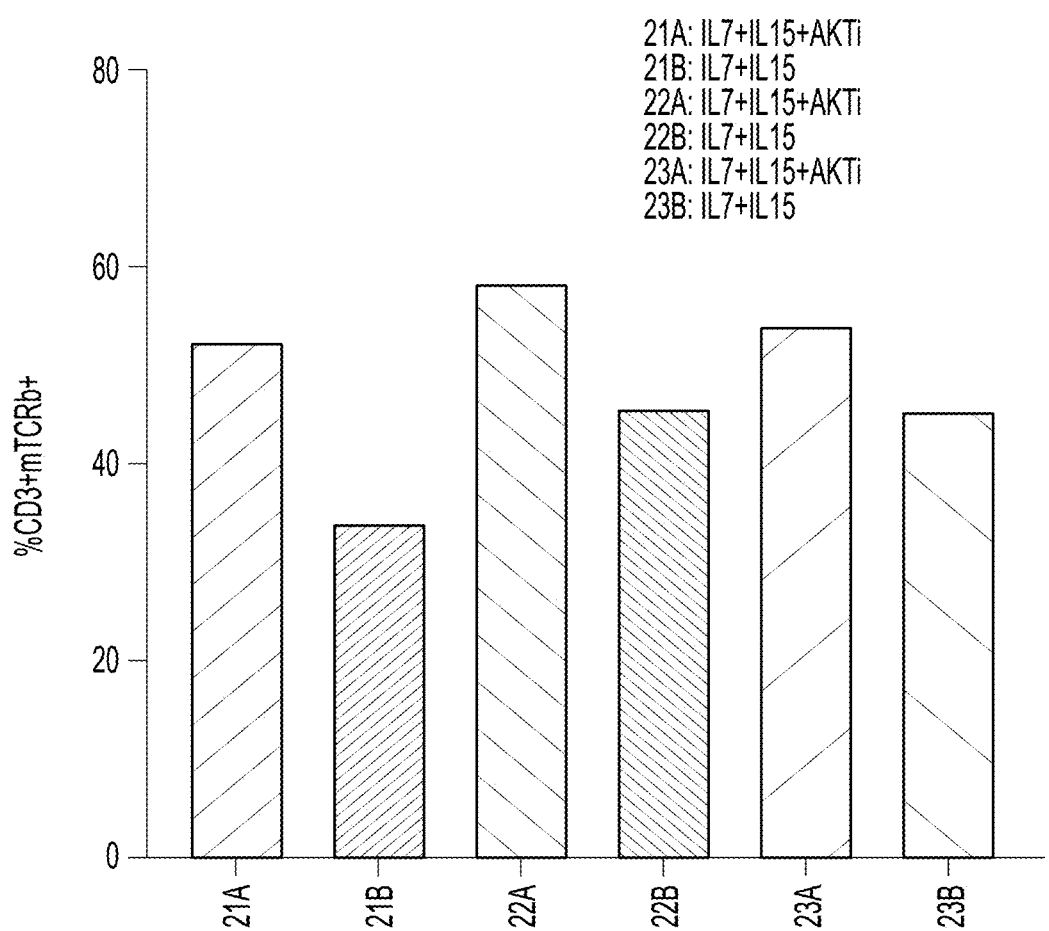
FIG. 12 shows transduction efficiency for T cells transduced with a class II TCR (MAGE-A3) for T cells from four manufacturing scale runs (16, 21, 22, and 23). For each run, cells were divided into two culture conditions: addition of IL-7 and IL-15 and addition of IL-7, IL-15, and AKTi, as indicated. Transduction efficiency was measured by staining the cells with an anti-mTCRb antibody (mC TCR PE). The percent of cells showing positive anti-mTCRb staining (y-axis) for each run (x-axis) is shown.

Similar results were observed for T cells cultured on a manufacturing scale (FIG. 12). Previously frozen donor T cells from four manufacturing scale runs (21, 22, and 23) were cultured in OriGen PERMALIFE™ bags in the presence of IL-7 and IL-15 or IL-7, IL-15, and AKTi. Cells were transduced on day 2 post-stimulation with a class II TCR (MAGE-A3). Cells were then grown in a XURI™ Bioreactor Cell Expansion System. T cell transduction efficiency was determined at day 8 by anti-mTCRb (mC TCR PE) antibody staining. The percent of CD3$^+$ cells expressing the transduced TCR for each culture condition for each run are shown (FIG. 12). Under large scale manufacturing conditions, cells grown in the presence of IL-7, IL-15, and AKTi have a greater transduction efficiency than cells cultured in IL-7 and IL-15 alone (FIG. 12).

Example 4

Figure 13A:
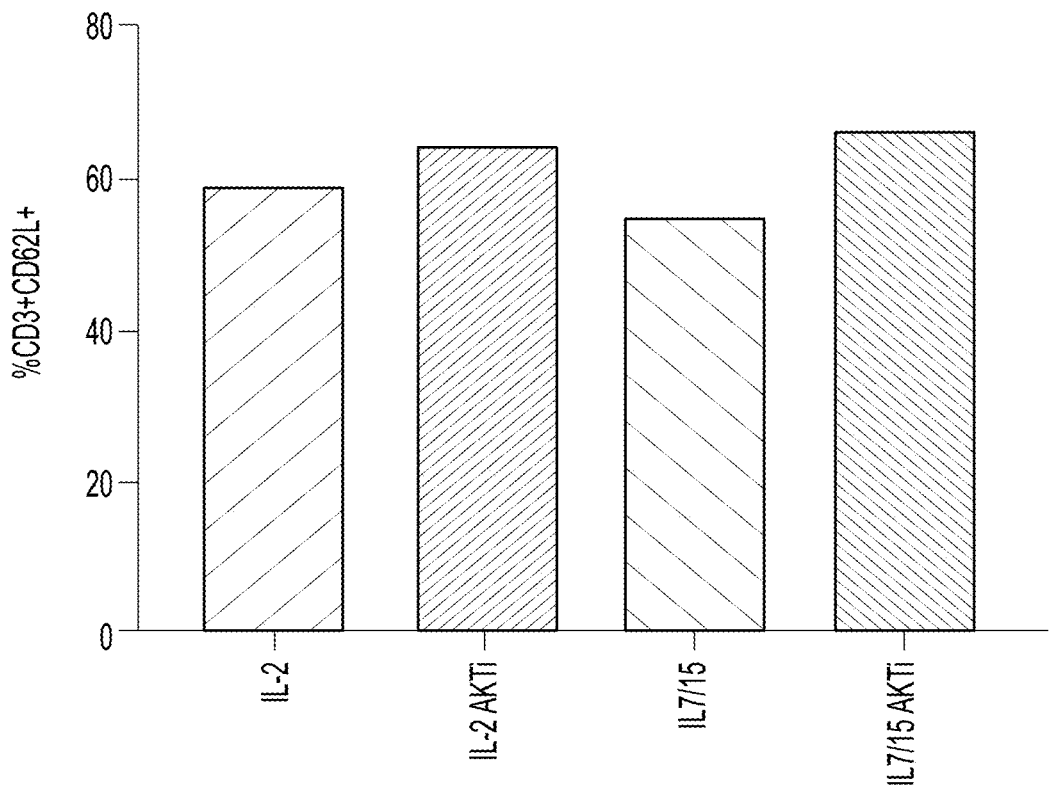
FIGS. 13A-13F show the differentiation status of CD4$^+$/CD8$^+$ T cells transduced with a class II TCR (MAGE-A3) and cultured under various conditions with and without AKTi. T cells from Donor 1 (FIGS. 13A and 13D), Donor 2 (FIGS. 13B and 13E), and Donor 3 (FIGS. 13C and 13E) were cultured in the presence of IL-2 alone; IL-2 and AKTi; IL-7 and IL-15; or IL-7, IL-15, and AKTi, and then stained for CD62L expression, a marker of cells in early stages of differentiation. The percent of CD3$^+$ and CD62L$^+$ cells (y-axis) for each culture condition (x-axis) for each donor are presented in FIGS. 13A-13C. The MFI of CD62L staining (y-axis) for each culture condition (x-axis) for each donor cell line is shown in FIGS. 13D-13E.
Figure 13B:
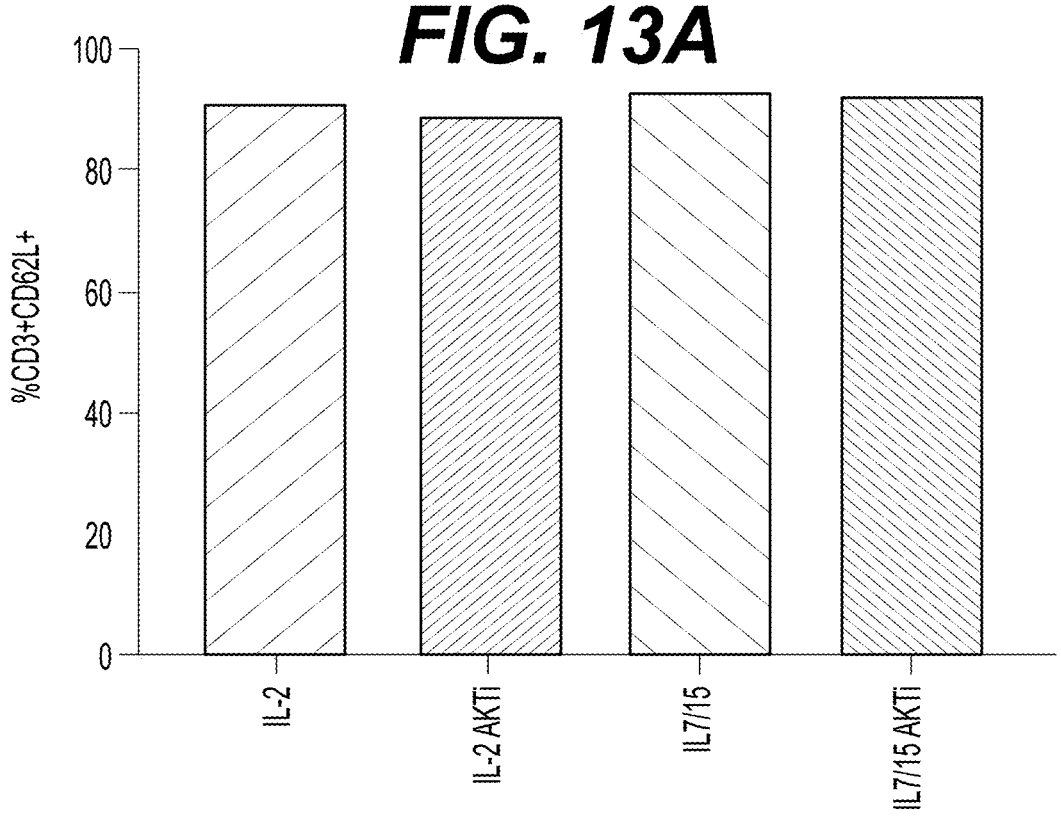
Figure 13C:
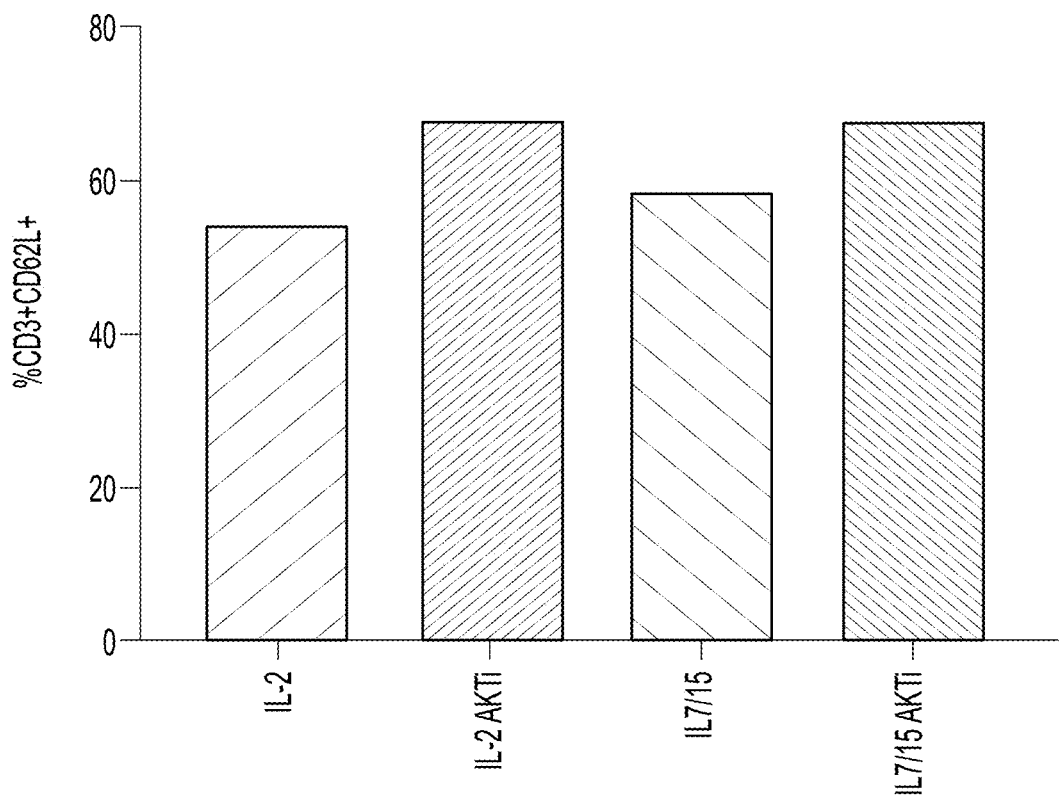
Figure 13D:
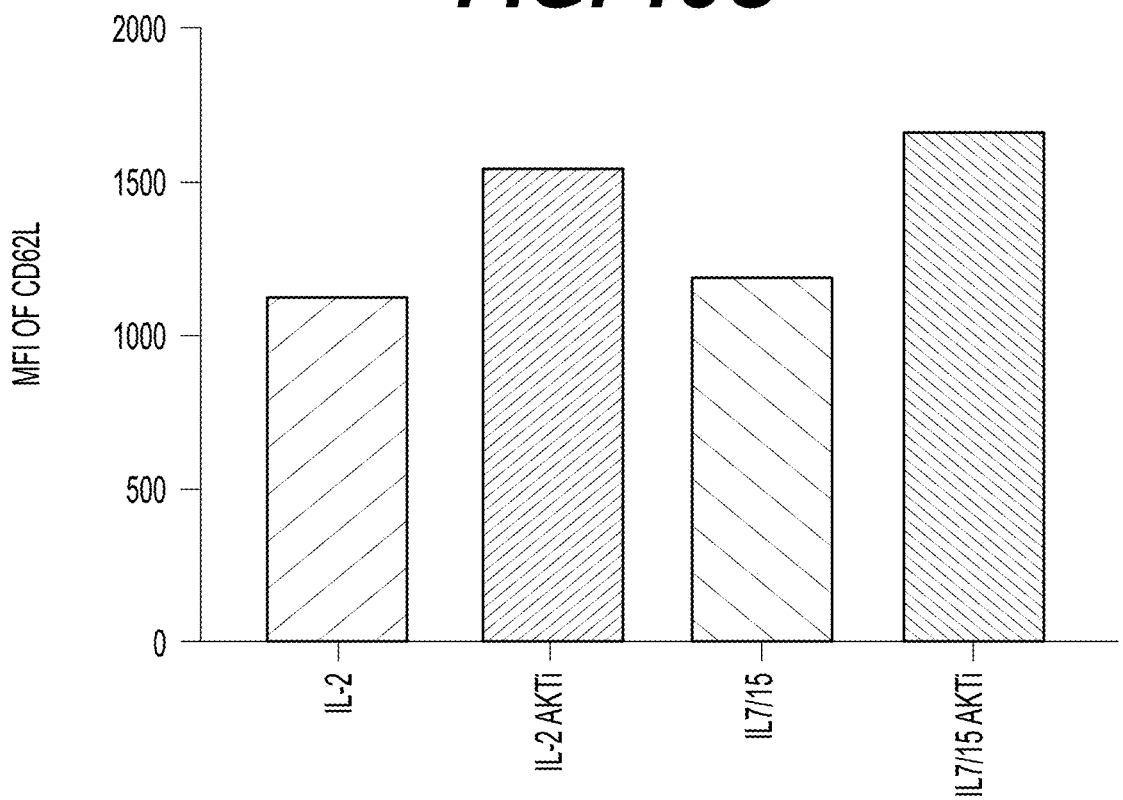
Figure 13E:
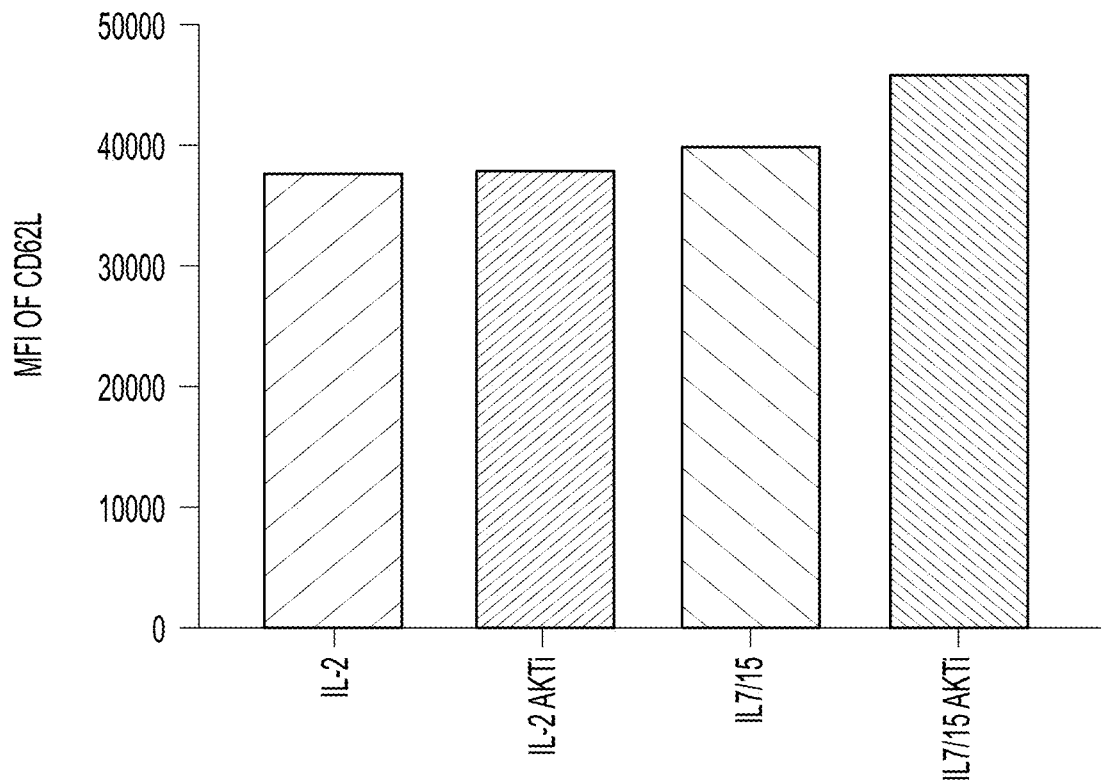
Figure 13F:
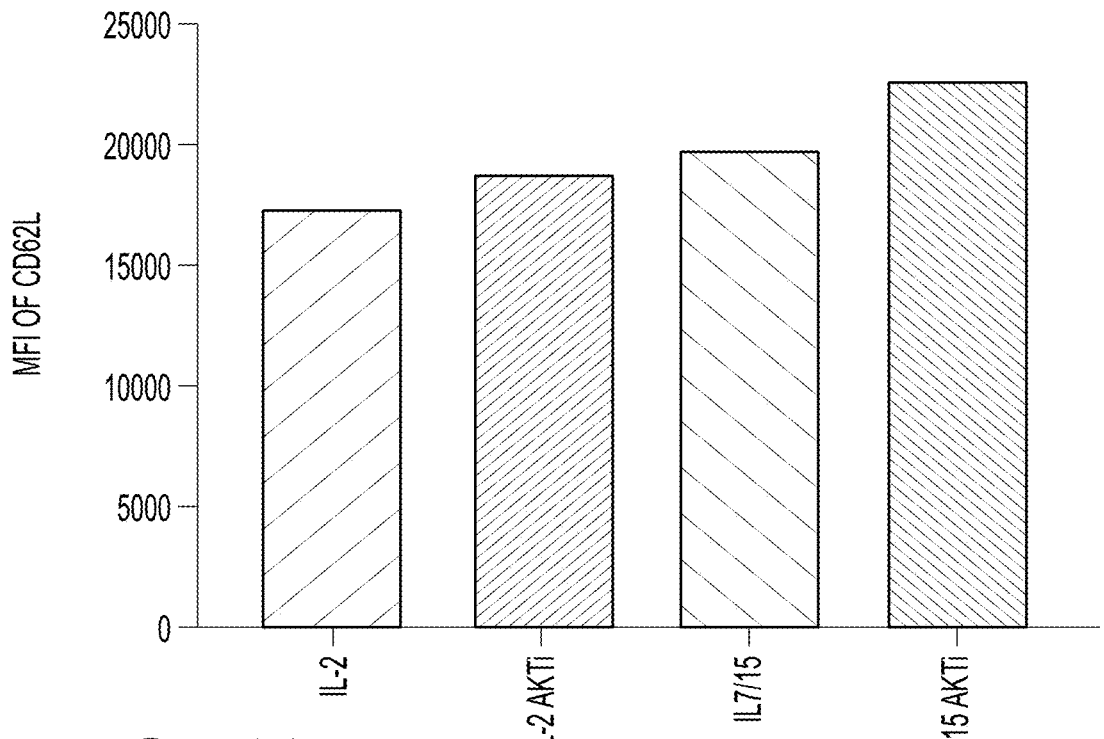

To determine the effect of the various culture conditions on differentiation status, CD4+/CD8+ T cells from three donors were transduced with a Class II TCR (MAGE-A3) and cultured in the presence of IL-2; IL-2 and AKTi; IL-7 and IL-15; and IL-7, IL-15, and AKTi. Cells were then stained with an antibody directed to CD62L, which is a marker of early stages of differentiation. The percent of cells staining positive CD62L expression was determined for cells from each culture condition for each of Donor 1, 2, and 3 (FIGS. 13A, 13B, and 13C, respectively). Mean fluorescence intensity (MFI) indicated that cells cultured in the presence of AKTi had greater levels of CD62L on the surface of positive cells, as compared to cells cultured in the absence of AKTi (FIGS. 13D-13E).

Example 5

Figure 14A:
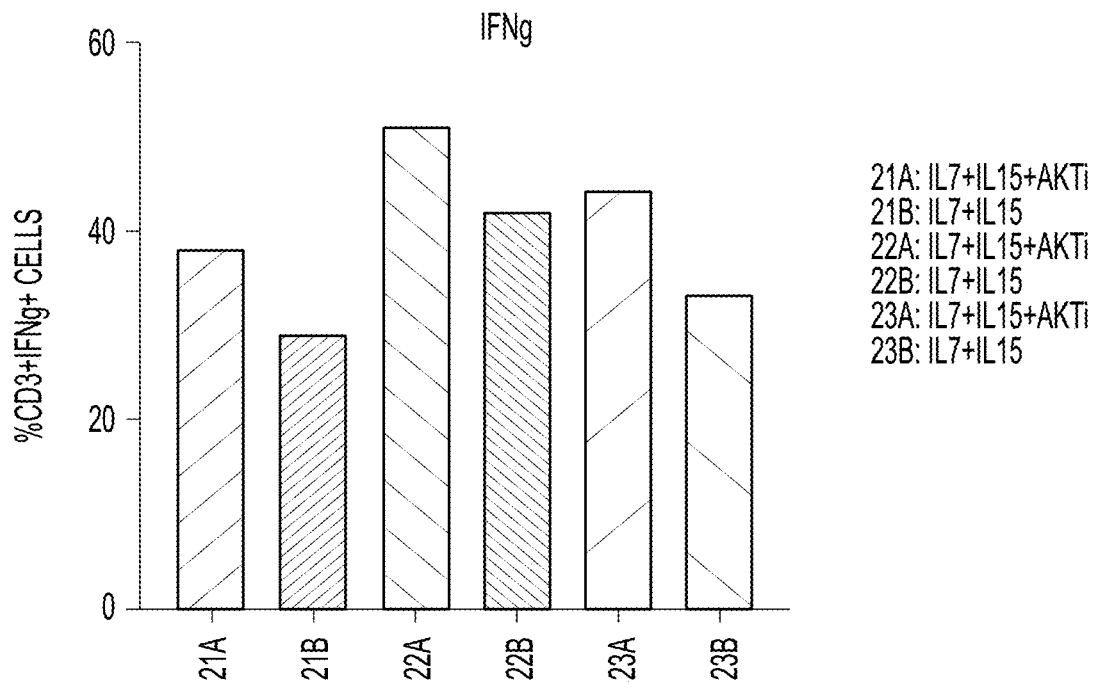
FIGS. 14A-14B show the effects of culture conditions on T cell function, as evidenced by cytokine production by T cells from three manufacturing scale runs (21, 22, and 23). Donor T cells transduced with a class II TCR (MAGE-A3) were cultured in a XURI™ Bioreactor Cell Expansion System in the presence of IL-7 and IL-15 or IL-7, IL-15, and AKTi. The percent of cells staining positive for CD3 and IFNg (FIG. 14A) and CD3 and TNFa (FIG. 14B) are shown for cells cultured in the presence or absence of AKTi for each of runs 21, 22, and 23.
Figure 14B:
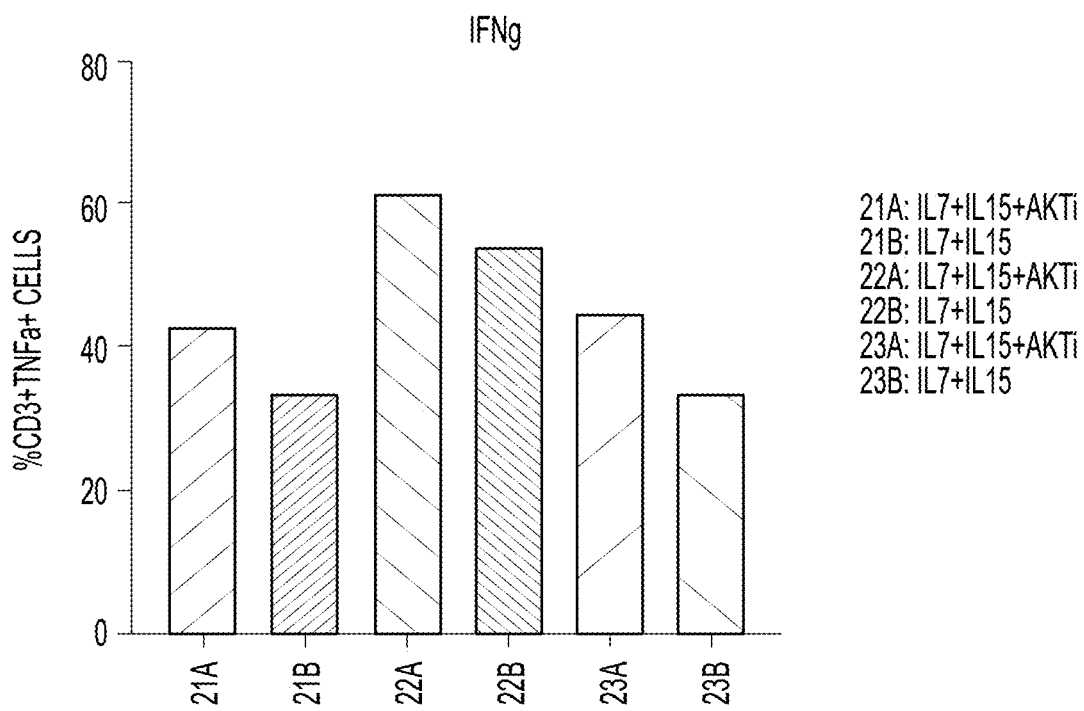

To determine the effects of AKTi on T cell function, cytokine production and T cell proliferation were evaluated following culture under various conditions. T cells from four manufacturing scale runs (21, 22, and 23) were cultured in OriGen PERMALIFE™ bags in the presence of IL-2; IL-2 and AKTi; IL-7 and IL-15; and IL-7, IL-15, and AKTi. T cells were transduced on day 2 with a class II TCR (MAGE-A3) then grown in a XURI™ Bioreactor Cell Expansion System in the presence of IL-7 and IL-15 or IL-7, IL-15, and AKTi. T cells were stimulated with PMA+Ionomycin+BrefaldinA+Monesin for 5.5 hours. Intracellular flow cytometry showed increased T cell activity for cell cultured in the presence of AKTi, as evidenced by increased production of production of the cytokines IFNg (FIG. 14A) and TNFa (FIG. 14B).

Figure 15:
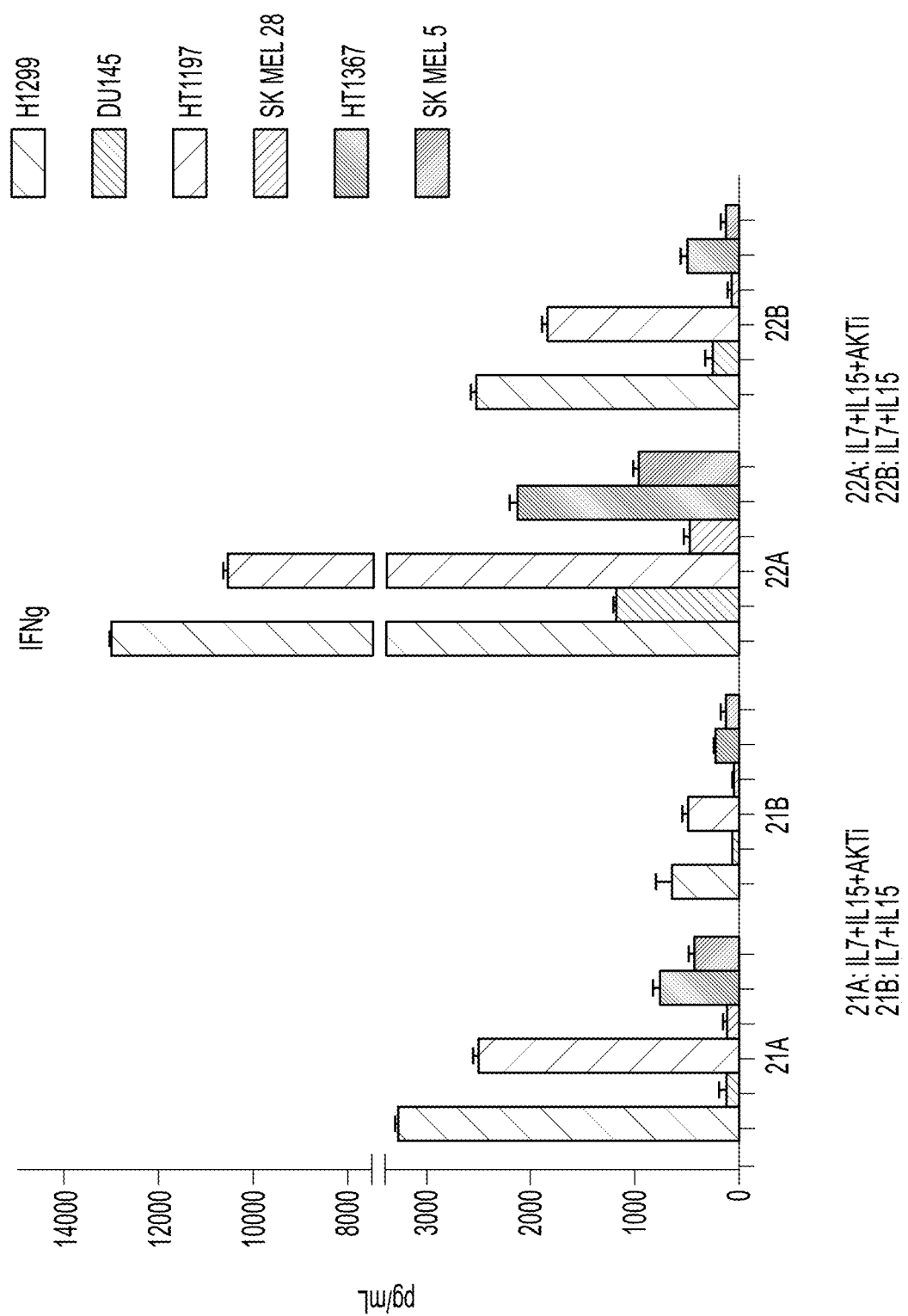
FIG. 15 shows T cell activity as evidenced by IFNg production for donor T cells transduced with a class II TCR (MAGE-A3) and cocultured with positive and negative target tumor cell lines. T cells from two manufacturing scale runs (21 and 22) were transduced with a class II TCR and cultured in a XURI™ Bioreactor Cell Expansion System in the presence of IL-7 and IL-15 or IL-7, IL-15, and AKTi. Cells were then cocultured over night with a tumor cell line that expresses the TCR target antigen (H1299, HT1197, or HT1367) or a tumor cell line that does not express the TCR target antigen (DU145, SK MEL 28, or SK MEL 5). T cell activity is indicated by IFNg production, shown as pg/mL (y-axis), for each of the cell lines (x-axis) for each of the culture conditions. Error bars indicate the standard deviation.

To further confirm that AKTi increases T cell activity, T cells from two manufacturing scale runs (21 and 22) were cultured as described above and cocultured over night with positive (H1299, HT1197, and HT1367) and negative (DU145, SK MEL 28, and SK MEL 5) target tumor cell lines. Cells cultured in the presence of AKTi showed greater IFNg production under each culture condition tested (FIG. 15), indicating that AKTi-cultured cells have a greater potency for responding to a stimulus than cells cultured in the absence of AKTi.

Figure 16A:
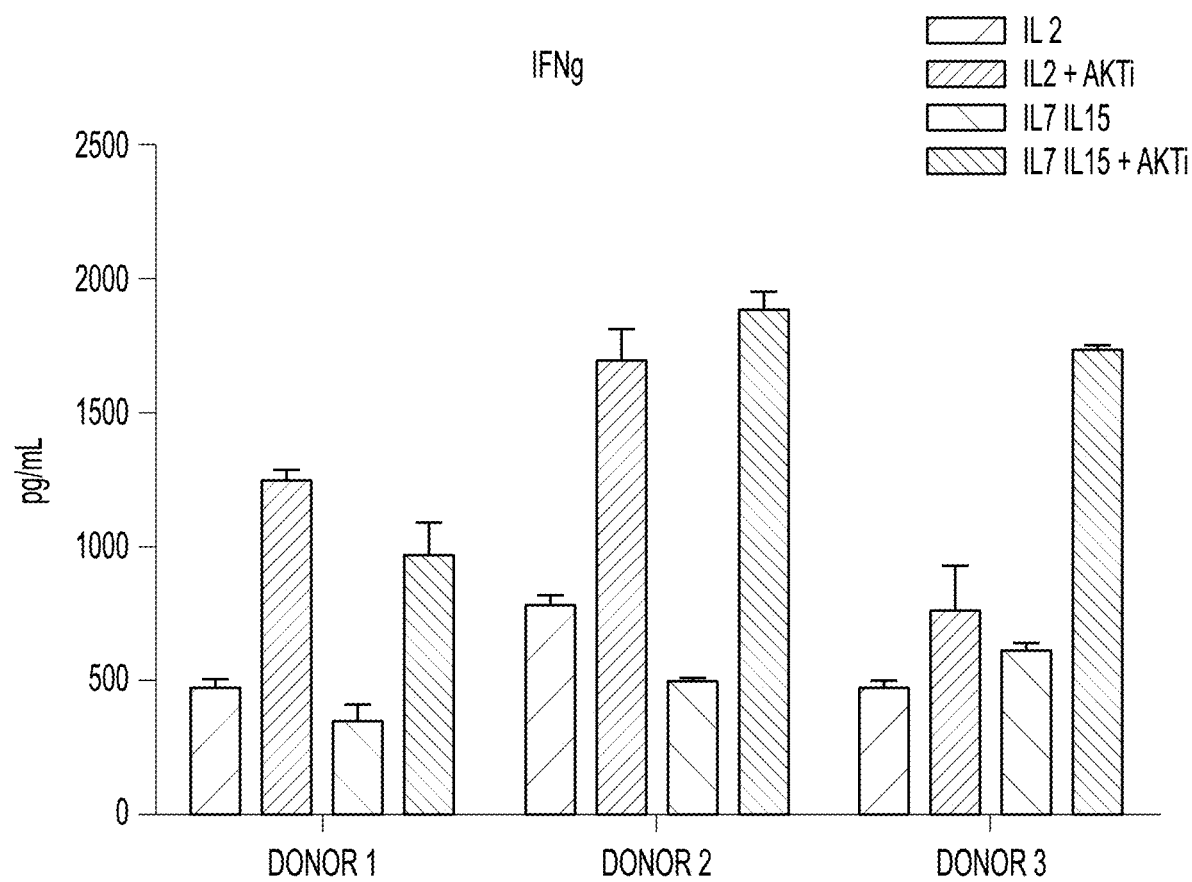
FIGS. 16A-16D show T cell activity as evidenced by IFNg production for three donor T cell lines transduced with a class I TCR (HPV-E6) and cultured with or without AKTi.
Figure 16B:
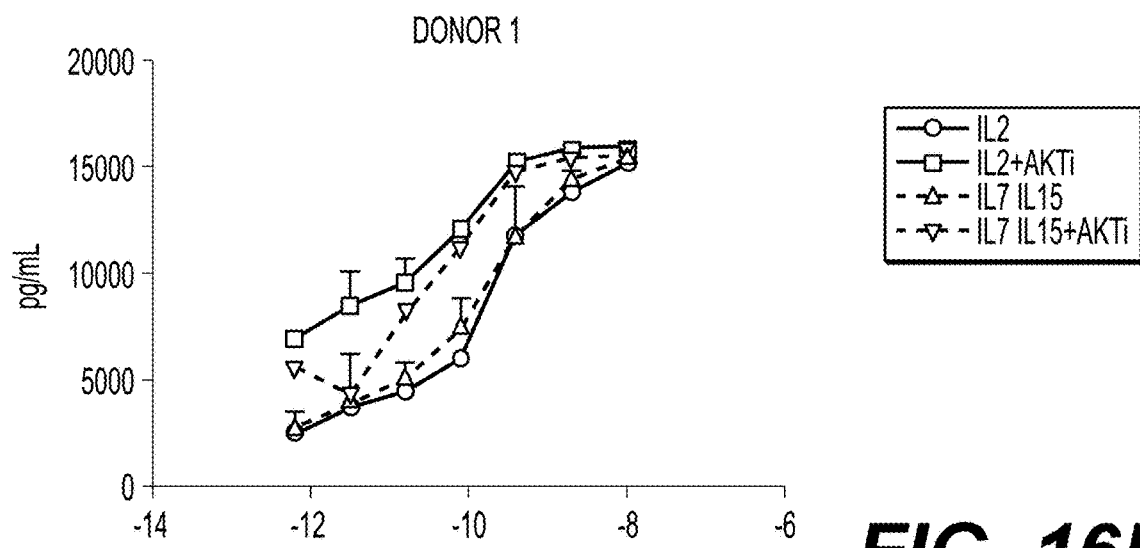
Figure 16C:
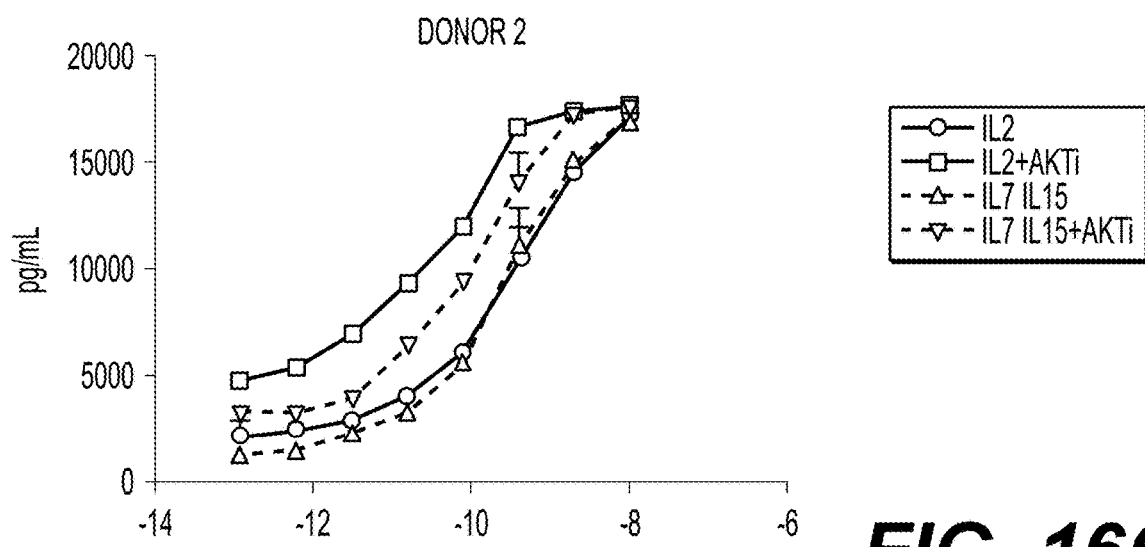
Figure 16D:
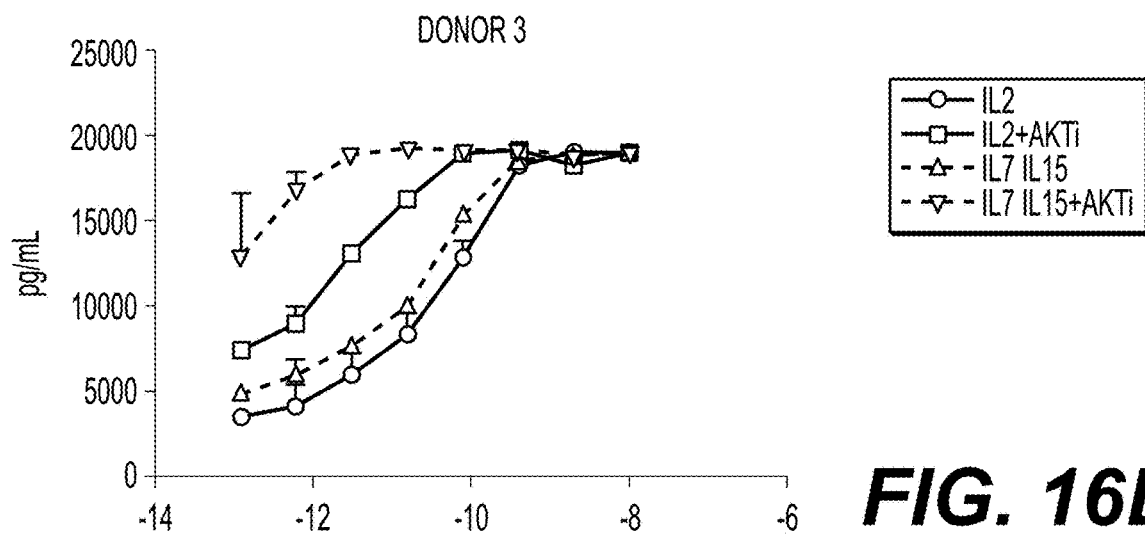

Similar results were observed for small scale culture of donor T cells. Cells from Donor 1, Donor 2, and Donor 3 were stimulated; cultured in the presence of IL-2; IL-2 and AKTi; IL-7 and IL-15; or IL-7, IL-15, and AKTi; and transduced on day 2 post-stimulation with a class I TCR, as described above. T cells were co-cultured over night with a tumor cell line (Caski cells; FIG. 16A) or with T2 cells loaded with titrated amounts of the TCR-specific peptide (FIGS. 16B-16D). As observed in the large scale manufacturing experiments, above, cells cultured in the presence of AKTi produced higher levels of IFNg that cells cultured in the absence of AKTi (FIGS. 16A-16D). Titration of TCR-specific peptide showed that at nearly all levels, AKTi culture conditions induce greater IFNg production.

Figure 17A:
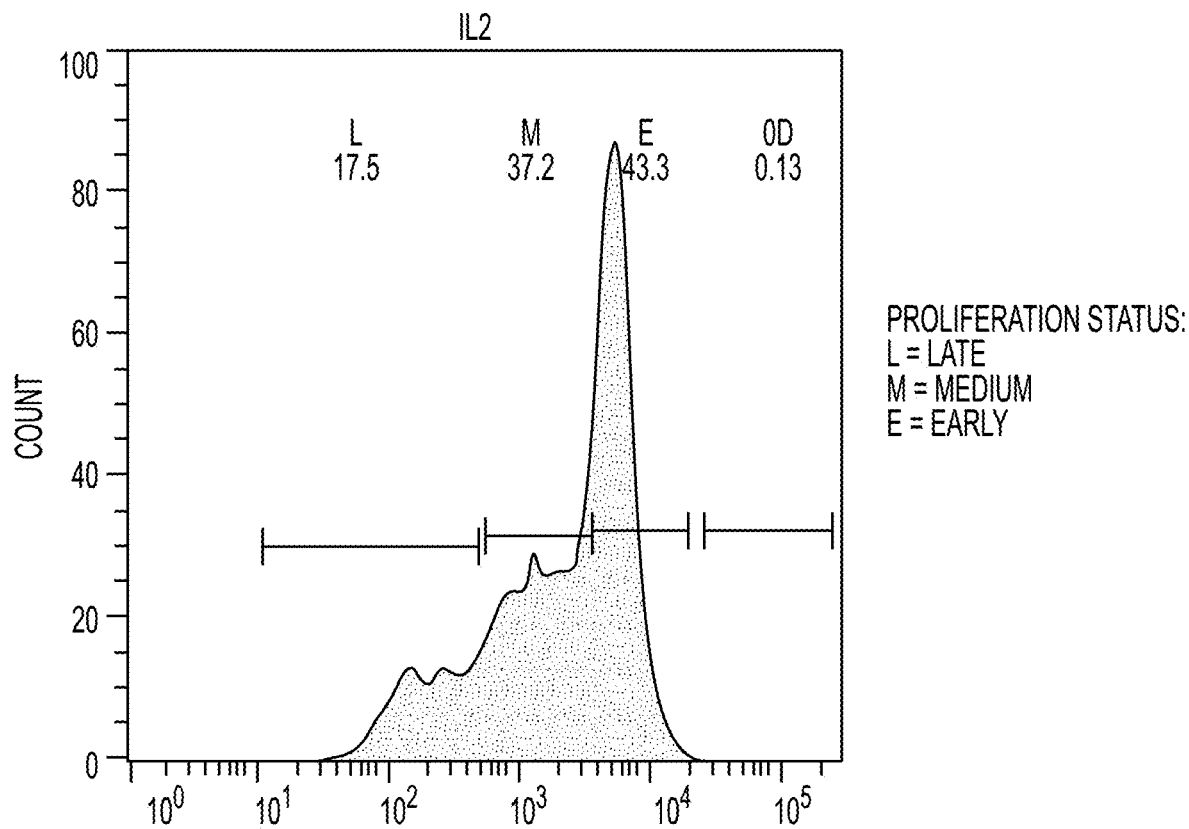
Figure 17B:
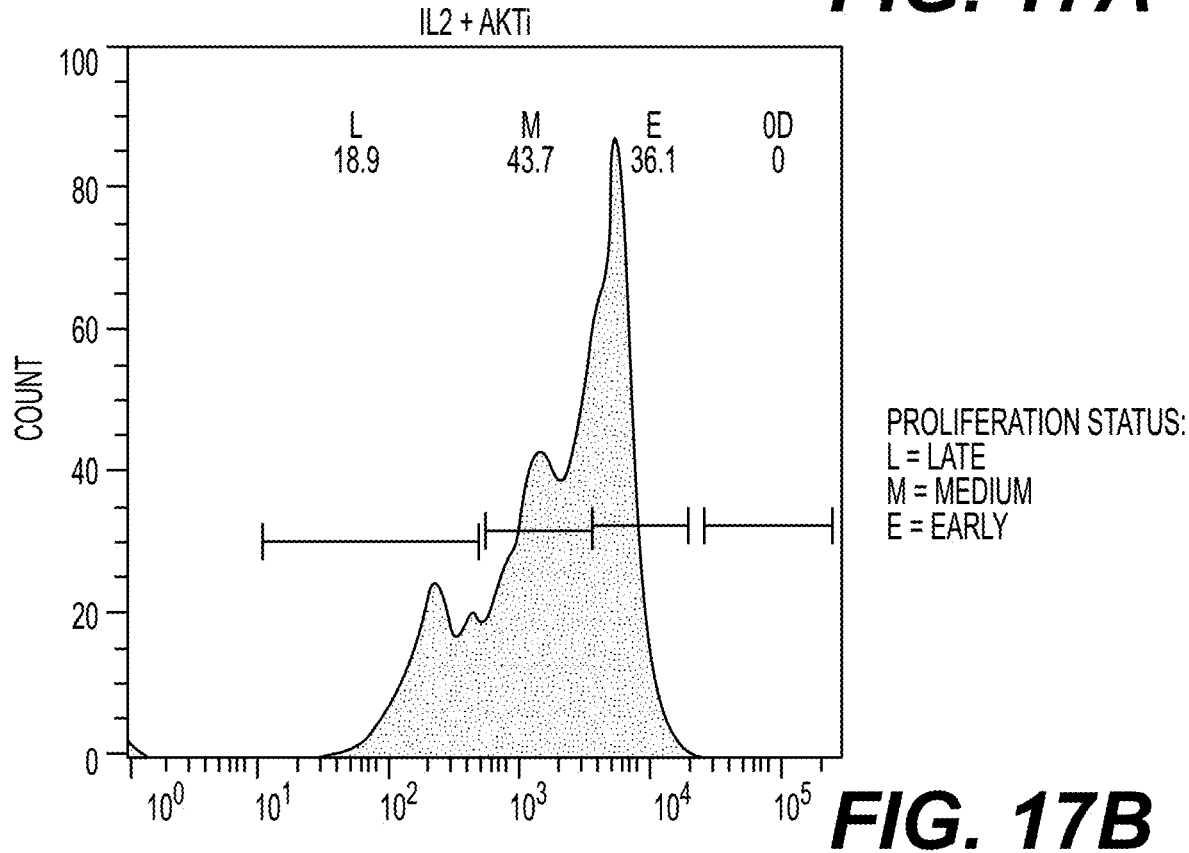
FIGS. 17B-17D show IFNg production (pg/mL; y-axis) for donor T cells following coculture with T2 cells, which were loaded with titrated amounts of the SCR-specific peptide (target peptide; x-axis), in the presence of IL-2 alone (circles); IL-2 and AKTi (squares); IL-7 and IL-15 (triangles); or IL-7, IL-15, and AKTi (inverted triangles) for Donor 1 (FIG. 16B), Donor 2 (FIG. 16C), and Donor 3 (FIG. 16D) T cells. Error bars indicate the standard deviation.
Figure 17C:
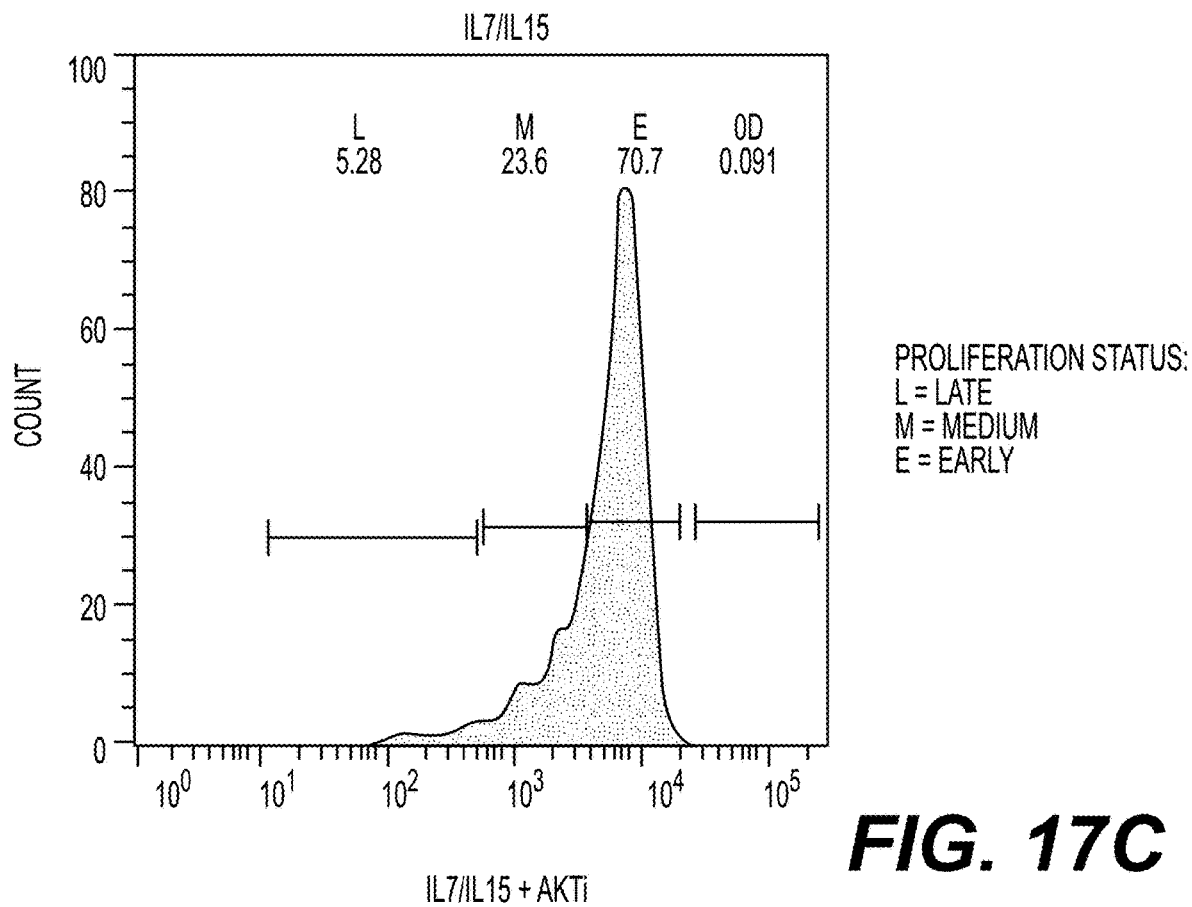
Figure 17D:
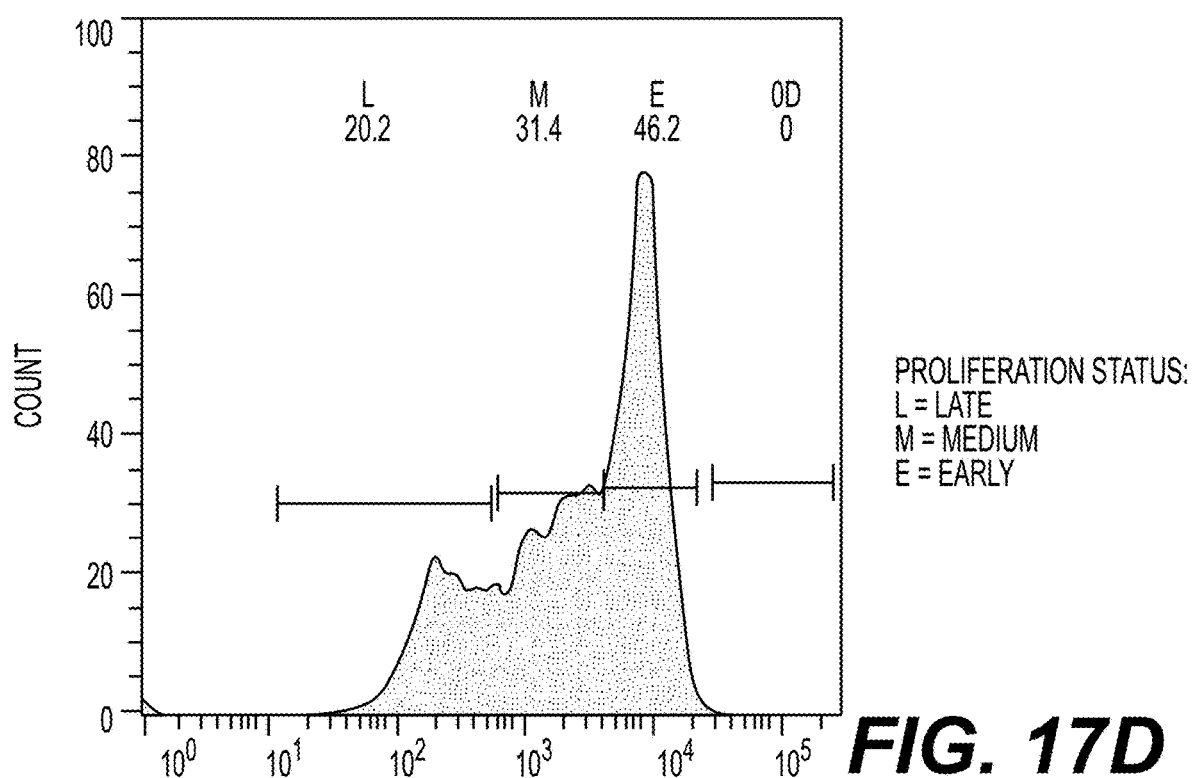

T cell proliferation was also found to increase following culture in the presence of AKTi. T cells from Donor 1, Donor 2, and Donor 3 were transduced on day 2 post-stimulation with a Class II TCR, as described above. T cells were stained with CFSE and co-cultured with a tumor cell line (positive control) for four days. Increased T cell proliferation was observed in cells grown in the presence of AKTi (FIGS. 17B and 17D) as compared to cells grown without AKTi (FIGS. 17A and 17C). FIGS. 17A-17D show representative data from Donor 3, wherein a greater percentage of cells are characterized as being in late (L) or medium (M) proliferation for cells cultured in IL-2 and AKTi (FIG. 17B) and IL-7, IL-15, and AKTi (FIG. 17D) than for cell cultured in the absence of AKTi (FIGS. 17A and 17C).

Figure 18A:
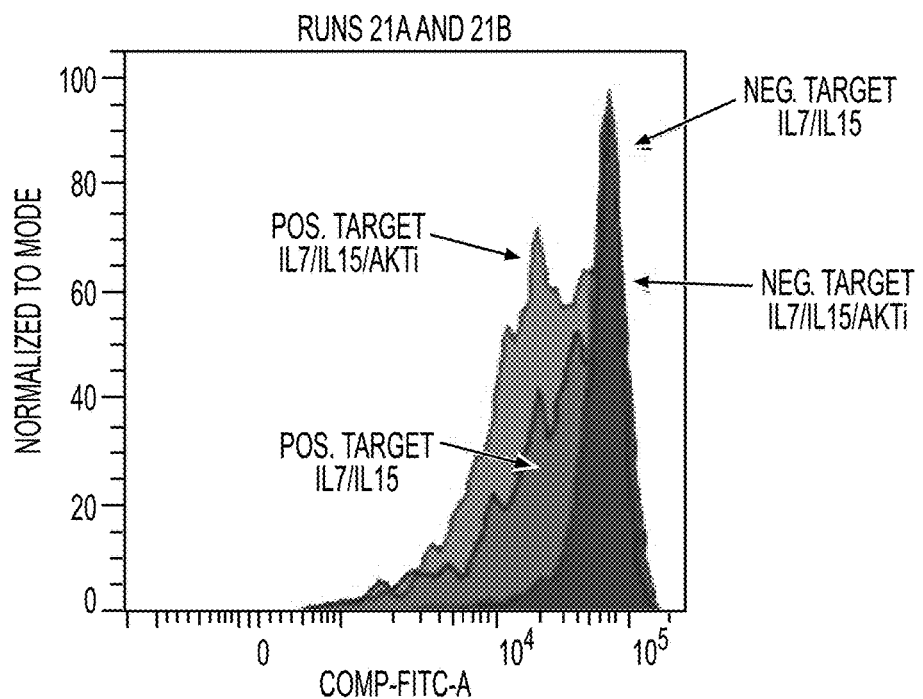
FIGS. 18A and 18B are FACS histograms showing cell proliferation of T cells from two large scale manufacturing culture runs: 21 (FIG. 18A) and 22 (FIG. 18B). T cells were grown in IL-2 and in IL-7, IL-15 and AKTi and transduced with a Class II TCR (MAGE-A3). T cells were cocultured with either a tumor cell line expressing the TCR target antigen ("Pos. target") or a cell line that does not express the TCR target antigen ("Neg. target") in the presence of IL-7 and IL-15 or IL-7, IL-15, and AKTi for 4 days. T cell proliferation was measured by CFSE staining, normalized to the mode, compared to comp-FITC-A staining, as illustrated for each of runs 21 (FIG. 18A) and 22 (FIG. 18B).
Figure 18B:
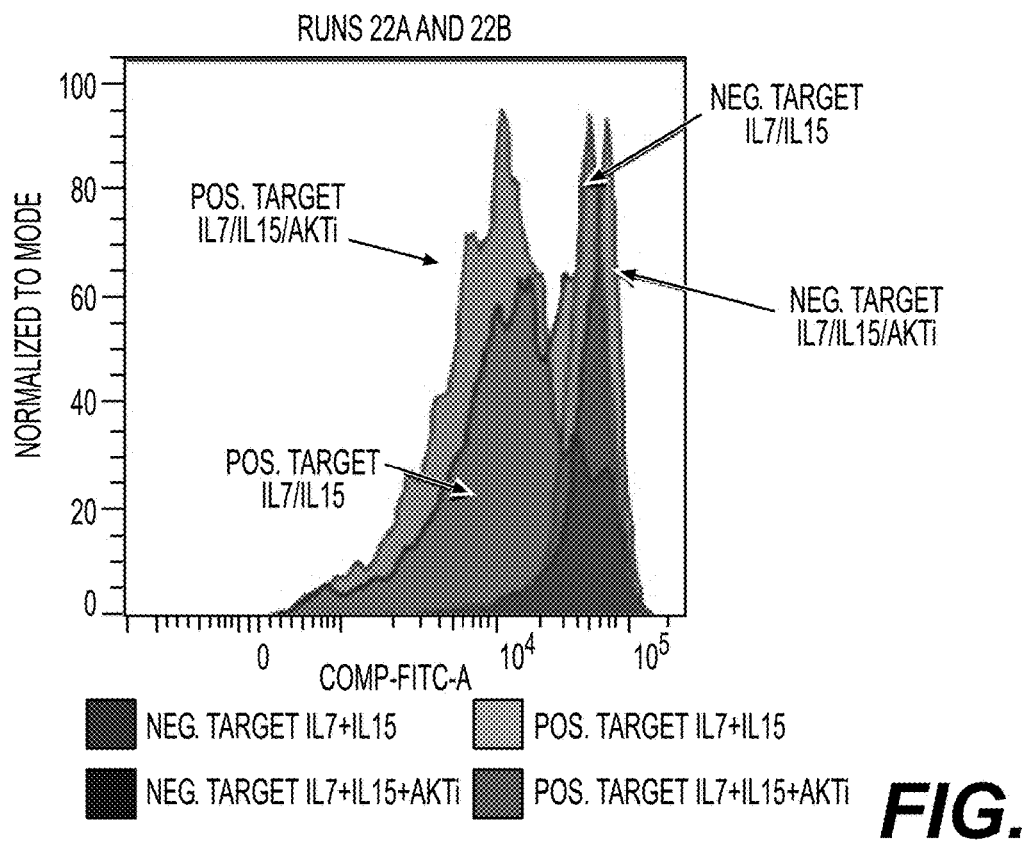

Increased T cell proliferation was also observed under large scale manufacturing culture conditions. T cells from two large scale manufacturing runs (21 and 22) were transduced on day 2 post-stimulatoin with a class II TCR, as described above. T cells were stained with CFSE and co-cultured with a positive tumor cell line or a negative cell line for four days. Increased T cell proliferation was observed in cells grown in the presence of AKTi for each of runs 21A/21B (FIG. 18A) and 22A/22B (FIG. 18B).

Example 6

To determine the effect of AKTi on T cell cytolytic activity, target cells expressing Luciferase are co-cultured with T cells grown under various culture conditions (IL-2 alone; IL-2 and AKTi; IL-7 and IL-15; and IL-7, IL-15, and AKTi), as described above, over a period of time that ranges between 16 to 96 hours. T cells are then cocultured with target cells, which express luciferase. Target cell viability is measured by luciferase intensity, such that a decrease in luciferase intensity indicates T cell recognition and target-specific killing. Accordingly, reduction of luciferase levels is a direct measure of T cell cytotoxicity. It is expected that cells cultured in the presence of an AKT inhibitor will have greater cytotoxicity than cells cultured in the absence of an AKT inhibitor.

What is claimed is:

1. A method for culturing T cells for a T cell therapy while delaying or inhibiting maturation or differentiation of the T cells, comprising:
    contacting, in a culture medium, one or more T cells with exogenous Interleukin-7 (IL-7) and exogenous Interleukin-15 (IL-15) in the absence of exogenous Interleukin-2 (IL-2),
    wherein the one or more T cells comprise CD4+ T cells, and the contacting is for 1 day to 10 days such that the CD4+ T cells, following such contacting, comprise a higher percentage of naive T cells and central memory T (Tcm) cells as compared to when the CD4+ T cells are contacted with exogenous IL-2 in the absence of exogenous IL-7 and exogenous IL-15.

2. The method of claim 1, wherein the one or more T cells are further contacted with an AKT inhibitor.

3. The method of claim 2, wherein the AKT inhibitor is selected from the group consisting of A6730, B2311, 124018, GSK2110183 (afuresertib), Perifosine (KRX-0401), GDC-0068 (ipatasertib), RX-0201, VQD-002, LY294002, A-443654, A-674563, Akti-1, Akti-2, Akti-1/2, AR-42, API-59CJ-OMe, ATI-13148, AZD-5363, erucylphosphocholine, GSK-2141795 (GSK795), KP372-1, L-418, NL-71-101, PBI-05204, PIA5, PX-316, SR13668, triciribine, GSK 690693 (CAS #937174-76-0), FPA 124 (CAS #902779-59-3), Miltefosine, PHT-427 (CAS #1 191951-57-1), 10-DEBC hydrochloride, Akt inhibitor III, Akt inhibitor VIII, MK-2206 dihydrochloride (CAS

1032350-13-2), SC79, AT7867 (CAS #857531-00-1), CCT128930 (CAS #885499-61-6), A-674563 (CAS #552325-73-2), AGL 2263, AS-041 164 (5-benzo[1,3]dioxol-5-ylmethylene-thiazolidine-2,4-dione), BML-257 (CAS #32387-96-5), XL-418, CAS #612847-09-3, CAS #98510-80-6, H-89 (CAS #127243-85-0), OXY-1 1 1 A, 3-[1-[[4-(7-phenyl-3H-imidazo[4,5-g]quinoxalin-6-yl)phenyl]methyl]piperidin-4-yl]-1H-benzimidazol-2-one, N,N-dimethyl-1-[4-(6-phenyl-1H-imidazo[4,5-g]quinoxalin-7-yl)phenyl]metha-namine, 1-{1-[4-(3-phenylbenzo[g]quinoxalin-2-yl)benzyl]piperidin-4-yl}-1,3-dihydro-2H-benzimidazol-2-one and any combination thereof.

4. The method of claim 2, wherein the AKT inhibitor is 3-[1-[[4-(7-phenyl-3H-imidazo[4,5-g]quinoxalin-6-yl)phenyl]methyl]piperidin-4-yl]-1H-benzimidazol-2-one.

5. The method of claim 2, wherein:
(i) the AKT inhibitor is at an amount of from about 1 nM to about 1 mM;
(ii) the exogenous IL-7 is at an amount of about 0.001 to about 500 ng/ml IL-7;
(iii) the exogenous IL-15 is at an amount of about 0.001 to about 500 ng/ml IL-15; or
(iv) any combination of (i) to (iii).

6. The method of claim 2, wherein:
(i) the AKT inhibitor is at an amount of about 8 µM;
(ii) the exogenous IL-7 is at an amount of at least about 5 ng/ml IL-7;
(iii) the exogenous IL-15 is at an amount of at least about 5 ng/ml IL-15; or
(iv) any combination of (i) to (iii).

7. The method of claim 1, wherein the one or more T cells comprise CD4+ T cells and CD8+ T cells.

8. The method of claim 1, further comprising transducing the T cells with a retrovirus.

9. The method of claim 8, wherein the retrovirus comprises a heterologous gene encoding a T cell receptor (TCR) or a chimeric antigen receptor (CAR).

10. The method of claim 9, wherein the TCR or the CAR is capable of binding an antigen selected from the group consisting of 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), κ-light chain, LAGE (L antigen), LDLR/FUT (low density lipid receptor/GDP-L-fucose: b-D-galactosidase 2-a-Lfucosyltransferase), LeY (Lewis-Y antibody), L1CAM (L1 cell adhesion molecule), MAGE (melanoma antigen), MAGE-A1 (Melanoma-associated antigen 1), MAGE-A3, MAGE-A6, mesothelin, Murine CMV infected cells, MART-1/Melan-A (melanoma antigen recognized by T cells-1/Melanoma antigen A), MC1R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), WT1 (Wilms' tumor gene), and any combination thereof.

11. The method of claim 1, wherein the exogenous IL-7 and exogenous IL-15, each is present in the culture medium, at a concentration that is at least 7 ng/mL.

12. The method of claim 11, wherein the exogenous IL-7 and exogenous IL-15 each is present at a concentration that is at least 10 ng/mL.

* * * * *